United States Patent
Cammarano et al.

(10) Patent No.: US 11,103,456 B2
(45) Date of Patent: *Aug. 31, 2021

(54) METHODS FOR THE PREPARATION OF BIOLOGICALLY ACTIVE COMPOUNDS IN NANOPARTICULATE FORM

(71) Applicant: ICEUTICA PTY LTD., Iluka (AU)

(72) Inventors: Raffaele Cammarano, Freemantle (AU); Felix Meiser, Claremont (AU); Almar Postma, Victoria (AU); Frank Caruso, Preston (AU)

(73) Assignee: iCeutica Pty Ltd., Iluka, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/016,443

(22) Filed: Jun. 22, 2018

(65) Prior Publication Data

US 2018/0369145 A1 Dec. 27, 2018

Related U.S. Application Data

(63) Continuation of application No. 14/461,594, filed on Aug. 18, 2014, now abandoned, which is a continuation of application No. 12/306,948, filed as application No. PCT/AU2007/000910 on Jun. 29, 2007, now Pat. No. 8,808,751.

(60) Provisional application No. 60/915,955, filed on May 4, 2007.

(30) Foreign Application Priority Data

Jun. 30, 2006 (AU) ................. 2006903527

(51) Int. Cl.
| | | |
|---|---|---|
| A61K 9/51 | (2006.01) | |
| A61K 9/14 | (2006.01) | |
| A61K 31/192 | (2006.01) | |
| A61K 31/196 | (2006.01) | |
| A61K 31/435 | (2006.01) | |
| A61K 31/4985 | (2006.01) | |
| A61K 31/5513 | (2006.01) | |
| A61K 31/4535 | (2006.01) | |
| A61K 31/551 | (2006.01) | |

(52) U.S. Cl.
CPC ............ *A61K 9/143* (2013.01); *A61K 9/145* (2013.01); *A61K 9/5115* (2013.01); *A61K 9/5123* (2013.01); *A61K 31/192* (2013.01); *A61K 31/196* (2013.01); *A61K 31/435* (2013.01); *A61K 31/4535* (2013.01); *A61K 31/4985* (2013.01); *A61K 31/551* (2013.01); *A61K 31/5513* (2013.01)

(58) Field of Classification Search
None
See application file for complete search history.

(56) References Cited

U.S. PATENT DOCUMENTS

| | | |
|---|---|---|
| 4,133,814 A | 1/1979 | Jones et al. |
| 4,380,635 A | 4/1983 | Peters |
| 4,418,068 A | 11/1983 | Jones |
| 4,605,517 A | 8/1986 | Riley et al. |
| 4,607,517 A | 8/1986 | Finzer et al. |
| 5,145,684 A | 9/1992 | Liversidge et al. |
| 5,202,129 A | 4/1993 | Samejima et al. |
| 5,298,262 A | 3/1994 | Na et al. |
| 5,470,583 A | 11/1995 | Na et al. |
| 5,478,705 A | 12/1995 | Czekai et al. |
| 5,500,331 A | 3/1996 | Czekai et al. |
| 5,510,118 A | 4/1996 | Bosch et al. |
| 5,518,187 A | 5/1996 | Bruno et al. |
| 5,534,270 A | 7/1996 | De Castro |
| 5,591,456 A | 1/1997 | Franson et al. |
| 5,718,388 A | 2/1998 | Czekai et al. |
| 5,972,389 A | 10/1999 | Shell et al. |
| 6,022,564 A | 2/2000 | Takechi et al. |
| 6,165,506 A | 12/2000 | Jain et al. |
| 6,316,026 B1 | 11/2001 | Tatara et al. |
| 6,316,029 B1 | 11/2001 | Jain et al. |
| 6,428,814 B1 | 8/2002 | Bosch et al. |
| 6,634,576 B2 | 10/2003 | Verhoff et al. |
| 6,713,494 B1 | 3/2004 | Cuff et al. |
| 6,811,767 B1 | 11/2004 | Bosch et al. |
| 6,894,064 B2 | 5/2005 | Arbuthnot et al. |
| 6,908,626 B2 | 6/2005 | Cooper et al. |
| 7,101,576 B2 | 9/2006 | Hovey et al. |
| 8,808,751 B2 | 8/2014 | Cammarano et al. |
| 2002/0012675 A1 | 1/2002 | Jain et al. |
| 2002/0047058 A1 | 4/2002 | Verhoff et al. |
| 2003/0137067 A1 | 7/2003 | Cooper et al. |
| 2003/0228357 A1 | 12/2003 | Johnson et al. |
| 2004/0037785 A1 | 2/2004 | Staniforth et al. |
| 2004/0058009 A1 | 3/2004 | Ryde et al. |

(Continued)

FOREIGN PATENT DOCUMENTS

| | | |
|---|---|---|
| EP | 0371431 | 6/1990 |
| EP | 0670162 | 9/1995 |

(Continued)

OTHER PUBLICATIONS

Bahl et al. "Amorphization of Indomethacin by Co-Grinding with Neusiling US2: Amorphization Kinetics, Physical Stability and Mechanism," Pharmaceutical Research, (2006), vol. 23 (10), pp. 2317-2325.

Barzegar-Jalali et al. "Evaluation of in vitro—in vivo correlation and anticonvulsive effect of carbamazepine after cogrinding with microcrystalline cellulose" J Pharm Pharmaceut Science (2006), vol. 9 (3), pp. 307-316. See abstract, pp. 308-313.

Fukami et al. "A nanoparticle processing in solid state dramatically increases the cell membrane permeation of a cholesterol lowering drug", Mol. Pharmaceutics, 6 (3):1029-1035, 2009.

(Continued)

*Primary Examiner* — Jessica Worsham
(74) *Attorney, Agent, or Firm* — Fish & Richardson P.C.

(57) ABSTRACT

A method for producing a composition comprising nanoparticles of a biologically active compound.

9 Claims, 26 Drawing Sheets

(56) References Cited

U.S. PATENT DOCUMENTS

| | | |
|---|---|---|
| 2004/0173696 A1 | 9/2004 | Cunningham et al. |
| 2005/0019412 A1 | 1/2005 | Bosch et al. |
| 2005/0063913 A1 | 3/2005 | Pruitt et al. |
| 2006/0154966 A1 | 7/2006 | Karup et al. |
| 2007/0059356 A1 | 3/2007 | Almarsson et al. |
| 2008/0254128 A1 | 10/2008 | Zarkadas et al. |
| 2009/0028948 A1 | 1/2009 | Payne et al. |
| 2010/0092563 A1 | 4/2010 | Raffaele et al. |
| 2012/0263760 A1 | 10/2012 | Dodd et al. |
| 2015/0164802 A1 | 6/2015 | Cammarano et al. |

FOREIGN PATENT DOCUMENTS

| | | |
|---|---|---|
| EP | 0699672 | 3/1996 |
| EP | 0600528 | 6/2000 |
| JP | 1991066613 | 3/1991 |
| JP | 2010/167968 | 6/1998 |
| JP | 1998167968 | 6/1998 |
| JP | 2000-502365 | 2/2000 |
| JP | 2002-512183 | 4/2002 |
| JP | 2004-009942 | 1/2004 |
| JP | 2005/508939 | 4/2005 |
| JP | 2006/501233 | 1/2006 |
| JP | 2012-524717 | 10/2012 |
| JP | 2012-524719 | 10/2012 |
| WO | WO 1998/015280 | 4/1998 |
| WO | WO 1999/009988 | 3/1999 |
| WO | WO 1999/053901 | 10/1999 |
| WO | WO 1999/059754 | 11/1999 |
| WO | WO 2002/000197 | 1/2002 |
| WO | WO 2002/056866 | 7/2002 |
| WO | WO 2002/094215 | 11/2002 |
| WO | WO 2003/097012 | 11/2003 |
| WO | WO 2004/058216 | 7/2004 |
| WO | WO 2004/060344 | 7/2004 |
| WO | WO 2005/002542 | 1/2005 |
| WO | WO 2005/013937 | 2/2005 |
| WO | WO 2005/016310 | 2/2005 |
| WO | WO 2005/020933 | 3/2005 |
| WO | WO 2005/032703 | 4/2005 |
| WO | WO 2006/031026 | 3/2006 |
| WO | WO 2006/041843 | 4/2006 |
| WO | WO 2006/060698 | 6/2006 |
| WO | WO 2006/009419 | 7/2006 |
| WO | WO 2006/069419 | 7/2006 |
| WO | WO 2007/001451 | 1/2007 |
| WO | WO 2007/070843 | 6/2007 |
| WO | WO 2007/070851 | 6/2007 |
| WO | WO 2007/070852 | 6/2007 |
| WO | WO 2008/000042 | 1/2008 |
| WO | WO 2008/118331 | 10/2008 |
| WO | WO 2009/027337 | 3/2009 |
| WO | WO 2010/017104 | 2/2010 |
| WO | WO 2010/121320 | 10/2010 |
| WO | WO 2010/121321 | 10/2010 |
| WO | WO 2010/121322 | 10/2010 |
| WO | WO 2010/121323 | 10/2010 |
| WO | WO 2010/121324 | 10/2010 |
| WO | WO 2010/121325 | 10/2010 |
| WO | WO 2010/121326 | 10/2010 |
| WO | WO 2010/121327 | 10/2010 |
| WO | WO 2010/121328 | 10/2010 |

OTHER PUBLICATIONS

Gibofsky et al., "Efficacy and safety of low-dose submicron diclofenac for the treatment of osteoarthritis pain: a 12 week, phase 3 study," Current Medical Research & Opinion, Sep. 2014, 30(9):1883-1893.

Gibofsky et al., "Lower-Dose Diclofenac Submicron Particle Capsules Provide Early and Sustained Acute Patient Pain Relief in a Phase 3 Study," Postgraduate Medicine, Sep. 2013, 125(5):130-138.

Grigorieva et al., "Mechanosynthesis of nanocomposites," Journal of Nanoparticle Research vol. 5, p. 439-453, 2003.

Gupta et al. "Formation of Physically Stable Amorphous Drugs by Milling with Neusilin," Journal of Pharmaceutical Sciences, (2003), vol. 92 (3), pp. 536-551.

Guterres et al., "Poly(D,L-lactide) nanocapsules containing non-steroidal anti-inflammatory drugs: gastrointestinal tolerance following intravenous and oral administration", Pharmaceutical Research, 12(10): 1545-1547, 1995.

Juhnke et al: "Nanoparticles of soft materials by high-energy milling at low temperatures", 7th World Congress of Chemical Engineering, Glasgow, XP55031954, pp. 1-10, Jan. 2005.

Kondo, "A design and development of novel polymeric prodrugs prepared by mechanochemical solid-state polymerization," Journal of Pharmaceutical Society of Japan, 120(12):1337-1346, 2000.

Itoh, K. et al., "Nanoparticle Formation of Poorly Water-Soluble Drugs from Ternary Ground Mixtures with PVP and SOS", Chem. Pharm. Bull., 51, pp. 171-174, 2003.

McCormick et al., "The Fundamentals of Mechanochemical Processing", Journal of Metals, vol. 50(11):61-65, 1998.

Merisko-Liversidge, E. et al., "Nanosizing: a formulation approach for poorly-water-soluble compounds", European journal of Pharmaceutical Sciences, 8, pp. 113-120, 2003.

Pediatric Migraine Management, Pain management News, 2003, www.wehealny.org/services/bi_pedsepilepsycenter/PedMigraine%20editted%20pain%20medicine%20news.pdf (retrieved Apr. 11, 2016).

Schaffazick et al., "Freeze-drying polymeric colloidal suspensions: nanocapsules, nanospheres and nanodispersion. A comparative study" European Journal of Pharmaceuticals and Biopharmaceuticals, 56(3): 501-505, 2003.

Tsuzuki and McCormick, "Mechanochemical Synthesis of Metal Sulphide Nanoparticles," Nanostructured Materials, vol. 12 p. 75-78, 1999.

Tsuzuki and McCormick, "Mechanochemical synthesis of nanoparticles," Journal of Materials Science, vol. 39, p. 5143-5146, 2004.

Tsuzuki et al., "Mechanochemical Synthesis of Gadolinium Oxide Nanoparticles," Nanostructured Materials, vol. 11, No. 1, p. 125-131, 1999.

Tsuzuki et al., "Synthesis of CaC03 nanoparticles by mechanochemical processing." Journal of Nanoparticle Research, vol. 2, p. 375-380, 2000.

International Preliminary Report on Patentability in International Application No. PCT/AU2007/000910, dated Nov. 6, 2009, 6 pages.

International Search Report in International Application No. PCT/AU2007/000910, dated Aug. 24, 2007, 2 pages.

Office Action from corresponding Canadian Application No. 2,653,384, dated Mar. 10, 2014, pp. 1-3.

Office Action in corresponding Japanese patent application No. 2013-217782, dated Oct. 28, 2014, pp. 1-21.

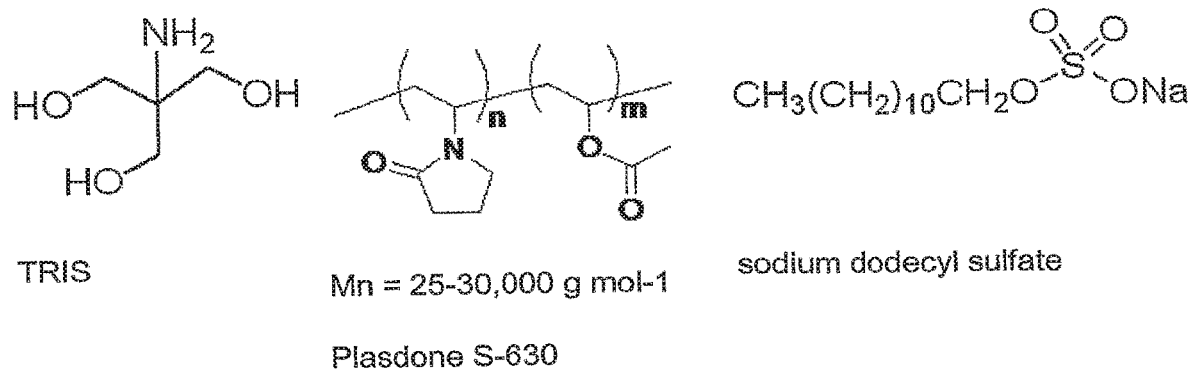
FIG. 19
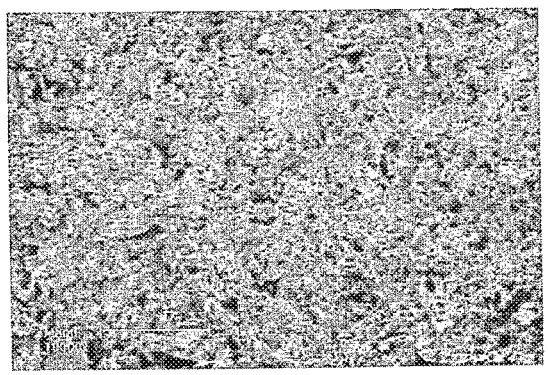 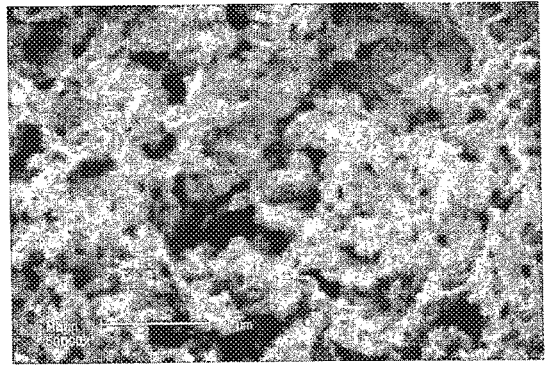
FIG. 20A  FIG. 20B

1) Group A

Order of Administration: Occasion 1 = Test Substance 1;
   Occasion 2 = Test Substance 2

Graphs of Individual Concentration vs Time Data

2) Group B
Order of Administration: Occasion 1 = Test Substance 2; Occasion 2 = Test Substance 1

Mean Concentration vs Time Data

Raloxifene Plasma Concentration (ng/mL)

| Time (hr) | Test Substance 1 (iCeutica nanoparticles) | | Test Substance 2 (commercial API) | |
|---|---|---|---|---|
| | Mean | SD | Mean | SD |
| 0 | 0.24 | 0.81 | 0.36 | 0.96 |
| 0.5 | 7.09 | 5.13 | 4.19 | 2.52 |
| 1 | 7.94 | 3.30 | 6.87 | 3.65 |
| 1.5 | 8.79 | 3.75 | 6.60 | 4.70 |
| 2 | 8.15 | 3.89 | 5.11 | 4.61 |
| 3 | 5.35 | 2.64 | 4.18 | 1.73 |
| 4 | 6.20 | 7.50 | 3.60 | 1.97 |
| 6 | 4.29 | 2.44 | 2.64 | 0.55 |
| 8 | 3.51 | 0.77 | 3.15 | 1.28 |
| 16 | --- | --- | --- | --- |
| 24 | --- | --- | --- | --- |

Mean (SD) Concentration vs Time Data All Animals

Mean Pharmacokinetic Data – Test Substances 1 and 2

|  |  | $C_{max}$ (ng/mL) | $T_{max}^a$ (h) | $k_{elim}$ (h$^{-1}$) | $t_{half}$ (h) | $AUC_{0-t}$ (ng.h/mL) | $AUC_{0-inf}$ (ng.h/mL) |
|---|---|---|---|---|---|---|---|
| Test Substance 1: | Mean | 12.26 | 1.00 | 0.4191 | 1.91 | 33.39 | 42.12 |
|  | SD | 5.47 | --- | 0.1714 | 0.77 | 20.54 | 21.82 |
| Test Substance 2: | Mean | 7.69 | 1.50 | 0.3050 | 3.06 | 21.36 | 36.62 |
|  | SD | 4.54 | --- | 0.1576 | 2.12 | 16.79 | 23.45 |

$^a$median

FIG. 25

Comparison of $C_{max}$ and $AUC_{0-t}$ Results: Test Substances 1 and 2

| Dog Name (Group) | Pharmacokinetic Parameter | | | |
|---|---|---|---|---|
| | $C_{max}$ (ng/mL) | | $AUC_{0-t}$ (ng.h/mL) | |
| | Test Substance | | Test Substance | |
| | 1 | 2 | 1 | 2 |
| Griselda (A) | 16.40 | 3.94 | 20.29 | 9.27 |
| Ice (A) | 24.50 | 18.00 | 70.54 | 45.02 |
| Ginger (A) | 14.80 | 4.30 | 36.31 | 7.68 |
| Champ (A) | 15.80 | 9.50 | 65.04 | 17.86 |
| Chuck (A) | 9.85 | 10.40 | 39.94 | 20.74 |
| C50606 (A) | 10.70 | 5.89 | 31.68 | 15.73 |
| C60606 (B) | 13.20 | 7.83 | 50.08 | 58.48 |
| Grizz (B) | 7.28 | 13.60 | 12.81 | 37.18 |
| C10606 (B) | 12.10 | 4.70 | 28.79 | 17.43 |
| C20606 (B) | 11.60 | 7.20 | 26.26 | 13.83 |
| C30606 (B) | 8.20 | 4.18 | 17.12 | 10.22 |
| C40606 (B) | 2.67 | 2.76 | 1.85 | 2.90 |

FIG. 26A

METHODS FOR THE PREPARATION OF BIOLOGICALLY ACTIVE COMPOUNDS IN NANOPARTICULATE FORM

RELATED APPLICATIONS

This application is a continuation of U.S. application Ser. No. 14/461,594, filed Aug. 18, 2014, which is a continuation of U.S. application Ser. No. 12/306,948, filed Dec. 7, 2009, which is a U.S. national stage under 35 USC § 371 of International Application Number PCT/AU07/00910, filed Jun. 29, 2007, which claims priority to AU Application No. 2006903527, filed Jun. 30, 2006 and U.S. Provisional Application No. 60/915,955, filed May 4, 2007, the entire contents of which applications are hereby incorporated by reference.

FIELD OF THE INVENTION

The present invention relates to methods for the preparation of biologically active compounds in nanoparticulate form. The invention also relates to biologically active compounds in nanoparticulate form produced by said methods, to compositions comprising such compounds, to medicaments produced using said biologically active compounds in nanoparticulate form and/or compositions, and to methods of treatment of an animal, including man, using a therapeutically effective amount of said biologically active compounds administered by way of said medicaments.

BACKGROUND

Poor bioavailability is a significant problem encountered in the development of therapeutic compositions, particularly those compounds containing a biologically active compound that is poorly soluble in water at physiological pH. An active compound's bioavailability is the degree to which the active compound becomes available to the target tissue in the body after systemic administration through, for example, oral or intravenous means. Many factors affect bioavailability, including the form of dosage and the solubility and dissolution rate of the active compound.

Poorly and slowly water-soluble compounds tend to be eliminated from the gastrointestinal tract before being absorbed into the circulation. In addition, poorly soluble active agents tend to be disfavored or even unsafe for intravenous administration due to the risk of particles of agent blocking blood flow through capillaries.

It is known that the rate of dissolution of a particulate drug will increase with increasing surface area. One way of increasing surface area is decreasing particle size. Consequently, methods of making finely divided or sized drugs have been studied with a view to controlling the size and size range of drug particles for pharmaceutical compositions.

For example, dry milling techniques have been used to reduce particle size and hence influence drug absorption. However, in conventional dry milling the limit of fineness is reached generally in the region of about 100 microns (100,000 nm), at which point material cakes on the milling chamber and prevents any further diminution of particle size. Alternatively, wet grinding may be employed to reduce particle size, but flocculation restricts the lower particle size limit to approximately 10 microns (10,000 nm). The wet milling process, however, is prone to contamination, thereby leading to a bias in the pharmaceutical art against wet milling. Another alternative milling technique, commercial airjet milling, has provided particles ranging in average size from as low as about 1 to about 50 microns (1,000-50,000 nm).

There are several approaches currently used to formulate poorly soluble active agents. One approach is to prepare the active agent as a soluble salt. Where this approach cannot be employed, alternate (usually physical) approaches are employed to improve the solubility of the active agent. Alternate approaches generally subject the active agent to physical conditions that change the agent's physical and or chemical properties to improve its solubility. These include process technologies such as micro-ionisation, modification of crystal or polymorphic structure, development of oil based solutions, use of co-solvents, surface stabilizers or complexing agents, micro-emulsions, super critical fluid and production of solid dispersions or solutions. More than one of these processes may be used in combination to improve formulation of a particular therapeutic compound.

These techniques for preparing such pharmaceutical compositions tend to be complex. By way of example, a principal technical difficulty encountered with emulsion polymerization is the removal of contaminants, such as unreacted monomers or initiators (which may have undesirable levels of toxicity), at the end of the manufacturing process.

Another method of providing reduced particle size is the formation of pharmaceutical drug microcapsules, which techniques include micronizing, polymerisation and co-dispersion. However, these techniques suffer from a number of disadvantages including at least the inability to produce sufficiently small particles such as those obtained by milling, and the presence of co-solvents and/or contaminants such as toxic monomers which are difficult to remove, leading to expensive manufacturing processes.

Over the last decade, intense scientific investigation has been carried out to improving the solubility of active agents by converting the agents to ultra fine powders by methods such as milling and grinding. These techniques may be used to increase the dissolution rate of a particulate solid by increasing the overall surface area and decreasing the average particle size.

U.S. Pat. No. 6,634,576 discloses examples of wet-milling a solid substrate, such as a pharmaceutically active compound, to produce a "synergetic co-mixture".

International Patent Application PCT/AU2005/001977 (Nanoparticle Composition(s) and Method for Synthesis Thereof) describes, inter alia, a method comprising the step of contacting a precursor compound with a co-reactant under mechanochemical synthesis conditions wherein a solid-state chemical reaction between the precursor compound and the co-reactant produces therapeutically active nanoparticles dispersed in a carrier matrix. Mechanochemical synthesis, as discussed in International Patent Application PCT/AU2005/001977, refers to the use of mechanical energy to activate, initiate or promote a chemical reaction, a crystal structure transformation or a phase change in a material or a mixture of materials, for example by agitating a reaction mixture in the presence of a milling media to transfer mechanical energy to the reaction mixture, and includes without limitation "mechanochemical activation", "mechanochemical processing", "reactive milling", and related processes.

The present invention provides methods for the preparation of biologically active compounds in nanoparticulate form, which ameliorate some of the problems attendant with prior technologies, or provides an alternative thereto.

As an example of the need for such novel compounds and methods for synthesizing them, consider osteoporosis. Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax™ (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

A number of structurally unrelated compounds are capable of interacting with the estrogen receptor and producing unique in vivo profiles. Compounds with in vivo profiles typical of a "pure" antagonist (for example, ICI 164,384) or of a relatively "pure" agonist (for example, 17β-estradiol) represent opposite ends of a spectrum in this classification. Between these two extremes lie the SERMs ("selective estrogen receptor modulator"), characterized by clinical and/or preclinical selectivity as full or partial agonists in certain desired tissues (for example, bone), and antagonists or minimal agonists in reproductive tissues. Within this pharmacologic class, individual SERMs may be further differentiated based on profiles of activity in reproductive tissues.

Raloxifene, a second generation SERM, displays potentially useful selectivity in uterine tissue with apparent advantages over triphenylethylene-based estrogen receptor ligands. As such, raloxifene appears to be well-suited at least for the treatment of postmenopausal complications, including osteoporosis and cardiovascular disease. It is anticipated that, as further advances are made in the pharmacology and molecular biology of estrogen receptor active agents, further subclassifications of SERMs may evolve in the future along with an increased understanding of the therapeutic utility of these novel classes of estrogenic compounds.

The advancement of raloxifene has been hampered by its physical characteristics, particularly low solubility, which affects bioavailability. Accordingly, any improvement in the physical characteristics of raloxifene would potentially offer more beneficial therapies. In particular, it would be a significant contribution to the art to provide forms of raloxifene which have increased solubility, methods of preparation of such forms, pharmaceutical formulations comprising such forms, and methods of use of such formulations.

Although the background to the present invention is discussed in the context of improving the bioavailability of compounds that are poorly or slowly water soluble, the applications of the methods of the present invention are not limited to such, as is evident from the following description of the invention.

Further, although the background to the present invention is largely discussed in the context of improving the bioavailability of therapeutic or pharmaceutical compounds, the applications of the methods of the present invention are clearly not limited to such. For example, as is evident from the following description, applications of the methods of the present invention include but are not limited to: veterinary therapeutic applications and agricultural chemical applications, such as pesticide and herbicide applications.

SUMMARY OF THE INVENTION

The present invention is directed to the unexpected discovery that biologically active compounds in nanoparticulate form can be produced by dry milling solid biologically active compound together with a millable grinding compound, such that the resulting nanoparticulate biologically active compound dispersed in milled grinding compound resists reagglomeration.

Thus, in one aspect, the present invention comprises a method for producing a biologically active compound in nanoparticulate form, the method comprising the step of:

dry milling a mixture of a solid biologically active compound and a millable grinding compound, in a mill comprising a plurality of milling bodies, to produce a solid dispersion or solution comprising nanoparticulate biologically active compound dispersed in at least partially milled grinding compound.

The term millable means that the grinding compound is capable of being physically degraded under the dry milling conditions of the method of the invention. In one embodiment of the invention, the milled grinding compound is of a comparable particle size to the nanoparticulate biologically active compound.

Without wishing to be bound by theory, it is believed that the physical degradation of the millable grinding compound affords the advantage of the invention by acting as a more effective diluent than grinding compounds of a larger particle size.

In a highly preferred form, the grinding compound is harder than the biologically active compound, and is thus capable of physically degrading such under the dry milling conditions of the invention. Again without wishing to be bound by theory, under these circumstances it is believed that the millable grinding compound affords the advantage of the present invention through a second route, with the smaller particles of grinding compound produced under the dry milling conditions enabling the production of smaller particles of biologically active compound.

The solid dispersion or solution may then be separated from the milling bodies and removed from the mill.

In a preferred aspect, the grinding compound is separated from the dispersion or solution. In one aspect, where the grinding compound is not fully milled, the unmilled grinding compound is separated from the nanoparticulate biologically active compound. In a further aspect, at least a portion of the milled grinding compound is separated from the nanoparticulate biologically active compound.

The milling bodies are essentially resistant to fracture and erosion in the dry milling process.

The quantity of the grinding compound relative to the quantity of biologically active compound in nanoparticulate form, and the extent of physical degradation of the grinding compound, is sufficient to inhibit reagglomeration of the biologically active compound in nanoparticulate form. The grinding compound is not chemically reactive with the pharmaceutical compound under the milling conditions of the invention.

In additional aspects, the present invention also relates to biologically active compounds in nanoparticulate form produced by said methods, to compositions comprising said compounds, to medicaments produced using said biologically active compounds in nanoparticulate form and/or said compositions, and to methods of treatment of an animal, including man, using a therapeutically effective amount of said biologically active compounds administered by way of said medicaments.

Medicaments of the invention may comprise only the biologically active compounds in nanoparticulate form or, more preferably, the biologically active compounds in nanoparticulate form may be combined with one or more pharmaceutically acceptable carriers, as well as any desired excipients or other like agents commonly used in the preparation of medicaments.

While the method of the present invention has particular application in the preparation of poorly water-soluble biologically active compounds in nanoparticulate form, the scope of the invention is not limited thereto. For example, the method of the present invention enables production of highly water-soluble biologically active compounds in nanoparticulate form. Such compounds may exhibit advantages over conventional compounds by way of, for example, more rapid therapeutic action or lower dose. In contrast, wet grinding techniques utilizing water (or other comparably polar solvents) are incapable of being applied to such compounds, as the particles dissolve appreciably in the solvent.

As will be described subsequently, selection of an appropriate grinding compound affords particular highly advantageous applications of the method of the present invention. Some grinding compounds appropriate for use in the invention are readily separable from the biologically active compound in nanoparticulate form by methods not dependent on particle size (such methods being inappropriate due to the degradation of the grinding compound). For example, selecting an appropriate grinding compound that also possesses solubility properties different from the biologically active compound in nanoparticulate form allows separation of the two by relatively straightforward selective dissolution techniques. Examples of such grinding compounds are provided in the detailed description of the invention. Thus, a particularly advantageous application of the method of the invention is the use of a water-soluble salt as a grinding compound in conjunction with a poorly water-soluble biologically active compound.

Again, as will be described subsequently, a highly advantageous aspect of the present invention is that certain grinding compounds appropriate for use in the method of the invention are also appropriate for use in a medicament. The present invention encompasses methods for the production of a medicament incorporating both the biologically active compound in nanoparticulate form and at least a portion of the grinding compound, medicaments so produced, and methods of treatment of an animal, including man, using a therapeutically effective amount of said biologically active compounds by way of said medicaments.

Analogously, as will be described subsequently, a highly advantageous aspect of the present invention is that certain grinding compounds appropriate for use in the method of the invention are also appropriate for use in a carrier for an agricultural chemical, such as a pesticide or a herbicide. The present invention encompasses methods for the production of an agricultural chemical composition incorporating both the biologically active compound in nanoparticulate form and at least a portion of the grinding compound, and agricultural chemical compositions so produced.

The agricultural chemical compound may include only the biologically active compound in nanoparticulate form together with the milled grinding compound or, more preferably, the biologically active compounds in nanoparticulate form and milled grinding compound may be combined with one or more pharmaceutically acceptable carriers, as well as any desired excipients or other like agents commonly used in the preparation of medicaments.

Analogously, the agricultural chemical composition may include only the biologically active compound in nanoparticulate form together with the milled grinding compound or, more preferably, the biologically active compounds in nanoparticulate form and milled grinding compound may be combined with one or more carriers, as well as any desired excipients or other like agents commonly used in the preparation of agricultural chemical compositions.

In one particular form of the invention, the grinding compound is both appropriate for use in a medicament and readily separable from the biologically active compound in nanoparticulate form by methods not dependent on particle size. Such grinding compounds are described in the following detailed description of the invention. Such grinding compounds are highly advantageous in that they afford significant flexibility in the extent to which the grinding compound may be incorporated with the biologically active compound in nanoparticulate form into a medicament.

In one aspect, the invention provides novel formulations of raloxifene. Raloxifene is [6-hydroxy-2-(4-hydroxyphenyl)benzol[b]thien-3-yl][4-[2-(1-piperidinyl)ethoxy]phenyl-, and is also known as 6-hydroxy-2-(4-hydrophenyl)-3-[4-(2-piperidinoethoxy)-benzoyl]benzo-[b]-thiophene. Other names for raloxifene may also be found in the literature. The structural formula for raloxifene is illustrated below:

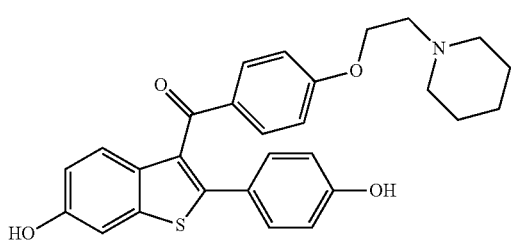 [SMILES: O=C(c1ccc(OCCN2CCCCC2)cc1)c1c(-c2ccc(O)cc2)sc2cc(O)ccc12]

This invention provides raloxifene, or a pharmaceutically acceptable salt or solvate thereof, in particulate form having a mean particle size of between about 10 nm and about 500 nm.

The invention further provides methods for producing said particulate raloxifene, pharmaceutically acceptable salt or solvate thereof.

The invention also provides pharmaceutical compositions comprising or formulated using the said particulate raloxifene, or pharmaceutically acceptable salt or solvate thereof.

The present invention further provides the use of the said particulate raloxifene, or pharmaceutically acceptable salt or solvate thereof, in the manufacture of a pharmaceutical composition for alleviating human pathologies, including osteoporosis, serum lipid lowering, and inhibiting endometriosis, uterine fibrosis, and breast cancer.

The present invention further provides the use of such compositions comprising or formulated using the said raloxifene, or pharmaceutically acceptable salt or solvate thereof, for alleviating human pathologies, including osteoporosis, serum lipid lowering, and inhibiting endometriosis, uterine fibrosis, and breast cancer.

In one aspect, then, the invention provides a method for producing a composition comprising nanoparticles of a biologically active compound, the method comprising the step of:

dry milling a solid biologically active compound and a millable grinding compound in a mill comprising a plurality of milling bodies, for a time period sufficient to produce a solid dispersion comprising nanoparticles of the biologically active compound dispersed in at least partially milled grinding compound. A pharmaceutically acceptable carrier may also be combined with such composition to produce a pharmaceutical composition, or a medicament.

In another aspect, the nanoparticles have an average size less than 1000 nm, less than 500 nm, less than 350 nm, less than 200 nm, less than 100 nm, less than 75 nm, less than 50 nm, or less than 40 nm. The particle size of at least 50%, or 75%, of the nanoparticles may be within the average size range.

The time period for the milling operation is preferably between 5 minutes and 8 hours, more preferably between 5 minutes and 2 hours, more preferably between 5 minutes and 4 hours, preferably between 5 and 45 minutes, more preferably between 5 and 30 minutes, most preferably between 10 and 25 minutes.

In another aspect of this invention, the milling medium is selected from the group consisting of ceramics, glasses, polymers, ferromagnetics, and metals, such as steel balls, which may have a diameter of between 1 and 20 mm, preferably between 2 and 15 mm, more preferably between 3 and 10 mm.

The method of the invention is suitable for milling biologically active compounds, such as biologics, amino acids, proteins, peptides, nucleotides, nucleic acids, and analogs homologs and first order derivatives thereof. Many drugs are amenable to the methods of the invention, including but not limited to diclofenac, olanzapine, sildenafil, raloxifene, and others.

In another aspect, the method further comprises the step of removing at least a portion of the at least partially milled grinding compound.

The invention also provides a nanoparticle composition comprising nanoparticles of a biologically active compound, formed by the process of dry milling a solid biologically active compound and a millable grinding compound in a mill comprising a plurality of milling bodies, for a time period sufficient to produce a solid dispersion comprising nanoparticles of the biologically active compound dispersed in at least partially milled grinding compound. Such nanoparticle compositions may have the same particle size ranges as aforementioned. Likewise, the process may further comprise removing at least a portion of the at least partially milled grinding compound.

In another aspect, the invention provides a method of treating a human in need of such treatment comprising the step of administering to such human a pharmaceutically effective amount of a nanoparticle composition, a pharmaceutical composition, or a medicament as described above.

Other aspects and advantages of the invention will become apparent to those skilled in the art from a review of the ensuing description.

BRIEF DESCRIPTION OF THE DRAWINGS

FIG. 19 shows the structures of ionic surfactants utilized in some embodiments of the method of the invention;

FIG. 20 is a scanning electron micrograph of particulate raloxifene (free base) according to an embodiment of the invention;

FIG. 25 provides mean pharmacokinetic data in tabular form; and

DETAILED DESCRIPTION OF THE INVENTION

General

Figure 1:
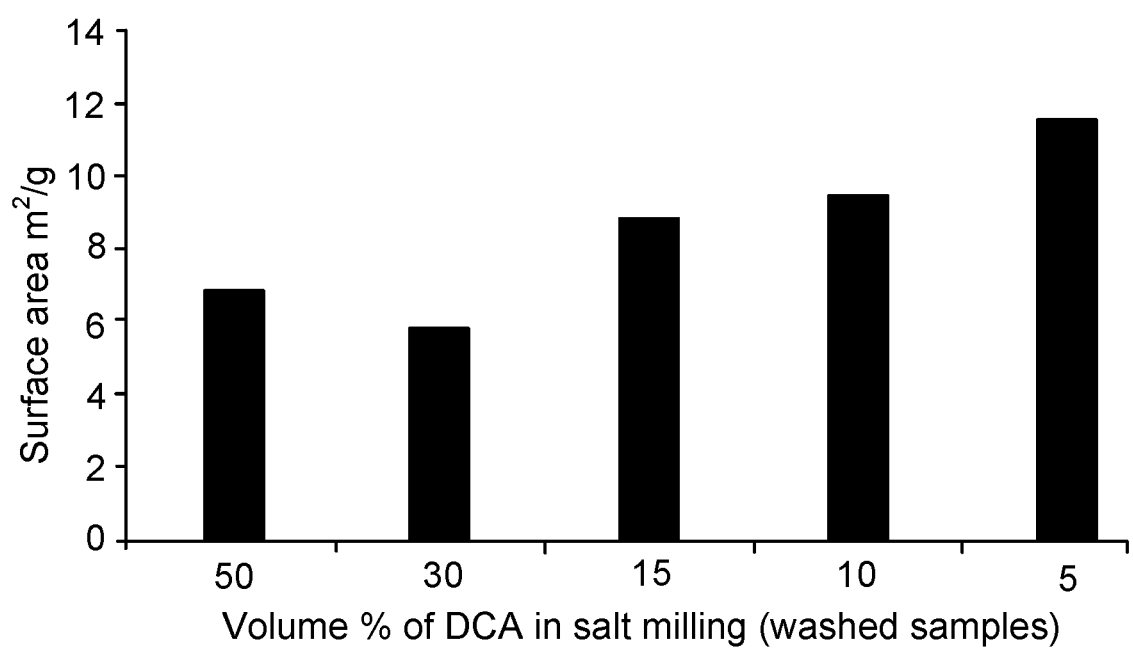
FIG. 1 shows that with decreasing volume percentage of diclofenac acid in NaCl grinding compound, the surface area of the diclofenac nanoparticles increases (nanoparticles after removal of grinding compound by washing)

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The invention described herein may include one or more ranges of values (e.g. size, concentration etc). A range of values will be understood to include all values within the range, including the values defining the range, and values adjacent to the range that lead to the same or substantially the same outcome as the values immediately adjacent to that value which defines the boundary to the range.

The entire disclosures of all publications (including patents, patent applications, journal articles, laboratory manuals, books, or other documents) cited herein are hereby incorporated by reference. Inclusion does not constitute an admission is made that any of the references constitute prior art or are part of the common general knowledge of those working in the field to which this invention relates.

Throughout this specification, unless the context requires otherwise, the word "comprise" or variations, such as "comprises" or "comprising" will be understood to imply the inclusion of a stated integer, or group of integers, but not the exclusion of any other integers or group of integers. It is also noted that in this disclosure, and particularly in the claims and/or paragraphs, terms such as "comprises", "comprised", "comprising" and the like can have the meaning attributed to it in US Patent law; e.g., they can mean "includes", "included", "including", and the like.

"Therapeutically effective amount" as used herein with respect to methods of treatment and in particular drug dosage, shall mean that dosage that provides the specific pharmacological response for which the drug is administered in a significant number of subjects in need of such treatment. It is emphasized that "therapeutically effective amount," administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug levels as measured in blood.

The term "inhibit" is defined to include its generally accepted meaning which includes prohibiting, preventing, restraining, and lowering, stopping, or reversing progression or severity, and such action on a resultant symptom. As such the present invention includes both medical therapeutic and prophylactic administration, as appropriate.

The term "mean particle size" is defined as equivalent spherical diameter as determined by laser light diffraction scattering.

Because the particles in the raw state as well as after milling or other particle size reduction techniques are irregular in shape, it is necessary to characterize them not by measurement of an actual size such as thickness or length, but by measurement of a property of the particles which is related to the sample property possessed by a theoretical spherical particle. The particles are thus allocated an "equivalent spherical diameter".

The values found from characterizing a large number of "unknown" particles can be plotted frequency vs. diameter or in other methods weight vs. diameter, usually adopting percentage undersize values for frequency or weight. This gives a characteristic curve representing size distribution of the sample, i.e., cumulative percentage undersize distribution curve. Values from this can be read off directly or plotted on log-probability paper to give an appropriate straight line. The mean equivalent spherical volume diameter is the 50% undersize value.

Methods of determining particle sizes are known in the art, and the method by which the particle sizes of the raloxifene hydrochloride of the present invention are measured is described herein. However, other methods may be employed—see, for example, the methods described in U.S. Pat. No. 4,605,517 (Riley et al.).

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 400 nm" it is meant that at least 90% of the particles have a number average particle size of less than about 400 nm when measured by the above-noted techniques.

As used herein, the term "effective mean particle diameter" is defined as the mean diameter of the smallest circular hole through which a particle can pass freely. For example, the effective mean particle diameter of a spherical particle corresponds to the mean particle diameter and the effective mean particle diameter of an ellipsoidal particle corresponds to the mean length of the longest minor axis.

Throughout this specification, unless the context requires otherwise, the term "solvate" is used to describe an aggregate that comprises one or more molecules of the solute, such as raloxifene, with one or more molecules of solvent.

Throughout this specification, unless the context requires otherwise, the term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

The pharmaceutically acceptable acid addition salts are typically formed by reacting raloxifene with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means.

Throughout this specification, unless the context requires otherwise, the phrase "dry mill" or variations, such as "dry milling", should be understood to refer to milling in at least the substantial absence of liquids. If liquids are present, they are present in such amounts that the contents of the mill retain the characteristics of a paste or, preferably, a dry powder.

"Flowable" means a powder having physical characteristics rendering it suitable for an automatic or semi-automatic manufacturing process as, for example, would be used for the manufacture of pharmaceutical compositions and formulations.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Throughout this specification, unless the context requires otherwise, the term "nanoparticulate form" includes nanoparticle compositions, wherein the composition comprises at least nanoparticles having an average particle size smaller than 1000 nm.

"Conventional" in the context of the form of biologically active compounds, agents or drugs refers to non-nanoparticulate compositions. Non-nanoparticulate active agents have an effective average particle size of greater than about 2 microns, meaning that at least 50% of the active agent particles have a size greater than about 2 microns.

A "solid solution" consists of one phase only, irrespective of the number of differing components present. A solid solution may be classified as continuous, discontinuous, substitutional, interstitial or amorphous. Typical solid solutions have a crystalline structure, in which the solute molecules can either substitute for solvent molecules in the crystal lattice or fit into the interstices between the solvent molecules. Interstitial crystalline solid solutions occur when the dissolved molecules occupy the interstitial spaces between the solvent molecules in the crystal lattice. Amorphous solid solutions occur when the solute molecules are dispersed molecularly but irregularly within the amorphous solvent.

The term "a solid dispersion" in general means a system in solid state comprising at least two components, wherein one component is dispersed more or less evenly throughout the other component or components.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Specific

In one embodiment, the present invention is directed to a method for producing for the preparation of a biologically active compound in nanoparticulate form, the method comprising the step of:

dry milling a mixture of a solid biologically active compound and a millable grinding compound, in a mill comprising a plurality of milling bodies, to produce a solid dispersion or solution comprising nanoparticulate biologically active compound dispersed in at least partially milled grinding compound.

The solid dispersion or solution may then be separated from the milling bodies and removed from the mill.

In one aspect, the grinding compound is separated from the dispersion or solution. In one aspect, where the grinding compound is not fully milled, the unmilled grinding compound is separated from the nanoparticulate biologically active compound. In a further aspect, at least a portion of the milled grinding compound is separated from the nanoparticulate biologically active compound.

The milling bodies are essentially resistant to fracture and erosion in the dry milling process. The quantity of the grinding compound relative to the quantity of biologically active compound in nanoparticulate form, and the extent of milling of the grinding compound, is sufficient to inhibit reagglomeration of the biologically active compound in nanoparticulate form.

The grinding compound is neither chemically nor mechanically reactive with the pharmaceutical compound under the conditions present in the process of the invention.

The present invention also relates to biologically active compounds in nanoparticulate form produced by said methods, to medicaments produced using said biologically active compounds in nanoparticulate form and to methods of treatment of an animal, including man, using a therapeutically effective amount of said biologically active compounds administered by way of said medicaments.

Grinding Compound

As stated above, the method of the present invention requires the grinding compound to be milled with the pharmaceutical compound; that is, the grinding compound will physically degrade under the dry milling conditions of the invention to facilitate the formation and retention of the biologically active compound in nanoparticulate form. The precise extent of degradation required will depend on certain properties of the grinding compound and the biologically active compound (for example, any charge distribution or surface effects causing the grinding compound to have a greater or lesser affinity for the biologically active compound), the ratio of biologically active compound to grinding compound, and the desired particle size and particle size distribution of the nanoparticles comprising the biologically active compound in nanoparticulate form.

In one embodiment of the invention, the milled grinding compound is of a comparable particle size to the nanoparticulate biologically active compound.

The physical properties of the grinding compound necessary to achieve the requisite degradation are dependant on the precise milling conditions. For example a harder grinding compound may degrade to a sufficient extent provided under more vigorous dry milling conditions.

Physical properties of the grinding compound relevant to the extent that the agent will degrade under dry milling conditions include hardness, friability, as measured by indicia such as fracture toughness and brittleness index.

A low hardness (typically a Mohs Hardness less than 7) of the biologically active compound is desirable to ensure fracture of the particles during processing, so that nanocomposite microstructures develop during milling.

Preferably, the grinding compound is of low abrasivity. Low abrasivity is desirable to minimise contamination of the dispersion or solution of the biologically active compound in nanoparticulate form in the grinding compound by the milling bodies and/or the milling chamber of the media mill. An indirect indication of the abrasivity can be obtained by measuring the level of milling-based contaminants.

Preferably, the grinding compound has a low tendency to agglomerate during dry milling. While it is difficult to objectively quantify the tendency to agglomerate during milling, it is possible to obtain a subjective measure by observing the level of "caking" of the grinding compound on the milling bodies and the milling chamber of the media mill as dry milling progresses.

The grinding compound may be an inorganic or organic compound. In one embodiment, the grinding compound is selected from the following: sodium hydrogen sulfate, sodium hydrogen carbonate, sodium hydroxide, or succinic acid; crystalline organic acids, for example (but not limited to) fumaric acid, maleic acid, tartaric acid, citric acid); alternatively ammonium salts (or salts of volatile amines), for example (but not limited to) ammonium chloride, methylamine hydrochloride, ammonium bromide, crystalline hydroxides, hydrogen carbonates, hydrogen carbonates of pharmaceutical acceptable alkali metals, such as but not limited by, sodium, potassium, lithium, calcium, and barium, sodium sulphate, sodium chloride, sodium metabisulphite, sodium thiosulphate, ammonium chloride, Glauber's salt, ammonium carbonate, sodium bisulphate, magnesium sulphate, potash alum, potassium chloride, sodium carbonate, sodium bicarbonate, potassium carbonate, potassium bicarbonate.

In a preferred embodiment, the grinding compound is a compound that is considered GRAS (generally regarded as safe) by persons skilled in the pharmaceutical arts.

Relative Quantity of Grinding Compound

The quantity of the grinding compound relative to the quantity of biologically active compound in nanoparticulate form and the extent of degradation of the grinding compound, determine whether reagglomeration of the biologically active compound in nanoparticulate form is at least inhibited.

Further, the extent of degradation of the grinding compound under the dry milling conditions of the invention may affect the quantity of grinding compound required to produce the biologically active compound in nanoparticulate form, such that grinding compounds that degrade to a greater extent are required in smaller relative quantities.

For example, it may be possible for the volume fraction of the nanoparticles comprising the biologically active compound in nanoparticulate form to be greater than the theoretical percolation threshold, which, for 3-dimensional random dispersions of spherical particles, is around 15 vol %. In a preferred form of the invention, the volume fraction of the nanoparticles comprising the biologically active compound in nanoparticulate form is less than about 25 vol %. More preferably, the volume fraction of the nanoparticles comprising the biologically active compound in nanoparticulate form is less than about 20 vol %. In a highly preferred form of the invention, the volume fraction of the nanoparticles comprising the biologically active compound in nanoparticulate form is less than about 15 vol %.

Milling Bodies

In the method of the present invention, the milling bodies are preferably chemically inert and rigid. The term "chemically-inert", as used herein, means that the milling bodies do not react chemically with the biologically active compound or the grinding compound.

As described above, the milling bodies are essentially resistant to fracture and erosion in the milling process.

The milling bodies are desirably provided in the form of bodies which may have any of a variety of smooth, regular shapes, flat or curved surfaces, and lacking sharp or raised edges. For example, suitable milling bodies can be in the form of bodies having ellipsoidal, ovoid, spherical or right cylindrical shapes. Preferably, the milling bodies are provided in the form of one or more of beads, balls, spheres, rods, right cylinders, drums or radius-end right cylinders (i.e., right cylinders having hemispherical bases with the same radius as the cylinder).

Depending on the nature of the biologically active compound substrate and the grinding compound, the milling media bodies desirably have an effective mean particle diameter (i.e. "particle size") between about 0.1 and 30 mm, more preferably between about 1 and about 15 mm, still more preferably between about 3 and 10 mm.

The milling bodies may comprise various materials such as ceramic, glass, metal or polymeric compositions, in a particulate form. Suitable metal milling bodies are typically spherical and generally have good hardness (i.e. RHC 60-70), roundness, high wear resistance, and narrow size distribution and can include, for example, balls fabricated from type 52100 chrome steel, type 316 or 440C stainless steel or type 1065 high carbon steel.

Preferred ceramic materials, for example, can be selected from a wide array of ceramics desirably having sufficient hardness and resistance to fracture to enable them to avoid being chipped or crushed during milling and also having sufficiently high density. Suitable densities for milling media can range from about 1 to 15 g/cm$^3$. Preferred ceramic materials can be selected from steatite, aluminum oxide, zirconium oxide, zirconia-silica, yttria-stabilized zirconium oxide, magnesia-stabilized zirconium oxide, silicon nitride, silicon carbide, cobalt-stabilized tungsten carbide, and the like, as well as mixtures thereof.

Preferred glass milling media are spherical (e.g. beads), have a narrow size distribution, are durable, and include, for example, lead-free soda lime glass and borosilicate glass. Polymeric milling media are preferably substantially spherical and can be selected from a wide array of polymeric resins having sufficient hardness and friability to enable them to avoid being chipped or crushed during milling, abrasion-resistance to minimize attrition resulting in contamination of the product, and freedom from impurities such as metals, solvents, and residual monomers.

Preferred polymeric resins, for example, can be selected from crosslinked polystyrenes, such as polystyrene cross-linked with divinylbenzene, styrene copolymers, polyacrylates such as polymethylmethacrylate, polycarbonates, polyacetals, vinyl chloride polymers and copolymers, polyurethanes, polyamides, high density polyethylenes, polypropylenes, and the like. The use of polymeric milling media to grind materials down to a very small particle size (as opposed to mechanochemical synthesis) is disclosed, for example, in U.S. Pat. Nos. 5,478,705 and 5,500,331. Polymeric resins typically can have densities ranging from about 0.8 to 3.0 g/cm$^3$. Higher density polymeric resins are preferred. Alternatively, the milling media can be composite particles comprising dense core particles having a polymeric resin adhered thereon. Core particles can be selected from materials known to be useful as milling media, for example, glass, alumina, zirconia silica, zirconium oxide, stainless steel, and the like. Preferred core materials have densities greater than about 2.5 g/cm$^3$.

In one embodiment of the invention, the milling media are formed from a ferromagnetic material, thereby facilitating removal of contaminants arising from wear of the milling media by the use of magnetic separation techniques.

Each type of milling body has its own advantages. For example, metals have the highest specific gravities, which increase grinding efficiency due to increased impact energy. Metal costs range from low to high, but metal contamination of final product can be an issue. Glasses are advantageous from the standpoint of low cost and the availability of small bead sizes as low as 0.004 mm. However, the specific gravity of glasses is lower than other media and significantly more milling time is required. Finally, ceramics are advantageous from the standpoint of low wear and contamination, ease of cleaning, and high hardness.

Dry Milling

In the dry milling process of the present invention, the biologically active compound substrate and grinding compound, in the form of crystals, powders, or the like, are combined in suitable proportions with the plurality of milling bodies in a milling chamber that is mechanically agitated (i.e., with or without stirring) for a predetermined period of time at a predetermined intensity of agitation. Typically, a milling apparatus is used to impart motion to the milling bodies by the external application of agitation, whereby various translational, rotational or inversion motions or combinations thereof are applied to the milling chamber and its contents, or by the internal application of agitation through a rotating shaft terminating in a blade, propeller, impeller or paddle or by a combination of both actions.

During milling, motion imparted to the milling bodies can result in application of shearing forces as well as multiple impacts or collisions having significant intensity between milling bodies and particles of the reactant powders. The nature and intensity of the forces applied by the milling bodies to the biologically active compound and the grinding compound is influenced by a wide variety of processing parameters including: the type of milling apparatus; the intensity of the forces generated, the kinematic aspects of the process; the size, density, shape, and composition of the milling bodies; the weight ratio of the biologically active compound and grinding compound mixture to the milling bodies; the duration of milling; the physical properties of both the biologically active compound and the grinding compound; the atmosphere present during activation; and others.

Advantageously, the media mill is capable of repeatedly or continuously applying mechanical compressive forces and shear stress to the biologically active compound substrate and the grinding compound. Suitable media mills include but are not limited to the following: high-energy ball, sand, bead or pearl mills, basket mill, planetary mill, vibratory action ball mill, multi-axial shaker/mixer, stirred ball mill, horizontal small media mill, multi-ring pulverizing mill, and the like, including small milling media. The milling apparatus also can contain one or more rotating shafts.

In a preferred form of the invention, the dry milling is effected a ball mill. Throughout the remainder of the specification reference will be made to dry milling being carried out by way of a ball mill. Examples of this type of mill are attritor mills, nutating mills, tower mills, planetary mills, vibratory mills and gravity-dependent-type ball mills. It will be appreciated that dry milling in accordance with the method of the invention may also be achieved by any suitable means other than ball milling. For example, dry milling may also be achieved using jet mills, rod mills, roller mills or crusher mills.

Biologically Active Compound

The biologically active compound includes therapeutically active compounds, including compounds for veterinary and human use, and agricultural compounds such as pesticides, herbicides and fungicides, germinating agents and the like.

In a preferred form of the invention, the biologically active compound is an organic compound. In a highly preferred form of the invention, the biologically active compound is an organic, therapeutically active compounds for veterinary or human use. In a highly preferred form of the invention, the biologically active compound is an organic, therapeutically active compounds for human use.

The biologically active compound substrate is ordinarily a compound for which one of skill in the art desires improved properties arising from smaller particle sizes. The biologically active compound substrate may be a conventional active agent or drug, although the process of the invention may be employed on formulations or agents that already have reduced particle size compared to their conventional form.

Biologically active compounds suitable for use in the invention include biologics, amino acids, proteins, peptides, nucleotides, nucleic acids, and analogs, homologs and first order derivatives thereof. The biologically active compound can be selected from a variety of known classes of drugs, including, but not limited to: anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, cough suppressants (expectorants and mucolytics), diagnostic agents, diagnostic imaging agents, diuretics, dopaminergics (anti-Parkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

A description of these classes of active agents and a listing of species within each class can be found in Martindale's The Extra Pharmacopoeia, 31st Edition (The Pharmaceutical Press, London, 1996), specifically incorporated by reference. Another source of active agents is the Physicians Desk Reference (60$^{th}$ Ed., pub. 2005), familiar to those of skill in the art. The active agents are commercially available and/or can be prepared by techniques known in the art.

An exhaustive list of drugs for which the methods of the invention are suitable would be burdensomely long for this specification; however, reference to the general pharmacopoeia listed above would allow one of skill in the art to select virtually any drug to which the method of the invention may be applied.

Notwithstanding the general applicability of the method of the invention, more specific examples of biologically active compounds include, but are not limited to: haloperidol (dopamine antagonist), DL isoproterenol hydrochloride (β-adrenergic agonist), terfenadine (H1-antagonist), propranolol hydrochloride (β-adrenergic antagonist), desipramine hydrochloride (antidepressant), salmeterol (b2-selective adrenergic agonist), sildenafil citrate, tadalafil and vardenafil. Minor analgesics (cyclooxygenase inhibitors), fenamic acids, Piroxicam, Cox-2 inhibitors, and Naproxen, and others, may all benefit from being prepared in a nanoparticulate form.

As discussed in the context of the background to the invention, biologically active compounds that are poorly water soluble at physiological pH will particularly benefit from being prepared in nanoparticulate form, and the method of the present invention is particularly advantageously applied to compounds that are poorly water soluble at physiological pH.

Such compounds include, but are not limited to: albendazole, albendazole sulfoxide, alfaxalone, acetyl digoxin, acyclovir analogs, alprostadil, aminofostin, anipamil, antithrombin III, atenolol, azidothymidine, beclobrate, beclomethasone, belomycin, benzocaine and derivatives, beta carotene, beta endorphin, beta interferon, bezafibrate, binovum, biperiden, bromazepam, bromocryptine, bucindolol, buflomedil, bupivacaine, busulfan, cadralazine, camptothesin, canthaxanthin, captopril, carbamazepine, carboprost, cefalexin, cefalotin, cefamandole, cefazedone, cefluoroxime, cefinenoxime, cefoperazone, cefotaxime, cefoxitin, cefsulodin, ceftizoxime, chlorambucil, chromoglycinic acid, ciclonicate, ciglitazone, clonidine, cortexolone, corticosterone, cortisol, cortisone, cyclophosphamide, cyclosporin A and other cyclosporins, cytarabine, desocryptin, desogestrel, dexamethasone esters such as the acetate, dezocine, diazepam, diclofenac, dideoxyadenosine, dideoxyinosine, digitoxin, digoxin, dihydroergotamine, dihydroergotoxin, diltiazem, dopamine antagonists, doxorubicin, econazole, endralazine, enkephalin, enalapril, epoprostenol, estradiol, estramustine, etofibrate, etoposide, factor ix, factor viii, felbamate, fenbendazole, fenofibrate, fexofenedine, flunarizin, flurbiprofen, 5-fluorouracil, flurazepam, fosfomycin, fosmidomycin, furosemide, gallopamil, gamma interferon, gentamicin, gepefrine, gliclazide, glipizide, griseofulvin, haptoglobulin, hepatitis B vaccine, hydralazine, hydrochlorothiazide, hydrocortisone, ibuprofen, ibuproxam, indinavir, indomethacin, iodinated aromatic x-ray contrast agents such as iodamide, ipratropium bromide, ketoconazole, ketoprofen, ketotifen, ketotifen fumarate, K-strophanthin, labetalol, lactobacillus vaccine, lidocaine, lidoflazin, lisuride, lisuride hydrogen maleate, lorazepam, lovastatin, mefenamic acid, melphalan, memantin, mesulergin, metergoline, methotrexate, methyl digoxin, methylprednisolone, metronidazole, metisoprenol, metipranolol, metkephamide, metolazone, metoprolol, metoprolol tartrate, miconazole, miconazole nitrate, minoxidil, misonidazol, molsidomin, nadolol, nafiverine, nafazatrom, naproxen, natural insulins, nesapidil, nicardipine, nicorandil, nifedipine, niludipin, nimodipine, nitrazepam, nitrendipine, nitrocamptothesin, 9-nitrocamptothesin, olanzapine, oxazepam, oxprenolol, oxytetracycline, penicillins such as penicillin G benethamine, penecillin O, phenylbutazone, picotamide, pindolol, piposulfan, piretanide, piribedil, piroxicam, pirprofen, plasminogenici activator, prednisolone, prednisone, pregnenolone, procarbacin, procaterol, progesterone, proinsulin, propafenone, propanolol, propentofyllin, propofol, propranolol, raloxifene, rifapentin, simvastatin, semi-synthetic insulins, sobrerol, somastotine and its derivatives, somatropin, stilamine, sulfinalol hydrochloride, sulfinpyrazone, suloctidil, suprofen, sulproston, synthetic insulins, talinolol, taxol, taxotere, testosterone, testosterone propionate, testosterone undecanoate, tetracane HI, tiaramide HCl, tolmetin, tranilast, triquilar, tromantadine HCl, urokinase, valium, verapamil, vidarabine, vidarabine phosphate sodium salt, vinblastine, vinburin, vincamine, vincristine, vindesine, vinpocetine, vitamin A, vitamin E succinate, and x-ray contrast agents. Drugs can be neutral species or basic or acidic as well as salts such as exist in the presence of an aqueous buffer.

In addition, some biologically active compounds may have the benefit of absorption through the skin if presented in a nanoparticle formulation. Such biologically active compounds include, but are not limited to, Voltaren (diclofenac), rofecoxib, and ibuprofen.

Conveniently, the biologically active compound is capable of withstanding temperatures that are typical in uncooled dry milling, which may exceed 80° C. Therefore, compounds with a melting point about 80° C. or greater are suitable. For biologically active compounds with lower melting points, the media mill may be cooled, thereby allowing compounds with significantly lower melting temperatures to be processed according to the method of the invention. For instance, a simple water-cooled mill will keep temperatures below 50° C., or chilled water could be used to further lower the milling temperature. Those skilled in the art will understand that a reaction mill could be designed to run at any temperature between say −190 to 500° C. For some biologically active compounds it may be advantageous to control the milling temperature to temperatures significantly below the melting points of the biologically active compounds.

The biologically active compound substrate is obtained in a conventional form commercially and/or prepared by techniques known in the art.

It is preferred, but not essential, that the particle size of the biologically active compound substrate be less than about 100 μm, as determined by sieve analysis. If the coarse particle size of the biologically active compound substrate is greater than about 100 μm, then it is preferred that the particles of the biologically active compound substrate be reduced in size to less than 100 μm using a conventional milling method such as airjet or fragmentation milling.

Biologically Active Compound in Nanoparticulate Form

Preferably, the biologically active compound in nanoparticulate form comprises nanoparticles of biologically active compound of an average particle size diameter less than 1000 nm, preferably less than 500 nm, preferably less than 350 nm, preferably less than 200 nm, preferably less than 100 nm, preferably less than 75 nm, more preferably less than 50 nm, and in some cases less than 30 nm.

Preferably, the biologically active compound in nanoparticulate form comprises nanoparticles of biologically active compound of between about 1 nm to about 200 nm, or more preferably between about 5 nm to about 100 nm, more preferably between about 5 and 50 nm, more preferably still between about 10 nm to about 40 nm. In a highly preferred embodiment of the invention, the nanoparticles of biologically active compound are between about 20 nm and 30 nm in size. These sizes refer to nanoparticles either fully dispersed or partially agglomerated. For example, where two 20 nm particles agglomerate, the resulting entity is a nanoparticle about 40 nm in size and thus would still be considered a nanoparticle within the meaning of the invention. Stated alternatively, the nanoparticles of biologically active compound will preferably have an average size less than 200 nm, more preferably less than 100 nm, more preferably less than 75 nm, more preferably less than 50 nm, and more preferably less than 40 nm, where the average size refers to nanoparticles either fully dispersed or partially agglomerated as described above.

Preferably, the nanoparticles of the biologically active compound in nanoparticulate form are distributed in size so that at least 50% of the nanoparticles have a size within the average range, more preferably at least 60%, more preferably at least 70%, and still more preferably at least 75% of the nanoparticles have a size within the average range.

Agglomerates

Agglomerates comprising particles of biologically active compound in nanoparticulate form, said particles having a mean particle size within the ranges specified above, should be understood to fall within the scope of the present invention, regardless of whether the agglomerates exceed 1000 nm in size.

Time

Preferably, the biologically active compound substrate and the grinding compound are dry milled for the shortest time necessary to form the solid dispersion or solution of the biologically active compound in nanoparticulate form in the grinding compound to minimise any possible contamination from the media mill and/or the plurality of milling bodies. This time varies greatly, depending on the biologically active compound and the grinding compound, and may range from as short as 5 minutes to several hours. Dry milling times in excess of 2 hours may lead to degradation of the biologically active compound in nanoparticulate form and an increased level of undesirable contaminants.

Suitable rates of agitation and total milling times are adjusted for the type and size of milling apparatus as well as the milling media, the weight ratio of the substrate biologically active compound and grinding compound mixture to the plurality of milling bodies, the chemical and physical properties of the substrate biologically active compound and grinding compound, and other parameters that may be optimized empirically.

The time may range from between 5 minutes and 2 hours, 5 minutes and 1 hour, 5 minutes and 45 minutes, 5 minutes and 30 minutes, and 10 minutes and 20 minutes.

Separation of the Grinding Compound from the Biologically Active Compound in Nanoparticulate Form In one embodiment, the method further comprises the step of;

Separating at least a portion of the milled grinding compound from the biologically active compound in nanoparticulate form.

Any portion of the grinding compound may be removed, including but not limited to 10%, 25%, 50%, 75%, or substantially all of the grinding compound.

In some embodiments of the invention, a significant portion of the milled grinding compound may comprise particles of a size similar to and/or smaller than the particles comprising the biologically active compound in nanoparticulate form. Where the portion of the milled grinding compound to be separated from the particles comprising the biologically active compound in nanoparticulate form comprises particles of a size similar to and/or smaller than the particles comprising the biologically active compound in nanoparticulate form, separation techniques based on size distribution are inapplicable.

In these circumstances, the method of the present invention may involve separation of at least a portion of the milled grinding compound from the biologically active compound in nanoparticulate form by techniques including but not limited to electrostatic separation, magnetic separation, centrifugation (density separation), hydrodynamic separation, froth flotation.

Advantageously, the step of removing at least a portion of the milled grinding compound from the biologically active compound in nanoparticulate form may be performed through means such as selective dissolution, washing, or sublimation.

In one form of the invention, the grinding compound possesses solubility properties in a solvent different from the biologically active compound in nanoparticulate form and the step of removing at least a portion of the grinding compound from the biologically active compound in nanoparticulate form is performed by washing the solid dispersion or solution of the biologically active compound in nanoparticulate form in the grinding compound with the solvent.

Appropriate solvents may be acid, alkaline or neutral aqueous solutions, or an organic solvent. This may be any solvent in which the drug is insoluble but the matrix is soluble or alternatively in which the biologically active compound in nanoparticulate form and grinding compound may be separated by differential centrifugation.

As described above, appropriate grinding compound include a number of highly water soluble inorganic salts. Where the biologically active compound is poorly water soluble, a particularly appropriate grinding compound is thus a water soluble salt as this facilitates facile separation of the grinding compound from the biologically active compound in nanoparticulate form by contacting the solid solution or dispersion of the biologically active compound in nanoparticulate form in the grinding compound with water.

Examples of poorly water-soluble biologically active compounds are provided above.

Examples of water soluble inorganic salts include: sodium sulphate, sodium chloride, sodium metabisulphite, sodium thiosulphate, ammonium chloride, Glauber's salt, ammonium carbonate, sodium bisulphate, magnesium sulphate, potash alum, potassium chloride, sodium carbonate, sodium bicarbonate, potassium carbonate, potassium bicarbonate.

Preferred water soluble inorganic salts include sodium chloride, ammonium chloride, potash alum, potassium chloride, potassium bromide and sodium sulphate, especially anhydrous sodium sulphate.

In a highly convenient form of the invention, the grinding compound is sodium chloride. The sodium chloride may be provided in dendritic, granular or ordinary cubic form.

In some cases, the biologically active compound in nanoparticulate form resulting from at least partial removal of the grinding compound may require stabilization with a surface stabilizer. Example surface stabilizers include CTAB, cetyl pyridinium chloride, gelatin, casein, phosphatides, dextran, glycerol, gum acacia, cholesterol, tragacanth, stearic acid, stearic acid esters and salts, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers, poloxamines, a charged phospholipid, dimyristoyl phophatidyl glycerol, dioctylsulfosuccinate, dialkylesters of sodium sulfosuccinic acid, dioctyl sodium sulfosuccinate, sodium lauryl sulfate, alkyl aryl polyether sulfonates, mixtures of sucrose stearate and sucrose distearate, triblock copolymers of the structure: -(-PEO)-(-PBO-)-(-PEO-)-, p-isononylphenoxy-poly-(glycidol), decanoyl-N-methylglucamide; n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, octyl β-D-thioglucopyranoside, lysozyme, a PEG derivatized phospholipid, PEG derivatized cholesterol, a PEG derivatized cholesterol derivative, PEG derivatized vitamin A, PEG derivatized vitamin E, and random copolymers of vinyl acetate and vinyl pyrrolidone, and/or mixtures of any of the foregoing. Facilitating agents may also include at least one cationic surface stabilizer selected from the group consisting of a polymer, a biopolymer, a polysaccharide, a cellulosic, an alginate, a nonpolymeric compound, and a phospholipid. Facilitating agents may also include at least one surface stabilizer selected from the group consisting of cationic lipids, benzalkonium chloride, sulfonium compounds, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$) dimethylbenzyl ammonium chloride, N-alkyl ($C_{14-18}$)dimethyl-benzyl ammonium chloride, N-tetradecylidmethyl-benzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-diclecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, POLYQUAT 10™, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, MIRAPOL™, ALKAQUAT™, alkyl pyridinium salts; amines, amine salts, amine oxides, imide azolinium salts, protonated quaternary acrylamides, methylated quaternary polymers, cationic guar, polymethylmethacrylate trimethylammonium bromide, polyvinylpyrrolidone-2-dimetbylaminoethyl methacrylate dimethyl sulfate, hexadecyltrimethyl ammonium bromide, poly (2-methacryloxyethyltrimethylammonium bromide) (S1001), poly(N-vinylpyrrolidone/2-dimethylaminoethyl methacrylate) di methylsulphate quarternary (S1002), (S-630) poly(pyrrolidone-co-vinylacetate) and poly(2-methylacryloxyamidopropyltrimethylammonium chloride) (S1004).

In some cases the preferred stabilizer is CTAB. Those of skill in the art will appreciate that a wide variety of other surface stabilizers are suitable for such stabilization.

Should additional purification of the biologically active compound in nanoparticulate form be required, then conventional purification techniques may be employed. The appropriate technique will depend on the nature of the purification required. Those skilled in the art are familiar with such techniques and would readily appreciate adaptation of such techniques to the biologically active compound in nanoparticulate form of the invention.

The present invention includes biologically active compounds in nanoparticulate form at least partially separated from the grinding compound by the methods described above, the use of such in the preparation of a medicament, and the treatment of an animal, including man, by the administration of a therapeutically effective amount of the biologically active compounds in nanoparticulate form by way of the medicament.

A highly advantageous aspect of the present invention is that certain grinding compounds appropriate for use in the method of the invention (in that they physically degrade to the desired extent under dry milling conditions) are also pharmaceutically acceptable and thus appropriate for use in a medicament. Where the method of the present invention does not involve complete separation of the grinding compound from the biologically active compound in nanoparticulate form, the present invention encompasses methods for the production of a medicament incorporating both the biologically active compound in nanoparticulate form and at least a portion of the milled grinding compound, medicaments so produced and methods of treatment of an animal, including man, using a therapeutically effective amount of said biologically active compounds by way of said medicaments.

The medicament may include only the biologically active compound in nanoparticulate form and the grinding compound or, more preferably, the biologically active compounds in nanoparticulate form and grinding compound may be combined with one or more pharmaceutically acceptable carriers, as well as any desired excipients or other like agents commonly used in the preparation of medicaments.

Analogously, a highly advantageous aspect of the present invention is that certain grinding compounds appropriate for use in the method of the invention (in that they physically degrade to a desirable extent under dry milling conditions) are also appropriate for use in an agricultural chemical composition. Where the method of the present invention does not involve complete separation of the grinding compound from the biologically active compound in nanoparticulate form, the present invention encompasses methods for the production of a agricultural chemical composition incorporating both the biologically active compound in nanoparticulate form and at least a portion of the milled grinding compound, agricultural chemical composition so produced and methods of use of such compositions.

The agricultural chemical composition may include only the biologically active compound in nanoparticulate form and the grinding compound or, more preferably, the biologically active compounds in nanoparticulate form and grinding compound may be combined with one or more acceptable carriers, as well as any desired excipients or other like agents commonly used in the preparation of agricultural chemical compositions.

In one particular form of the invention, the grinding compound is both appropriate for use in a medicament and readily separable from the biologically active compound in nanoparticulate form by methods not dependent on particle size. Such grinding compounds are described in the following detailed description of the invention. Such grinding compounds are highly advantageous in that they afford significant flexibility in the extent to which the grinding compound may be incorporated with the biologically active compound in nanoparticulate form into a medicament.

Thus, the present invention encompasses a method for the manufacture of a medicament comprising a therapeutically active compound in nanoparticulate form, the method comprising the steps of:
dry milling a mixture of a solid biologically active compound and a millable grinding compound, in a mill comprising a plurality of milling bodies, to produce a solid dispersion or solution comprising nanoparticulate biologically active compound dispersed in at least partially milled grinding compound; and
using said solid dispersion or solution in the manufacture of a medicament.

The solid dispersion or solution may then be separated from the milling bodies and removed from the mill.

In one embodiment, the grinding compound is separated from the dispersion or solution. Where the grinding compound is not fully milled, the unmilled grinding compound is separated from the nanoparticulate biologically active compound. In a further aspect, at least a portion of the milled grinding compound is separated from the nanoparticulate biologically active compound.

The milling bodies are essentially resistant to fracture and erosion in the dry milling process.

The quantity of the grinding compound relative to the quantity of biologically active compound in nanoparticulate form, and the extent of milling of the grinding compound, is sufficient to inhibit reagglomeration of the biologically active compound in nanoparticulate form.

The grinding compound is not chemically nor mechanically reactive with the pharmaceutical compound under the dry milling conditions of the method of the invention.

Preferably, the medicament is a solid dosage form, however, other dosage forms may be prepared by those of ordinary skill in the art.

In one form, after the step of separating said solid solution or dispersion from the plurality of milling bodies, and before the step of using said solid solution or dispersion in the manufacture of a medicament, the method may comprise the step of:
removing a portion of the grinding compound from said solid dispersion or solution to provide a solid solution or dispersion enriched in the biologically active compound in nanoparticulate form;
and the step of using said solid solution or dispersion in the manufacture of a medicament, more particularly comprises the step of using the solid solution or dispersion enriched in the biologically active compound in nanoparticulate form in the manufacture of a medicament.

In one aspect, where the grinding compound is not fully milled, the unmilled grinding compound is separated from the nanoparticulate biologically active compound. In a further aspect, at least a portion of the milled grinding compound is separated from the nanoparticulate biologically active compound.

The present invention includes medicaments manufactured by said methods, and methods for the treatment of an animal, including man, by the administration of a therapeutically effective amount of the biologically active compounds in nanoparticulate form by way of said medicaments.

In another embodiment of the invention, a facilitating agent is also comprised in the mixture to be milled. Such facilitating agents appropriate for use in the invention include diluents, surface stabilizers, binding agents, filling agents, lubricating agents, sweeteners, flavouring agents, preservatives, buffers, wetting agents, disintegrants, effervescent agents and agents that may form part of a medicament, including a solid dosage form, or other material required for other specific drug delivery, such as the agents and media listed below under the heading *Medicinal and Pharmaceutical Compositions,* or any combination thereof.

A list of examples of surface stabilizers is provided above.

Biologically Active Compounds in Nanoparticulate Form and Compositions

The present invention encompasses pharmaceutically acceptable compounds in nanoparticulate form produced according to the methods of the present invention, compositions including such compounds, including compositions comprising such compounds together with at least a portion of the grinding compound.

Where the grinding compound is selectively substantially removed to leave pure pharmaceutically acceptable compounds in nanoparticulate form, agglomeration of the particles may sometimes occur forming larger particles. Due to the unique nature of the process described, these new agglomerated particles may have unique physical properties, through, for instance, having new polymorphic structures or nano-structured morphologies. Unique polymorphic structures and or the presence of nano structures morphologies may result in therapeutically beneficial properties including improved bioavailability. Thus, in some embodiments of the invention, a composition of the invention comprises substantially pure pharmaceutically acceptable compounds in nanoparticulate form. In other embodiments, particularly where the lack of grinding compound allows the nanoparticles formed during the process to agglomerate in a way detrimental to improving the dissolution rate, the preferred composition retains at least a portion of the grinding compound.

The pharmaceutically acceptable compounds in nanoparticulate form within the compositions of the invention are present at a concentration of between about 0.1% and about 99.0% by weight. Preferably, the concentration of pharmaceutically acceptable compounds in nanoparticulate form within the compositions will be about 5% to about 80% by weight, while concentrations of 10% to about 50% by weight are highly preferred. Desirably, the concentration will be in the range of about 10 to 15% by weight, 15 to 20% by weight, 20 to 25% by weight, 25 to 30% by weight, 30 to 35% by weight, 35 to 40% by weight, 40 to 45% by weight or 45 to 50% by weight for the composition prior to any later removal (if desired) of any portion of the grinding compound. Where part or all of the grinding compound has been removed, the relative concentration of pharmaceutically acceptable compounds in nanoparticulate form in the composition may be considerably higher depending on the amount of the grinding compound that is removed. For example, if all of the grinding compound is removed the concentration of nanoparticles in the preparation may be approach 100% by weight (subject to the presence of facilitating agents).

The dispersion of pharmaceutically acceptable compounds in nanoparticulate form in the grinding compound will be dependent on the weight percentage concentration of pharmaceutically acceptable compounds in nanoparticulate form Depending on that weight percentage concentration, nanoparticles of the pharmaceutically acceptable compounds in nanoparticulate form will be "dispersed" in the grinding compound if at least 0.1% of the nanoparticles are separated by the grinding compound. Preferably, greater than 10% of the nanoparticles will be spatially separated from each other by the grinding compound. More preferably at least 15, 20, 30, 40, 50, 55, 60, 65, 70, 75, 80, 85, 90, 92, 95, 98 or 99% of the nanoparticles will be spatially separated from each other by the grinding compound.

Compositions produced according to the present invention are not limited to the inclusion of a single species of pharmaceutically acceptable compounds in nanoparticulate form. More than one species of pharmaceutically acceptable compounds in nanoparticulate form may therefore be present in the composition. Where more than one species of pharmaceutically acceptable compounds in nanoparticulate form is present, the composition so formed may either be prepared in a dry milling step, or the pharmaceutically acceptable compounds in nanoparticulate form may be prepared separately and then combined to form a single composition.

Medicaments

The medicaments of the present invention may include the pharmaceutically acceptable compound in nanoparticulate form, optionally together with at least a portion of the grinding compound, combined with one or more pharmaceutically acceptable carriers, as well as other agents commonly used in the preparation of pharmaceutically acceptable compositions.

As used herein "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral administration, intravenous, intraperitoneal, intramuscular, sublingual, transdermal or oral administration. Pharmaceutically acceptable carriers include sterile aqueous solutions or dispersions and sterile powders for the extemporaneous preparation of sterile injectable solutions or dispersion. The use of such media and agents for the manufacture of medicaments is well known in the art. Except insofar as any conventional media or agent is incompatible with the pharmaceutically acceptable compound in nanoparticulate form, use thereof in the manufacture of a pharmaceutical composition according to the invention is contemplated.

Pharmaceutical acceptable carriers according to the invention may include one or more of the following examples:

(1) polymeric surface stabilizers which are capable of adhering to the surface of the active agent but do not take part in or undergo any chemical reaction with the active agent itself, such as polymeric surface stabilizers, including, but are not limited to polyethylene glycol (PEG), polyvinylpyrrolidone (PVP), polyvinylalcohol, corspovidone, polyvinylpyrrolidone-polyvinylacytate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, and their polymers, emulsifiers, sugar gum, starch, organic acids and their salts, vinyl pyrrolidone and vinyl acetate; and or (2) binding agents such as various celluloses and cross-linked polyvinylpyrrolidone, microcrystalline cellulose; and or (3) filling agents such as lactose monohydrate, lactose anhydrous, and various starches; and or (4) lubricating agents such as agents that act on the flowability of the powder to be compressed, including colloidal silicon dioxide, talc, stearic acid, magnesium stearate, calcium stearate, silica gel; and or (5) sweeteners such as any natural or artificial sweetener including sucrose, xylitol, sodium saccharin, cyclamate, aspartame, and accsulfame K; and or (6) flavouring agents; and or
(7) preservatives such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride; and or
(8) buffers; and or
(9) Diluents such as pharmaceutically acceptable inert fillers, such as microcrystalline cellulose, lactose, dibasic calcium phosphate, saccharides, and/or mixtures of any of the foregoing; and or
(10) wetting agents such as corn starch, potato starch, maize starch, and modified starches, croscarmellose sodium, crosspovidone, sodium starch glycolate, and mixtures thereof; and or
(11) disintegrants; and or
(12) effervescent agents such as effervescent couples such as an organic acid (e.g., citric, tartaric, malic, fumaric, adipic, succinic, and alginic acids and anhydrides and acid salts), or a carbonate (e.g. sodium carbonate, potassium carbonate, magnesium carbonate, sodium glycine carbonate, L-lysine carbonate, and arginine carbonate) or bicarbonate (e.g. sodium bicarbonate or potassium bicarbonate); and or
(13) other pharmaceutically acceptable excipients.

Medicaments of the invention suitable for use in animals and in particular in man typically must be sterile and stable under the conditions of manufacture and storage. The medicaments of the invention comprising the biologically active compound in nanoparticulate form can be formulated as a solution, microemulsion, liposome, or other ordered structure suitable to high drug concentration. Actual dosage levels of the biologically active compound in the medicament of the invention may be varied in accordance with the nature of the biologically active compound, as well as the potential increased efficacy due to the advantages of providing and administering the biologically active compound in nanoparticulate form (e.g., increased solubility, more rapid dissolution, increased surface area of the biologically active compound in nanoparticulate form, etc.).

Thus as used herein "therapeutically effective amount" will refer to an amount of biologically active compound in nanoparticulate form required to effect a therapeutic response in an animal. Amounts effective for such a use will depend on: the desired therapeutic effect; the route of administration; the potency of the biologically active compound; the desired duration of treatment; the stage and severity of the disease being treated; the weight and general state of health of the patient; and the judgment of the prescribing physician.

In another embodiment, the biologically active compound in nanoparticulate form, optionally together with at least a portion of the grinding compound, of the invention may be combined into a medicament with another biologically active compound, or even the same biologically active compound. In the latter embodiment, a medicament may be achieved which provides for different release characteristics—early release from the biologically active compound in nanoparticulate form, and later release from a larger average size biologically active compound in nanoparticulate form or a non-nanoparticulate biologically active compound.

Modes of Administration of Medicaments Comprising Biologically Active Compounds in Nanoparticulate Form Medicaments of the invention can be administered to animals, including man, in any pharmaceutically acceptable manner, such as orally, rectally, pulmonary, intravaginally, locally (powders, ointments or drops), transdermal, or as a buccal or nasal spray.

Solid dosage forms for oral administration include capsules, tablets, pills, powders, pellets, and granules. For capsules, tablets, and pills, the dosage forms may also comprise buffering agents. Further, incorporating any of the normally employed excipients, such as those previously listed, and generally 10-95% of the biologically active agent in nanoparticulate form, and more preferably at a concentration of 25%-75% will form a pharmaceutically acceptable non-toxic oral composition.

Medicaments of the invention may be parenterally administered as a solution of the biologically active agent in nanoparticulate form suspended in an acceptable carrier, preferably an aqueous carrier. A variety of aqueous carriers may be used, e.g. water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration.

For aerosol administration, medicaments of the invention are preferably supplied along with a surface stabilizer and propellant. The surface stabilizer must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surface stabilizer may constitute 0.1%-20% by weight of the composition, preferably 0.25-5%. The balance of the composition is ordinarily propellant. A carrier can also be included, as desired, as with, e.g., lecithin for intranasal delivery.

Medicaments of the invention may also be administered via liposomes, which serve to target the active agent to a particular tissue, such as lymphoid tissue, or targeted selectively to cells. Liposomes include emulsions, foams, micelles, insoluble monolayers, liquid crystals, phospholipid dispersions, lamellar layers and the like. In these preparations the nanocomposite microstructure composition is incorporated as part of a liposome, alone or in conjunction with a molecule that binds to or with other therapeutic or immunogenic compositions.

As described above, the biologically active compound in nanoparticulate form can be formulated into a solid dosage form (e.g., for oral or suppository administration), together with at least a portion of the grinding compound then there may be little or no need for further stabilizing the dispersion since the grinding compound may effectively act as a solid-state stabilizer.

However, if the biologically active compound in nanoparticulate form is to be utilized in a liquid (or gaseous) suspension, the nanoparticles comprising the biologically active compound in nanoparticulate form may require further stabilization once the solid carrier has been substantially removed to ensure the elimination, or at least minimisation of particle agglomeration.

Therapeutic Uses

Therapeutic uses of the medicaments of the invention include pain relief, anti-inflammatory, migraine, asthma, and other disorders that require the active agent to be administered with a high bioavailability.

One of the main areas when rapid bioavailability of a biologically active compound is required is in the relief of pain. The minor analgesics, such as cyclooxgenase inhibitors (aspirin related drugs) may be prepared as medicaments according to the present invention.

Medicaments of the invention may also be used for treatment of eye disorders. That is, the biologically active compound in nanoparticulate form may be formulated for administration on the eye as an aqueous suspension in physiological saline, or a gel. In addition, the biologically active compound in nanoparticulate form may be prepared in a powder form for administration via the nose for rapid central nervous system penetration.

Treatment of cardiovascular disease may also benefit from biologically active compounds in nanoparticulate form according to the invention, such as treatment of angina pectoris and, in particular, molsidomine may benefit from better bioavailability.

Other therapeutic uses of the medicaments of the present invention include treatment of hair loss, sexual dysfunction, or dermal treatment of psoriasis.

The invention will now be described with greater particularity for the preparation of forms of raloxifene.

Forms of Raloxifene

The present invention encompasses particulate amorphous raloxifene, pharmaceutically acceptable raloxifene salts and solvates. Methods for the preparation of such amorphous compounds are described in U.S. Pat. No. 6,713,494 (Eli Lilly and Company).

Where the raloxifene or the pharmaceutically acceptable salt or solvate of the present invention is crystalline, the present invention should not be understood to be limited to any particular polymorph thereof.

Pharmaceutically acceptable salts of the present invention may be formed from a range of organic or inorganic acids.

Typical inorganic acids used to form such salts include hydrochloric, hydrobromic, hydroiodic, nitric, sulfuric, phosphoric, hypophosphoric, and the like.

Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartrate, and the like.

Published US patent application 20060154966 describes the preparation of raloxifene D-lactate, raloxifene L-lactate, Raloxifene DL-lactate, raloxifene D-lactate hemihydrate, raloxifene D-lactate 1/4-hydrate, raloxifene L-lactate hemihydrate, raloxifene L-lactate 1/4-hydrate, raloxifene DL-lactate hemihydrate and raloxifene DL-lactate 1/4-hydrate.

For certain applications, a preferred salt is the hydrochloride salt.

Particle Size

The costs associated with reducing particle size are not limited to the direct cost of milling. For example, U.S. Pat. No. 6,894,064 (Eli Lilly and Company; Benzothiapenes, formulations containing same and methods) explains that "very finely divided material presents difficulties and costs in capsule filling or tablet preparation, because the material will not flow, but becomes caked in finishing machinery", and that "[s]uch finishing difficulties generate non-homogeneity in the final product, which is not acceptable in a drug substance". Accordingly "there is always a dynamic between the properties which yield the maximum bioavailability (particle surface area) and the practical limits of manufacture" and "[t]he point of compromise which marks the "best solution" is unique to each situation and unique as to its determination".

It has now been found that by processing raloxifene, or a pharmaceutically acceptable salt or solvate thereof, to bring the particle size within the specified range, pharmaceutical compositions may be prepared which exhibit improved in vitro dissolution profiles and in vivo bioavailability relative to some known raloxifene hydrochloride forms. Further, in some forms of the invention, these improvements may be achieved without importing characteristics that are disadvantageous from a manufacturing perspective.

As stated above, the invention is characterised in that the particulate raloxifene, or pharmaceutically acceptable salt or solvate thereof, in particulate form having a mean particle size of between about 10 nm and about 500 nm.

In one form of the invention, the mean particle size is between about 75 nm and about 500 nm. In one form of the invention, the mean particle size is between about 75 nm and about 400 nm. In one form of the invention, the mean particle size is between about 75 nm and about 300 nm. In one form of the invention, the mean particle size is between about 75 nm and about 200 nm. In one form of the invention, the mean particle size is between about 75 nm and about 100 nm.

Size Distribution

In preferred forms of the invention, the particulate raloxifene, pharmaceutically acceptable salt or solvate thereof, has a narrow particle size distribution.

In a preferred form of the invention, about 90% of the particles have a particle size of less than about 500 nm. The particles distribution can be measured with dynamic light scattering of a dispersion of the particles with the aid of sonication, and after centrifugation at 500 rcf for 30 seconds to remove larger agglomerates from the dispersion. Other means to measure the particles size are for examples surface area measurements, and electron micrographs, which can be used to support the measured size distribution of the particles.

In one form of the invention, about 50% of the particles have a particle size of less than 500 nm. In another form of the invention, about 90% of the particles have a particle size of less than 500 nm. In one form of the invention, about 90% of the particles have a particle size of between about 100 and 500 nm. In one form of the invention, about 90% of the particles have a particle size of between about 75 nm and about 500 nm. In one form of the invention, about 90% of the particles have a particle size of between about 75 nm and about 400 nm. In one form of the invention, about 90% of the particles have a particle size of between about 75 nm and about 300 nm. In one form of the invention, about 90% of the particles have a particle size of between about 75 nm and about 200 nm. In one form of the invention, about 90% of the particles have a particle size of between about 75 nm and about 100 nm.

In addition to the role of particle size in vitro dissolution and in vivo absorption, another important aspect is its role on the various operations of the drug product manufacturing process. While the particle size specification ensures consistent delivery of the drug molecule to the sites of absorption in the gastrointestinal tract, it also allows for better control during the wet granulation step of the tablet manufacturing process.

By controlling the particle size, the variations in quantity of water needed to elicit the appropriate progression of the granulation power consumption curve is reduced. By maintaining the particle size within the previous mentioned constraints, established quantities of water can be dictated in the manufacturing ticket for routine lot manufacture. The granulation step is common to many tablet and capsule manufacturing operations and is typically driven by the addition of water to bring about the desired endpoint of the granulation. A downstream unit operation dependent upon the granulation endpoint is the milling of the dried granulation and the resulting particle size distribution obtained on the granulation. It has been discovered that the incoming particle size of the active ingredient also effects the ultimate particle size distribution of the dry milled agglomerates formed during granulations. For a fixed water quantity, a coarser distribution will result in a finer size distribution of the dry milled agglomerates. Too fine a granulation distribution can lead to poor granulation flow and poor control of individual tablet weight during the compression step. Thus the narrow particle size constraints previously mentioned have also resulted in making the process more amenable to automation by reducing the variations in water required during the granulation step and producing dry milled granules of the appropriate distribution to prevent the rejection of tablets during compression due to unacceptable tablet weight.

Agglomerates

Agglomerates comprising particles of raloxifene, a pharmaceutically acceptable salt or solvate thereof, said particles having a mean particle size of between about 10 nm and about 500 nm, should be understood to fall within the scope of the present invention, regardless of whether the agglomerates exceed 500 nm in size.

For certain applications of the particulate raloxifene, pharmaceutically acceptable salt or solvate thereof, of the present invention, the formation of agglomerates is highly desirable. Agglomerates of particles of raloxifene, or a pharmaceutically acceptable salt or solvate thereof, of the invention may afford the advantages of improved in vitro dissolution and in vivo bioavailability relative to some known raloxifene hydrochloride forms without attracting the processing disadvantages conventionally associated with decreased particle sizes.

Other Properties

In preferred forms of the invention, the particulate raloxifene, pharmaceutically acceptable salt or solvate thereof has a surface area of in excess of 5 $m^2/g$. Preferably still the particulate raloxifene, pharmaceutically acceptable salt or solvate thereof has a surface area in excess of 7 $m^2/g$. Preferably still the particulate raloxifene, pharmaceutically acceptable salt or solvate thereof has a surface area in excess of 10 $m^2/g$. Preferably still the particulate raloxifene, pharmaceutically acceptable salt or solvate thereof has a surface area in excess of 15 $m^2/g$. Preferably still the particulate raloxifene, pharmaceutically acceptable salt or solvate thereof has a surface area in excess of 20 $m^2/g$. Preferably still the particulate raloxifene, pharmaceutically acceptable salt or solvate thereof has a surface area in excess of 25 $m^2/g$. Preferably still the particulate raloxifene, pharmaceutically acceptable salt or solvate thereof has a surface area in excess of 30 $m^2/g$. Preferably still the particulate raloxifene, pharmaceutically acceptable salt or solvate thereof has a surface area in excess of 35 $m^2/g$. Preferably still the particulate raloxifene, pharmaceutically acceptable salt or solvate thereof has a surface area in excess of 40 $m^2/g$. Preferably still the particulate raloxifene, pharmaceutically acceptable salt or solvate thereof has a surface area in excess of 50 $m^2/g$. Preferably still the particulate raloxifene, pharmaceutically acceptable salt or solvate thereof has a surface area in excess of 55 $m^2/g$. Preferably still the particulate raloxifene, pharmaceutically acceptable salt or solvate thereof has a surface area of up to approximately 57 $m^2/g$.

In one aspect of the invention, there is provided particulate crystalline raloxifene, or a pharmaceutically acceptable salt or solvate thereof which, when administered orally to dogs, demonstrates a peak plasma concentration ($C_{max}$) of greater than 12 ng/mL.

In one aspect of the invention, there is provided particulate crystalline raloxifene, or a pharmaceutically acceptable salt or solvate thereof which, when administered orally to dogs, demonstrates an area under the concentration versus time curve ($AUC_{0-t}$) greater than 33 ng.h/mL.

In one aspect of the invention, there is provided particulate crystalline raloxifene, or a pharmaceutically acceptable salt or solvate thereof which, when administered orally to dogs, demonstrates a median time to maximum plasma concentration ($T_{max}$) of within 1 hour.

Methods of Producing Particulate Raloxifene Hydrochloride

As summarised, the present invention further provides methods for producing said particulate raloxifene, or a pharmaceutically acceptable salt or solvate thereof.

In particular, the present invention comprises a method for producing a particulate raloxifene, or a pharmaceutically acceptable salt or solvate thereof, with a mean particle size of between about 10 nm and about 500 nm, the method comprising the step of:

milling a mixture of a solid raloxifene hydrochloride and a millable grinding compound, in a mill comprising a plurality of milling bodies, to produce a solid dispersion or solution comprising particulate raloxifene or a pharmaceutically acceptable salt or solvate thereof with a mean particle size of between about 10 nm and about 500 nm dispersed in at least partially milled grinding compound.

In a preferred form of the invention, the milling step is a dry milling step.

In one form of the invention, the mean particle size is between about 75 nm nm and about 500 nm. In one form of the invention, the mean particle size is between about 75 nm and about 400 nm. In one form of the invention, the mean particle size is between about 75 nm and about 300 nm. In one form of the invention, the mean particle size is between about 75 nm and about 200 nm. In one form of the invention, the mean particle size is between about 75 nm and about 100 nm.

In a preferred form of the invention, about 50% of the particles have a particle size of less than about 500 nm. In one form of the invention, about 90% of the particles have a particle size of between about 100 and 500 nm. In one form of the invention, about 90% of the particles have a particle size of between about 75 nm nm and about 500 nm. In one form of the invention, about 90% of the particles have a particle size of between about 75 nm and about 400 nm. In one form of the invention, about 90% of the particles have a particle size of between about 75 nm and about 300 nm. In one form of the invention, about 90% of the particles have a particle size of between about 75 nm and about 200 nm. In one form of the invention, about 90% of the particles have a particle size of between about 75 nm and about 100 nm.

The term "millable" means that the grinding compound is capable of being physically degraded under the dry milling conditions of the method of the invention. In one embodiment of the invention, the milled grinding compound is of a comparable particle size to the nanoparticulate biologically active compound.

In a highly preferred form, the grinding compound is harder than the solid raloxifene, pharmaceutically acceptable salt or solvate thereof, and is thus capable of physically degrading such under the dry milling conditions of the invention. Again without wishing to be bound by theory, under these circumstances it is believed that the millable grinding compound affords the advantage of the present invention through a second route, with the smaller particles of grinding compound produced under the dry milling conditions enabling the production of smaller particles of raloxifene or the pharmaceutically acceptable salt or solvate thereof.

The solid dispersion or solution of raloxifene or the pharmaceutically acceptable salt or solvate thereof may then be separated from the milling bodies and removed from the mill.

In a preferred aspect, the grinding compound is separated from the dispersion or solution. In a further aspect, at least a portion of the milled grinding compound is separated from the particulate raloxifene hydrochloride.

The milling bodies are essentially resistant to fracture and erosion in the dry milling process.

The quantity of the grinding compound relative to the quantity of particulate raloxifene, pharmaceutically acceptable salt or solvate thereof, and the extent of physical degradation of the grinding compound, is sufficient to inhibit reagglomeration of the raloxifene, pharmaceutically acceptable salt or solvate thereof. The grinding compound is not chemically reactive with the pharmaceutical raloxifene, pharmaceutically acceptable salt or solvate thereof under the milling conditions of the invention.

In one embodiment of the invention, the milled grinding compound is of a comparable particle size to the particulate raloxifene, pharmaceutically acceptable salt or solvate thereof.

The physical properties of the grinding compound necessary to achieve the requisite degradation are dependant on the precise milling conditions. For example a harder grinding compound may degrade to a sufficient extent provided under more vigorous dry milling conditions.

Physical properties of the grinding compound relevant to the extent that the agent will degrade under dry milling conditions include hardness, friability, as measured by indicia such as fracture toughness and brittleness index.

Preferably, the grinding compound is of low abrasivity. Low abrasivity is desirable to minimise contamination of the dispersion or solution of the particulate raloxifene hydrochloride in the grinding compound by the milling bodies and/or the milling chamber of the media mill. An indirect indication of the abrasivity can be obtained by measuring the level of milling-based contaminants.

Preferably, the grinding compound has a low tendency to agglomerate during dry milling. While it is difficult to objectively quantify the tendency to agglomerate during milling, it is possible to obtain a subjective measure by observing the level of "caking" of the grinding compound on the milling bodies and the milling chamber of the media mill as dry milling progresses.

The grinding compound may be an inorganic or organic compound. In one embodiment, the grinding compound is selected from the following: sodium hydrogen sulfate, sodium hydrogen carbonate, sodium hydroxide, or succinic acid; crystalline organic acids, for example (but not limited to) fumaric acid, maleic acid, tartaric acid, citric acid); alternatively ammonium salts (or salts of volatile amines), for example (but not limited to) ammonium chloride, methylamine hydrochloride, ammonium bromide, crystalline hydroxides, hydrogen carbonates, hydrogen carbonates of pharmaceutical acceptable alkali metals, such as but not limited by, sodium, potassium, lithium, calcium, and barium, sodium sulphate, sodium chloride, sodium metabisulphite, sodium thiosulphate, ammonium chloride, Glauber's salt, ammonium carbonate, sodium bisulphate, magnesium sulphate, potash alum, potassium chloride, sodium carbonate, sodium bicarbonate, potassium carbonate, potassium bicarbonate.

Selection of an appropriate grinding compound affords particular highly advantageous applications of the method of the present invention. Some grinding compounds appropriate for use in the invention are readily separable from the particulate raloxifene, pharmaceutically acceptable salt or solvate thereof by methods not dependent on particle size (such methods being inappropriate due to the degradation of the grinding compound). For example, selecting an appropriate grinding compound that also possesses solubility properties different from the particulate raloxifene, pharmaceutically acceptable salt or solvate thereof allows separation of the two by relatively straightforward selective dissolution techniques. Examples of such grinding compounds are provided in the detailed description of the invention. Thus, a particularly advantageous application of the method of the invention is the use of a water-soluble salt as a grinding compound.

A highly advantageous aspect of the present invention is that certain grinding compounds appropriate for use in the method of the invention are also appropriate for use in a medicament. The present invention encompasses methods for the production of a medicament incorporating both the particulate raloxifene, pharmaceutically acceptable salt or solvate thereof and at least a portion of the grinding compound, medicaments so produced, and methods of treatment of an animal, including man, using a therapeutically effective amount of said biologically active compounds by way of said medicaments.

The medicament may include only the particulate raloxifene, pharmaceutically acceptable salt or solvate thereof together with the milled grinding compound or, more preferably, the particulate raloxifene, pharmaceutically acceptable salt or solvate thereof and milled grinding compound may be combined with one or more pharmaceutically acceptable carriers, as well as any desired excipients or other like agents commonly used in the preparation of medicaments.

In one particular form of the invention, the grinding compound is both appropriate for use in a medicament and readily separable from the particulate raloxifene, pharmaceutically acceptable salt or solvate thereof by methods not dependent on particle size. Such grinding compounds are described in the following detailed description of the invention. Such grinding compounds are highly advantageous in that they afford significant flexibility in the extent to which the grinding compound may be incorporated with the particulate raloxifene, pharmaceutically acceptable salt or solvate thereof into a medicament.

In one form of the invention, the grinding compound is sodium chloride. In one form of the invention, the grinding compound is calcium carbonate.

In a preferred embodiment, the grinding compound is a compound that is considered GRAS (generally regarded as safe) by persons skilled in the pharmaceutical arts.

In a preferred form of the invention, prior to the step of:
dry milling a mixture of a solid raloxifene hydrochloride and a millable grinding compound, in a mill comprising a plurality of milling bodies, to produce a solid dispersion or solution comprising particulate raloxifene or a pharmaceutically acceptable salt or solvate thereof with a mean particle size of between about 10 nm and about 500 nm dispersed in at least partially milled grinding compound;

the method of the present invention comprises the step of substantially drying the solid raloxifene or pharmaceutically acceptable salt or solvate thereof.

Preferably still, prior to the step of:
dry milling a mixture of a solid raloxifene hydrochloride and a millable grinding compound, in a mill comprising a plurality of milling bodies, to produce a solid dispersion or solution comprising particulate raloxifene or a pharmaceutically acceptable salt or solvate thereof with a mean particle size of between about 10 nm and about 500 nm dispersed in at least partially milled grinding compound;

the method of the present invention comprises the step of substantially drying the grinding compound.

Persons skilled in the art will be aware of many techniques for removing water from compounds. In one form of the invention, the step of substantially drying the solid raloxifene, pharmaceutically acceptable salt or solvate, is performed by exposing the raloxifene hydrochloride to a drying agent under vacuum for a suitable period of time. Persons skilled in the art will be aware of a range of appropriate drying agents.

In one form of the invention the drying agent is $P_2O_5$.

The number and size of milling bodies can be varied to alter the amount of energy applied during the milling. This results in variation of the size and characteristics of the resultant raloxifene. The examples show certain combinations optimized for the current scale of manufacture, however those skilled in the art will appreciate that as the process is scaled, variations to milling media size, number and energy applied will be required to produce the same product.

Preferably, the concentration of solid raloxifene, pharmaceutically acceptable salt or solvate, in the mixture of solid raloxifene solid raloxifene, pharmaceutically acceptable salt or solvate, and the millable grinding compound is between about 5% and about 25% v/v. Preferably still, the concentration is between about 5% and about 20% v/v. In a highly preferred form of the invention, the concentration is between about 10% and about 15% v/v. In one form of the invention, the concentration is about 15% v/v.

Milling Bodies

In the method of the present invention, the milling bodies are preferably chemically inert and rigid. The term "chemically-inert", as used herein, means that the milling bodies do not react chemically with the rolixifene hydrochloride or the grinding compound.

The milling bodies are essentially resistant to fracture and erosion in the milling process.

The milling bodies are desirably provided in the form of bodies which may have any of a variety of smooth, regular shapes, flat or curved surfaces, and lacking sharp or raised edges. For example, suitable milling bodies can be in the form of bodies having ellipsoidal, ovoid, spherical or right cylindrical shapes. Preferably, the milling bodies are provided in the form of one or more of beads, balls, spheres, rods, right cylinders, drums or radius-end right cylinders (i.e., right cylinders having hemispherical bases with the same radius as the cylinder).

The milling media bodies desirably have an effective mean particle diameter (i.e. "particle size") between about 0.1 and 30 mm, more preferably between about 1 and about 15 mm, still more preferably between about 3 and 10 mm.

The milling bodies may comprise various materials such as ceramic, glass, metal or polymeric compositions, in a particulate form. Suitable metal milling bodies are typically spherical and generally have good hardness (i.e. RHC 60-70), roundness, high wear resistance, and narrow size distribution and can include, for example, balls fabricated from type 52100 chrome steel, type 316 or 440C stainless steel or type 1065 high carbon steel.

Preferred ceramic materials, for example, may be selected from a wide array of ceramics desirably having sufficient hardness and resistance to fracture to enable them to avoid being chipped or crushed during milling and also having sufficiently high density. Suitable densities for milling media can range from about 1 to 15 g/cm$^3$. Preferred ceramic materials can be selected from steatite, aluminum oxide, zirconium oxide, zirconia-silica, yttria-stabilized zirconium oxide, magnesia-stabilized zirconium oxide, silicon nitride, silicon carbide, cobalt-stabilized tungsten carbide, and the like, as well as mixtures thereof.

Preferred glass milling media are spherical (e.g. beads), have a narrow size distribution, are durable, and include, for example, lead-free soda lime glass and borosilicate glass. Polymeric milling media are preferably substantially spherical and can be selected from a wide array of polymeric resins having sufficient hardness and friability to enable them to avoid being chipped or crushed during milling, abrasion-resistance to minimize attrition resulting in contamination of the product, and freedom from impurities such as metals, solvents, and residual monomers.

Preferred polymeric resins, for example, can be selected from crosslinked polystyrenes, such as polystyrene crosslinked with divinylbenzene, styrene copolymers, polyacrylates such as polymethylmethacrylate, polycarbonates, polyacetals, vinyl chloride polymers and copolymers, polyurethanes, polyamides, high density polyethylenes, polypropylenes, and the like. The use of polymeric milling media to grind materials down to a very small particle size (as opposed to mechanochemical synthesis) is disclosed, for example, in U.S. Pat. Nos. 5,478,705 and 5,500,331. Polymeric resins typically can have densities ranging from about 0.8 to 3.0 g/cm$^3$. Higher density polymeric resins are preferred. Alternatively, the milling media can be composite particles comprising dense core particles having a polymeric resin adhered thereon. Core particles can be selected from materials known to be useful as milling media, for example, glass, alumina, zirconia silica, zirconium oxide, stainless steel, and the like. Preferred core materials have densities greater than about 2.5 g/cm$^3$.

In one embodiment of the invention, the milling media are formed from a ferromagnetic material, thereby facilitating removal of contaminants arising from wear of the milling media by the use of magnetic separation techniques.

Each type of milling body has its own advantages. For example, metals have the highest specific gravities, which increase grinding efficiency due to increased impact energy. Metal costs range from low to high, but metal contamination of final product can be an issue. Glasses are advantageous from the standpoint of low cost and the availability of small bead sizes as low as 0.004 mm. However, the specific gravity of glasses is lower than other media and significantly more milling time is required. Finally, ceramics are advantageous from the standpoint of low wear and contamination, ease of cleaning, and high hardness.

In a specific form of the invention, the milling bodies comprise a plurality of steel balls of approximately 3 cm$^3$ volume and 40 g mass.

Dry Milling

In the dry milling process of the present invention, the solid raloxifene, or pharmaceutically acceptable salt or solvate thereof, and grinding compound, in the form of crystals, powders, or the like, are combined in suitable proportions with the plurality of milling bodies in a milling chamber that is mechanically agitated (i.e., with or without stirring) for a predetermined period of time at a predetermined intensity of agitation. Typically, a milling apparatus is used to impart motion to the milling bodies by the external application of agitation, whereby various translational, rotational or inversion motions or combinations thereof are applied to the milling chamber and its contents, or by the internal application of agitation through a rotating shaft terminating in a blade, propeller, impeller or paddle or by a combination of both actions.

During milling, motion imparted to the milling bodies can result in application of shearing forces as well as multiple impacts or collisions having significant intensity between milling bodies and particles of the reactant powders. The solid raloxifene hydrochloride and the grinding compound is influenced by a wide variety of processing parameters including: the type of milling apparatus; the intensity of the forces generated, the kinematic aspects of the process; the size, density, shape, and composition of the milling bodies; the weight ratio of the raloxifene hydrochloride and grinding compound mixture to the milling bodies; the duration of milling; the physical properties the grinding compound; the atmosphere present during activation; and others.

Advantageously, the media mill is capable of repeatedly or continuously applying mechanical compressive forces and shear stress to the biologically active compound substrate and the grinding compound. Suitable media mills include but are not limited to the following: high-energy ball, sand, bead or pearl mills, basket mill, planetary mill, vibratory action ball mill, multi-axial shaker/mixer, stirred ball mill, horizontal small media mill, multi-ring pulverizing mill, and the like, including small milling media. The milling apparatus also can contain one or more rotating shafts.

In a preferred form of the invention, the dry milling is effected in a ball mill. Throughout the remainder of the specification reference will be made to dry milling being carried out by way of a ball mill. Examples of this type of mill are attritor mills, nutating mills, tower mills, planetary mills, vibratory mills and gravity-dependent-type ball mills. It will be appreciated that dry milling in accordance with the method of the invention may also be achieved by any suitable means other than ball milling. For example, dry milling may also be achieved using jet mills, rod mills, roller mills or crusher mills.

It is preferred, but not essential, that the particle size of the solid raloxifene, or pharmaceutically acceptable salt or solvate thereof be less than about 100 µm, as may be determined by sieve analysis. If the coarse particle size of the solid raloxifene or pharmaceutically acceptable salt or solvate thereof, is greater than about 100 µm, then it is preferred that the particles of the solid raloxifene, or pharmaceutically acceptable salt or solvate thereof, be first reduced in size to less than 100 µm using a conventional milling method such as airjet or fragmentation milling.

Pharmaceutical Compositions Comprising, or Formulated Using, Particulate Raloxifene, or Pharmaceutically Acceptable Salt or Solvate Thereof, According to the Invention As stated in the summary, the present invention also provides pharmaceutical compositions comprising or formulated using the said particulate raloxifene, or pharmaceutically acceptable salt or solvate thereof.

The pharmaceutical compositions of the invention may include a pharmaceutically acceptable carrier, wherein "pharmaceutically acceptable carrier" includes any and all solvents, dispersion media, coatings, antibacterial and antifungal agents, isotonic and absorption delaying agents, and the like that are physiologically compatible.

Preferably, the pharmaceutically acceptable carrier is suitable for parenteral, intravenous, intraperitoneal, intramuscular, sublingual, transdermal or oral administration. Pharmaceutically acceptable carriers include sterile aqueous solutions or dispersions and sterile powders for the extemporaneous preparation of sterile injectable solutions or dispersion. The use of such media and agents for the manufacture of pharmaceutical compositions is well known in the art. Except insofar as any conventional media or agent is incompatible with the particulate raloxifene hydrochloride of the invention, use thereof in the manufacture of a pharmaceutical composition according to the invention is contemplated.

Pharmaceutical compositions according to the invention may include one or more of the following additives:

(1) polymeric surface stabilizers which are capable of adhering to the surface of the active agent but do not take part in or undergo any chemical reaction with the active agent itself, such as polymeric surface stabilizers, including, but are not limited to polyethylene glycol (PEG), polyvinylpyrrolidone (PVP), polyvinylalcohol, corspovidone, polyvinylpyrrolidone-polyvinylacytate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, and their polymers, emulsifiers, sugar gum, starch, organic acids and their salts, vinyl pyrrolidone and vinyl acetate; and or (2) binding agents such as various celluloses and cross-linked polyvinylpyrrolidone, microcrystalline cellulose; and or (3) filling agents such as lactose monohydrate, lactose anhydrous, and various starches; and or (4) lubricating agents such as agents that act on the flowability of the powder to be compressed, including colloidal silicon dioxide, talc, stearic acid, magnesium stearate, calcium stearate, silica gel; and or (5) sweeteners such as any natural or artificial sweetener including sucrose, xylitol, sodium saccharin, cyclamate, aspartame, and accsulfame K; and or (6) flavouring agents; and or (7) preservatives such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride; and or (8) buffers; and or (9) Diluents such as pharmaceutically acceptable inert fillers, such as microcrystalline cellulose, lactose, dibasic calcium phosphate, saccharides, and/or mixtures of any of the foregoing; and or

(10) wetting agents such as corn starch, potato starch, maize starch, and modified starches, croscarmellose sodium, crosspovidone, sodium starch glycolate, and mixtures thereof; and or

(11) disintegrants; and or

(12) effervescent agents such as effervescent couples such as an organic acid (e.g., citric, tartaric, malic, fumaric, adipic, succinic, and alginic acids and anhydrides and acid salts), or a carbonate (e.g. sodium carbonate, potassium carbonate, magnesium carbonate, sodium glycine carbonate, L-lysine carbonate, and arginine carbonate) or bicarbonate (e.g. sodium bicarbonate or potassium bicarbonate); and or

(13) other pharmaceutically acceptable excipients.

Pharmaceutical compositions suitable for use in animals and in particular in man typically must be sterile and stable under the conditions of manufacture and storage. The pharmaceutical composition comprising nanoparticles can be formulated as a solution, microemulsion, liposome, or other ordered structure suitable to high drug concentration.

Pharmaceutical compositions of the invention can be administered to humans and animals in any pharmaceutically acceptable manner, such as orally, rectally, pulmonary, intravaginally, locally (powders, ointments or drops), transdermal, or as a buccal or nasal spray.

Raloxifene is subject to significant first-pass metabolism, which impacts on bioavailability. Conventionally formulated raloxifene is generally considered not to be amenable to transdermal delivery. However, the particulate raloxifene, or pharmaceutically acceptable salt or solvate of the present invention is more amenable to such delivery.

Solid dosage forms for oral administration include capsules, tablets, pills, powders, pellets, granules, and the like. Such dosage forms may also comprise buffering agents.

Pharmaceutical compositions of the invention may be parenterally administered as a solution of the particulate raloxifene hydrochloride suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration.

For aerosol administration, pharmaceutical compositions of the invention are preferably supplied along with a surface stabilizer and propellant. The surface stabilizer must be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surface stabilizer may constitute 0.1%-20% by weight of the composition, preferably 0.25-5%. The balance of the composition is ordinarily propellant. A carrier can also be included, as desired, as with, e.g., lecithin for intranasal delivery.

Pharmaceutical compositions of the invention may also be administered via liposomes, which serve to target the active agent to a particular tissue, such as lymphoid tissue, or targeted selectively to cells. Liposomes include emulsions, foams, micelles, insoluble monolayers, liquid crystals, phospholipid dispersions, lamellar layers and the like. In these preparations the nanocomposite microstructure composition is incorporated as part of a liposome, alone or in conjunction with a molecule that binds to or with other therapeutic or immunogenic compositions.

Additionally, the compounds of this invention are well suited to formulation as sustained release dosage forms. The formulations can also be so constituted that they release the active ingredient only or preferably in a particular part of the intestinal tract, and/or over a period of time. Such formulations may include coatings, envelopes, or protective matrices which may be made from polymeric substances or waxes.

Suitable surface stabilisers may include CTAB, cetyl pyridinium chloride, gelatin, casein, phosphatides, dextran, glycerol, gum acacia, cholesterol, tragacanth, stearic acid, stearic acid esters and salts, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers, poloxamines, a charged phospholipid, dimyristoyl phophatidyl glycerol, dioctylsulfosuccinate, dialkylesters of sodium sulfosuccinic acid, dioctyl sodium sulfosuccinate, sodium lauryl sulfate, alkyl aryl polyether sulfonates, mixtures of sucrose stearate and sucrose distearate, triblock copolymers of the structure: -(-PEO)-(-PBO-)-(-PEO-)-, p-isononylphenoxypoly-(glycidol), decanoyl-N-methylglucamide; n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, octyl β-D-thioglucopyranoside, lysozyme, a PEG derivatized phospholipid, PEG derivatized cholesterol, a PEG derivatized cholesterol derivative, PEG derivatized vitamin A, PEG derivatized vitamin E, and random copolymers of vinyl acetate and vinyl pyrrolidone, and/or mixtures of any of the foregoing.

Suitable surface stabilisers may also include a cationic surface stabilizer selected from the group consisting of a polymer, a biopolymer, a polysaccharide, a cellulosic, an alginate, a nonpolymeric compound, and a phospholipid.

Suitable surface stabilisers may also include a surface stabilizer selected from the group consisting of cationic lipids, benzalkonium chloride, sulfonium compounds, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$) dimethylbenzyl ammonium chloride, N-alkyl ($C_{14-18}$)dimethyl-benzyl ammonium chloride, N-tetradecylidmethyl-benzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-diclecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, POLYQUAT 10™, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, MIRAPOL™, ALKAQUAT™, alkyl pyridinium salts; amines, amine salts, amine oxides, imide azolinium salts, protonated quaternary acrylamides, methylated quaternary polymers, cationic guar, polymethylmethacrylate trimethylammonium bromide, polyvinylpyrrolidone-2-dimetbylaminoethyl methacrylate dimethyl sulfate, hexadecyltrimethyl ammonium bromide, poly (2-methacryloxyethyltrimethylammonium bromide) (S1001), poly(N-vinylpyrrolidone/2-dimethylaminoethyl methacrylate) di methylsulphate quarternary (S1002), (S-630) poly(pyrrolidone-co-vinylacetate) and poly(2-methylacryloxyamidopropyltrimethylammonium chloride) (S1004).

In some embodiments the preferred surface stabilizer is CTAB.

In embodiments in which the particulate raloxifene hydrochloride is produced using a method of the invention, and the method of the invention utilises a surface stabilizer, in a preferred form of the invention, the surface stabilizer of the pharmaceutical composition is the same surface stabilizer as that used in the method. As would be understood by person skilled in the art, it may be desirable to add further quantities of the surface stabilizer to the particulate raloxifene hydrochloride for the purposes of preparing a pharmaceutical composition.

In embodiments in which the particulate raloxifene, or pharmaceutically acceptable salt or solvate thereof, is produced using a method of the invention, and the method of the invention utilises a grinding compound, in a preferred form of the invention, the water-soluble diluent of the pharmaceutical composition is the same as the grinding compound used in the method. As would be understood by person skilled in the art, it may be desirable to add further quantities of the water soluble diluent to the particulate raloxifene hydrochloride for the purposes of preparing a pharmaceutical composition, relative to the quantity of grinding compound used in the method, or to remove some of the grinding compound prior to preparation of the composition.

In one form, the pharmaceutical composition of the invention is an oral dosage form comprising particulate raloxifene according to the invention, or pharmaceutically acceptable salt or solvate thereof, according to the invention, a surfactant in the form of CTAB, and a water-soluble diluent in the form of sodium chloride.

As a further embodiment of the invention, the particulate raloxifene, or pharmaceutically acceptable salt or solvate thereof, may be administered along with an effective amount of an additional therapeutic agent, including but not limited to estrogen, progestin, benzothiophene compounds including raloxifene, naphthyl compounds having antiestrogen activity, bisphosphonate compounds such as alendronate and tiludronate, parathyroid hormone (PTH), including truncated and/or recombinant forms of PTH such as, for example, PTH (1-34), calcitonin, bone morphogenic proteins (BMPs), or combinations thereof. The different forms of these additional therapeutic agents available as well as the various utilities associated with same and the applicable dosing regimens are well known to those of skill in the art.

Various forms of estrogen and progestin are commercially available. As used herein, the term "estrogen" includes compounds having estrogen activity and estrogen-based agents. Estrogen compounds useful in the practice of the present invention include, for example, estradiol estrone, estriol, equilin, equilenin, estradiol cypionate, estradiol valerate, ethynyl estradiol, polyestradiol phosphate, estropipate, diethylstibestrol, dienestrol, chlorotrianisene, and mixtures thereof. Estrogen-based agents, include, for example, 17-.alpha.-ethynyl estradiol (0.01-0.03 mg/day), mestranol (05-0.15 mg/day), and conjugated estrogenic hormones such as Premarin™ (Wyeth-Ayerst; 0.2-2.5 mg/day). As used herein, the term "progestin" includes compounds having progestational activity such as, for example, progesterone, norethynodrel, norgestrel, megestrol acetate, norethindrone, progestin-based agents, and the like. Progestin-based agents include, for example, medroxyprogesterone such as Provera™ (Upjohn; 2.5-10 mg/day), norethylnodrel (1.0-10.0 mg/day), and norethindrone (0.5-2.0 mg/day). A preferred estrogen-based compound is Premarin™, and norethylnodrel and norethindrone are preferred progestin-based agents. The method of administration of each estrogen- and progestin-based agent is consistent with that known in the art.

The present invention will now be described with reference to the following non-limiting Examples. The description of the Examples is in no way limiting on the preceding paragraphs of this specification, but is provided for exemplification of the methods and compositions of the invention.

EXAMPLES

It will be apparent to persons skilled in the materials and pharmaceutical arts that numerous enhancements and modifications can be made to the above described processes without departing from the basic inventive concepts. For example, in some applications the biologically active compound substrate may be pretreated and supplied to the process in the pretreated form. All such modifications and enhancements are considered to be within the scope of the present invention, the nature of which is to be determined from the foregoing description and the appended claims. Furthermore, the following Examples are provided for illustrative purposes only, and are not intended to limit the scope of the processes or compositions of the invention.

A. Processing of Diclofenac Acid with Sodium Chloride Grinding Compound

A mixture consisting of a biologically active compound in the form of 0.439 g of diclofenac acid (DCA)

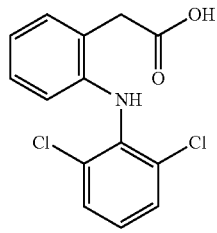 [SMILES: O=C(O)Cc1ccccc1Nc1c(Cl)cccc1Cl]

and grinding compound in the form of 3.681 g of sodium chloride (thereby providing the mixture at 10.7 and 89.3 weight % respectively, corresponding to 15 and 85 volume %, with a total volume of 2 cm³) was dry milled for 15 minutes using a Spex 8000D mixer/mill with a 70 cm³ hardened steel ball mill container containing ten 10 mm (40 g) stainless steel balls as the milling media. This resulted in the formation of a dispersion comprising DCA in nanoparticulate form dispersed within a matrix of grinding compound sodium chloride.

In order to examine the effect of volume ratio of DCA to NaCl on particle size, milling experiments were carried out with: 5 vol % (3.43 w %), 10 vol % (7 w %), 30 vol % (22.5 w %) and 50 vol % (45 w %) of DCA to NaCl (total volume of 2 cm³, 15 minute milling time).

Ultra-fine particles of diclofenac acid in nanoparticulate form were recovered by removing the grinding compound through washing with dilute hydrochloric acid. The washed powder was subsequently dried at room temperature for several hours in air.

In order to remove the grinding compound from the diclofenac acid in nanoparticulate form, the dispersion was washed as follows. To obtain 0.25 g of diclofenac particles varying amounts of dispersion were used, depending on the volume percentage. For a 15 vol % DCA dispersion, 2.339 g was slowly added to 40 mL of a vigorously stirred solution of 0.01 M HCl and 1 mM CTAB (cetyl trimethyl ammonium bromide) in a conical flask. The sample was stirred for 30 minutes and filled into 15 mL plastic tubes for centrifugation (falcon tubes). The sample was then subjected to 3 repeats of: centrifugation (whereas the centrifugation speed was increased for each washing step from 5,000 g to 8,000 g and finally to 12,000 g for a period of 3 minutes), removal of supernatant, addition of 0.01 M HCl and 1 mM CTAB, and redispersion by vortex and ultrasound sonication (5-10 seconds each).

Figure 2A:
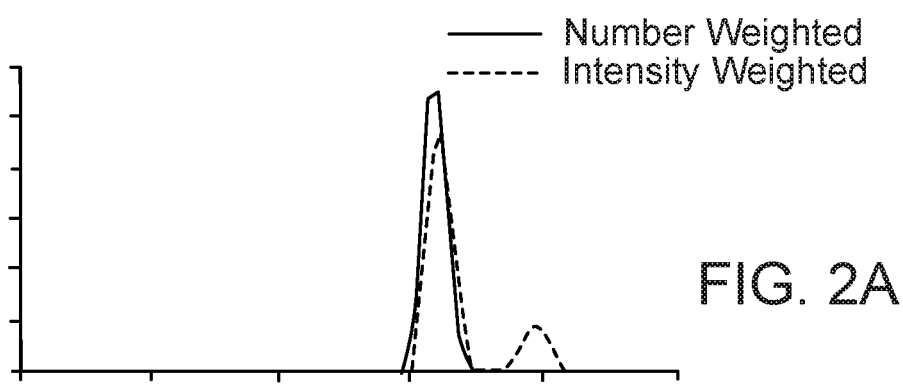
FIG. 2 illustrates diclofenac acid nanoparticles obtained by dry milling a 15 vol % diclofenac acid in NaCl grinding medium, and separated from the grinding medium by washing with 0.01 M HCl and 1 mM CTAB solution. Larger particles, as can be seen in the intensity distribution on (b), were largely removed by centrifugation for 1 min at 3,000 g to achieve a narrow size distribution of 160±30 nm, which is number weighted 100% (a). The amount of nanoparticles after removal of aggregates or larger particles by centrifugation in the dispersion or solution is greater than 80 weight %, as determined by the intensity weighted size distribution (a)
Figure 2B:
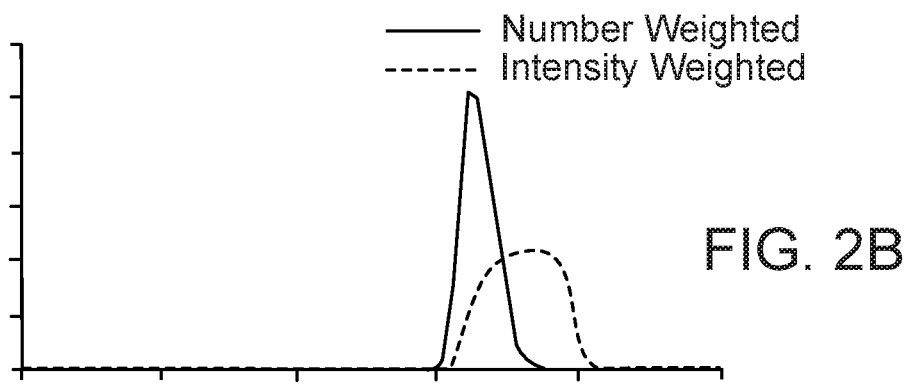
Figure 4:
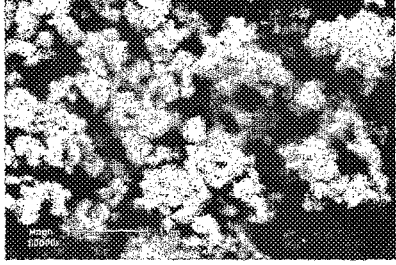
FIG. 4 comprises high resolution SEM and TEM images of washed diclofenac acid nanoparticles of 5, 10, 15, 30 and 50 wt % diclofenac acid to grinding compound ratio.

The SEM and TEM images (FIG. 4) demonstrate that nanoparticles of a diameter in the order of 100-200 nm size range after washing. BET results illustrated in FIG. 1, show the highest surface area (11.755±0.1035 m²/g) obtained was for the 5 vol % DCA. As can be seen from FIG. 2, Dynamic light scatter (DLS) analysis showed particle sizes of 160±30 nm.

The resulting dispersion for the 15 vol % sample, stabilized with the surface stabilizer CTAB, was found to comprise the diclofenac acid form of the drug (by XRD, FTIR and DSC), with nanoparticles less than 200 nm and the majority on the order of 30-50 nm. TEM of the DCA in nanoparticulate form (after washing the dispersion and stabilized with the surface stabilizer CTAB) also showed both spherical and nonspherical nanoparticles, the nonspherical particles appearing to be rod-shaped, having a minor-axis dimension of about 30 nm and a major-axis dimension of about 150 nm. DSC analysis of the melting point of the DCA in nanoparticulate form confirmed its identity as diclofenac acid, with a melting point in the range of 175-185° C.

Figure 7:
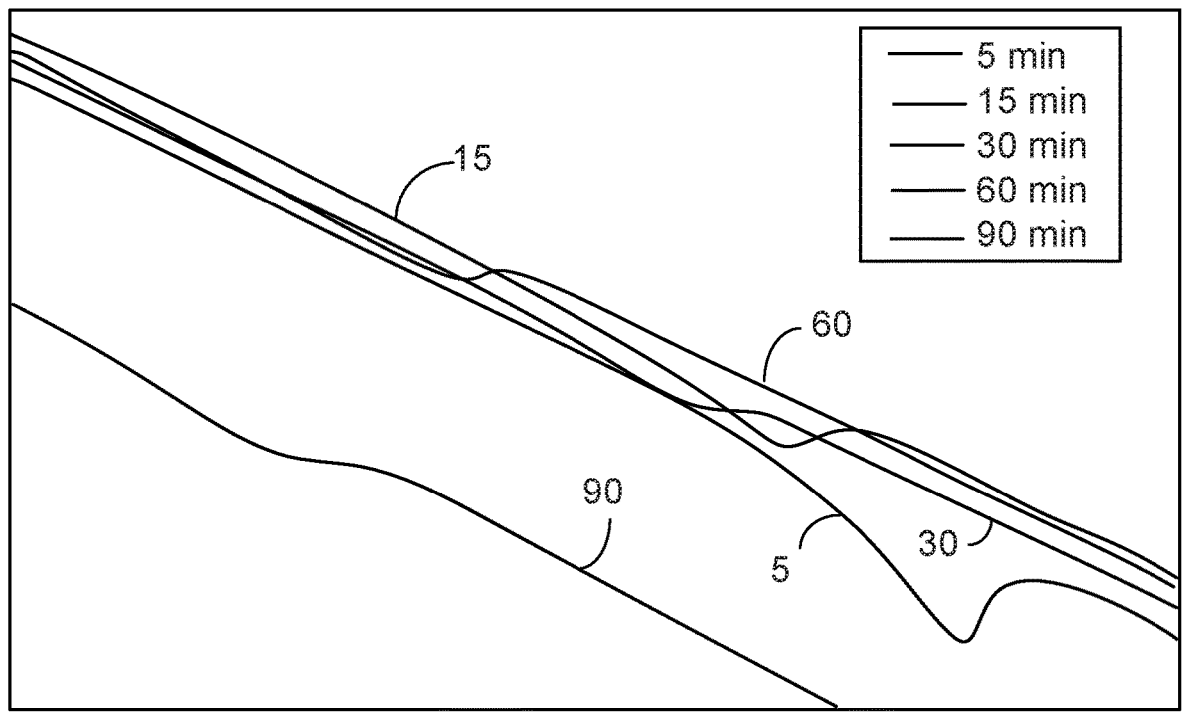
FIG. 7 illustrates the effect of increasing milling time of diclofenac acid with NaCl grinding compound, 15 vol %), showing that the melting point shifts to lower temperatures, likely due to a decrease of the diameter of the particles of diclofenac acid.

FIG. 7 illustrates the effect of increasing milling time of diclofenac acid with NaCl grinding compound, 15 vol %), showing that the melting point shifts to lower temperatures, likely due to a decrease of the diameter of the particles of diclofenac acid.

B. Processing of Olanzapine Plus Sodium Chloride Grinding Compound

A biologically active compound in the form of 0.39 g of conventional olanzapine powder,

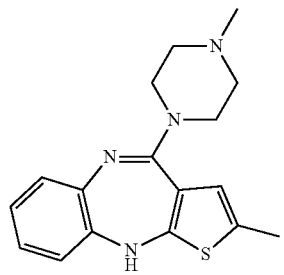 [SMILES: Cc1cc2c(s1)Nc1ccccc1N=C2N1CCN(C)CC1]

was placed in a milling apparatus (a 70 cm³ stainless steel ball mill container) with grinding compound in the form of 3.68 g of NaCl, thereby providing the mixture at 9.6 and 90.4 weight % respectively, corresponding to 15 and 85 volume %, with a total volume of 2 cm³. Milling media comprising 40 g of 10 mm steel balls (10 pieces) were employed in the container. The milling apparatus was closed under house vacuum prior to milling. Cooling was achieved with compressed air flow (100 kcpa). The mixture was dry milled for 15 minutes and 180 minutes, the composition resulting after milling for both times comprised olanzapine in nanoparticulate form dispersed in the grinding medium NaCl.

Figure 3A:
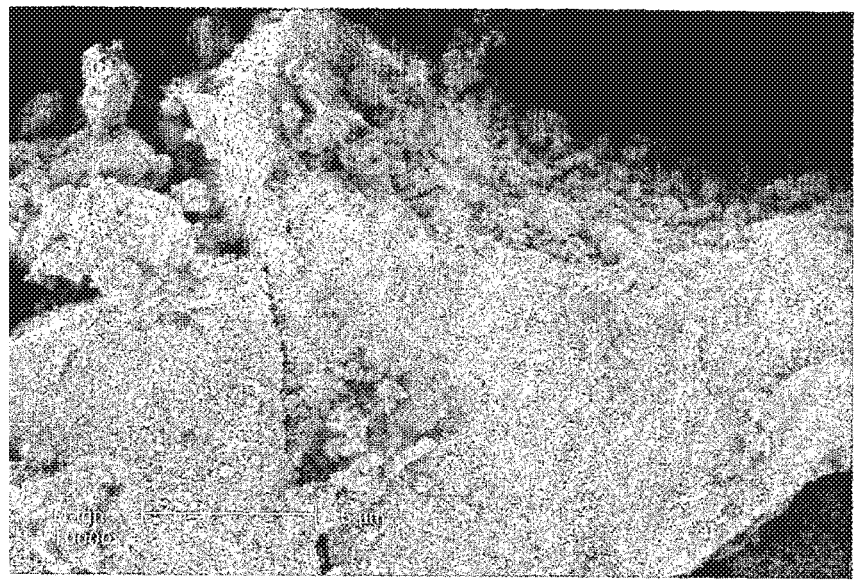
FIG. 3 comprises SEM images of olanzapine milled with NaCl grinding compound for 180 minutes, showing (a) agglomerate morphology of olanzapine/grinding compound mixture at 10000 magnification, and (b) nanoparticulate morphology of olanzapine/grinding compound mixture at 100000 magnification.
Figure 3B:
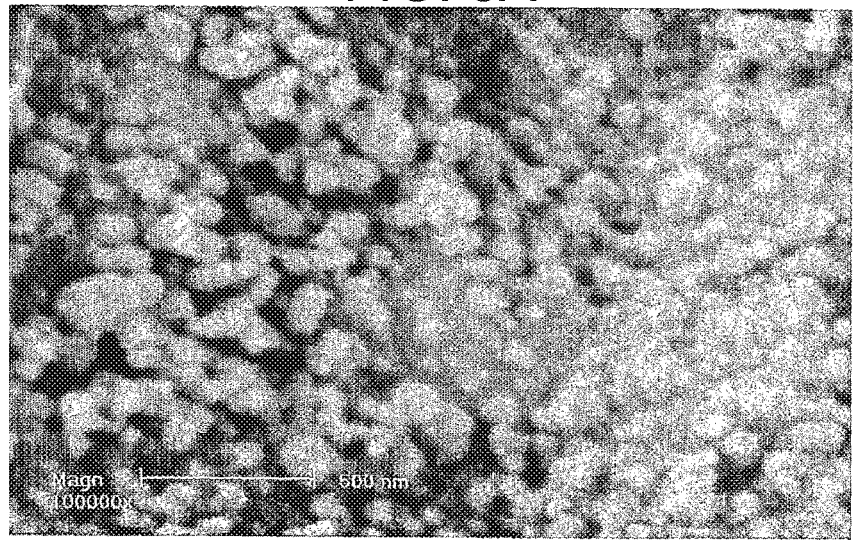

As can be seen from FIG. 3, scanning electron microscopy (SEM) of the resulting dispersion showed nanocrystalline structures and nanoparticles of olanzapine on the order of 100 nm. Milling times assayed included 15 and 180 minutes in two separate milling runs. Analysis of the melting point of the nanoparticles produced at 180 minute milling time period confirmed that the resulting composition was olanzapine, with a melting point in the range of 200° C. Material showed some decolourization at 180 minutes, which is attributed to degradation of the drug.

C. Processing of Diclofenac Acid with Ammonium Chloride Grinding Compound

Biologically active compound in the form of 0.439 g of conventional DCA powder,

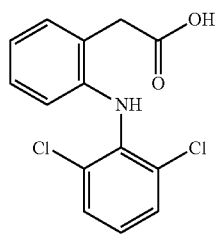 [SMILES: O=C(O)Cc1ccccc1Nc1c(Cl)cccc1Cl]

was placed in a milling apparatus (a 70 cm³ stainless steel ball mill container) with grinding compound in the form of 2.596 g of NH₄Cl, thereby providing the mixture at 14.5 and 85.5 weight % respectively, corresponding to 15 and 85 volume %, with a total volume of 2 cm³. Milling media comprising 40 g of 10 mm steel balls (10 pieces) were employed in the mill. Cooling was achieved with compressed air flow (100 kcpa). Milling time was 15 minutes and the composition resulting after milling comprised DCA in nanoparticulate form dispersed in NH₄Cl grinding compound.

Figure 5:
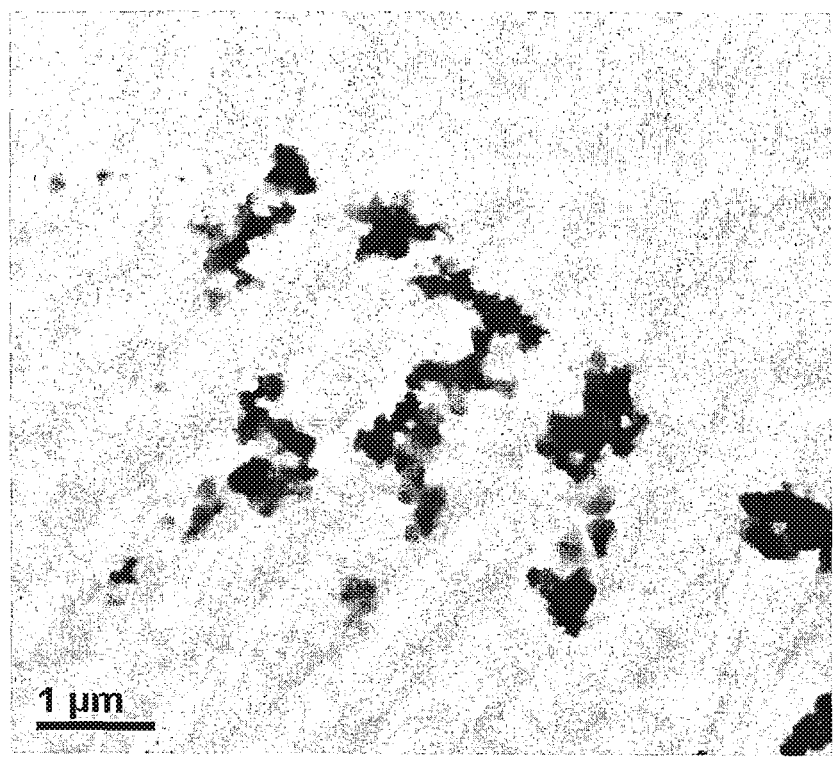
FIG. 5 is a TEM image of diclofenac acid milled with $NH_4Cl$ and washed with 0.1 M HCl and 1 mM CTAB, and dried on a TEM grid.
Figure 6:
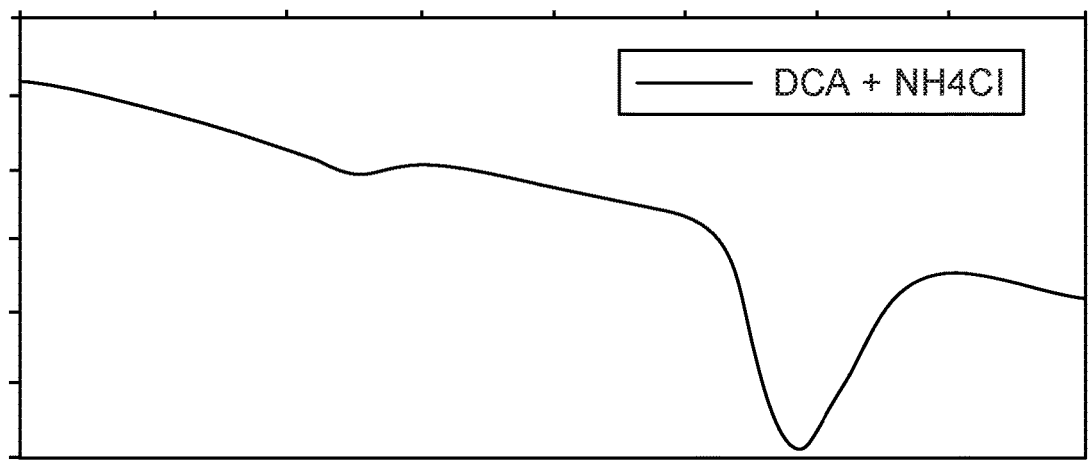
FIG. 6 plots heat flow against temperature for diclofenac acid dry milled with $NH_4Cl$ grinding compound, with the peak at 177° C. showing the presence of diclofenac acid, and the peak at 194° C. being due to the $NH_4Cl$ grinding compound.

The nanoparticle size can be seen from a representative TEM after washing (FIG. 5) and is about 200 nm in diameter (washing with 0.01 M HCl and 1 mM CTAB was performed as described for DCA NaCl milling). The melting point of DSC shows that the nanoparticles are obtained as the diclofenac acid (FIG. 6). The melting point of diclofenac acid is after literature at 182° C., one can see a melting point at 177° C., the shift is probably due to the small particles size. The large peak at 194° C. is due to NH₄Cl.

D. Raloxifene

In embodiments in which the particulate raloxifene, or pharmaceutically acceptable salt or solvate thereof, is produced using a method of the invention, and the method of the invention utilises a grinding compound, in a preferred form of the invention, the water-soluble diluent of the pharmaceutical composition is the same as the grinding compound used in the method. As would be understood by person skilled in the art, it may be desirable to add further quantities of the water soluble diluent to the particulate raloxifene hydrochloride for the purposes of preparing a pharmaceutical composition, relative to the quantity of grinding compound used in the method, or to remove some of the grinding compound prior to preparation of the composition.

In one form, the pharmaceutical composition of the invention is an oral dosage form comprising particulate raloxifene according to the invention, or pharmaceutically acceptable salt or solvate thereof, according to the invention, a surfactant in the form of CTAB, and a water-soluble diluent in the form of sodium chloride.

As a further embodiment of the invention, the particulate raloxifene, or pharmaceutically acceptable salt or solvate thereof, may be administered along with an effective amount of an additional therapeutic agent, including but not limited to estrogen, progestin, benzothiophene compounds including raloxifene, naphthyl compounds having antiestrogen activity, bisphosphonate compounds such as alendronate and tiludronate, parathyroid hormone (PTH), including truncated and/or recombinant forms of PTH such as, for example, PTH (1-34), calcitonin, bone morphogenic proteins (BMPs), or combinations thereof. The different forms of these additional therapeutic agents available as well as the various utilities associated with same and the applicable dosing regimens are well known to those of skill in the art.

Various forms of estrogen and progestin are commercially available. As used herein, the term "estrogen" includes compounds having estrogen activity and estrogen-based agents. Estrogen compounds useful in the practice of the present invention include, for example, estradiol estrone, estriol, equilin, equilenin, estradiol cypionate, estradiol valerate, ethynyl estradiol, polyestradiol phosphate, estropipate, diethylstibestrol, dienestrol, chlorotrianisene, and mixtures thereof. Estrogen-based agents, include, for example, 17-.alpha.-ethynyl estradiol (0.01-0.03 mg/day), mestranol (05-0.15 mg/day), and conjugated estrogenic hormones such as Premarin™ (Wyeth-Ayerst; 0.2-2.5 mg/day). As used herein, the term "progestin" includes compounds having progestational activity such as, for example, progesterone, norethynodrel, norgestrel, megestrol acetate, norethindrone, progestin-based agents, and the like. Progestin-based agents include, for example, medroxyprogesterone such as Provera™ (Upjohn; 2.5-10 mg/day), norethylnodrel (1.0-10.0 mg/day), and norethindrone (0.5-2.0 mg/day). A preferred estrogen-based compound is Premarin™, and norethylnodrel and norethindrone are preferred progestin-based agents. The method of administration of each estrogen- and progestin-based agent is consistent with that known in the art.

Use for Alleviating Pathologies

As stated in the summary, the present invention further provides the use of the said particulate raloxifene, or pharmaceutically acceptable salt or solvate thereof, in the manufacture of a medicament for alleviating pathologies, including osteoporosis, serum lipid lowering, and inhibiting endometriosis, uterine fibrosis, and breast cancer, and the use of compositions comprising or formulated using the said particulate raloxifene, or pharmaceutically acceptable salt or solvate thereof, for alleviating pathologies, including osteoporosis, serum lipid lowering, and inhibiting endometriosis, uterine fibrosis, and breast cancer.

The present invention provides a method for the treatment of a pathology, such as osteoporosis, serum lipid lowering, and inhibiting endometriosis, uterine fibrosis, and breast cancer by administration of a therapeutically effective amount of particulate raloxifene, or pharmaceutically acceptable salt or solvate thereof, according to the invention.

The particular dosage of particulate raloxifene, or pharmaceutically acceptable salt or solvate thereof, required to treat, inhibit, or prevent the symptoms and/or disease of a mammal, including humans, suffering from the above maladies according to this invention will depend upon the particular disease, symptoms, and severity, as well as the potential increased efficacy due to particulate form of the raloxifene, or pharmaceutically acceptable salt or solvate thereof, (e.g., increased solubility, more rapid dissolution, increased surface area).

Amounts effective for such a use will depend on: the desired therapeutic effect; the route of administration; the potency of the therapeutically active agent; the desired duration of treatment; the stage and severity of the disease being treated; the weight and general state of health of the patient; and the judgment of the prescribing physician.

Generally, accepted and effective doses will be from 15 mg to 1000 mg, and more typically from 15 mg to 80 mg. Such dosages will be administered to a patient in need of treatment from one to three times each day or as often as needed for efficacy, generally for periods of at least two months, more typically for at least six months, or chronically.

As discussed above, the particulate raloxifene, or pharmaceutically acceptable salt or solvate thereof, of this invention can be administered by a variety of routes, the selection of which will be decided by the attending physician.

The raloxifene compounds of the current invention may be made according to established procedures, such as those detailed in U.S. Pat. Nos. 4,133,814, 4,418,068, and 4,380,635, and European Patent Application 95306050.6, Publication No. 0699672, Kjell, et al., filed Aug. 30, 1995, published Mar. 6, 1996, all of which are herein incorporated by reference. In addition, the information disclosed in the published European Patent Application number 0670162 A1, published on Sep. 6, 1995, is herein incorporated by reference.

Methods for the preparation of amorphous raloxifene salts and specific pharmaceutically acceptable salts are discussed earlier in this specification.

D1. Raloxifene HCl

Conventional active pharmaceutical compound raloxifene hydrochloride (0.5805 g) was introduced with NaCl (5.5208 g) into a steel vessel (75 cm$^3$) with milling bodies comprising 10×10 mm steel balls. The total volume of the raloxifene hydrochloride/salt mixture was 3 cm$^3$ with 15 vol % of drug. Both the raloxifene hydrochloride and the sodium chloride grinding compound were kept dry prior to milling by storage under vacuum and over $P_2O_5$. The steel milling chamber was closed under vacuum to remove moisture and air, to reduce degradation/oxidization.

The milling chamber was mounted on a Spex ball mill and was shaken for 15 min and cooled by a stream of compressed air. This resulted in the formation of a solid-dispersion consisting of raloxifene hydrochloride dispersed within a matrix of fine NaCl.

The milling chamber was then carefully opened to release the vacuum, and closed to allow any airborne particles to settle. The milling chamber was then opened in a fume hood to prevent inhalation of the fine particles, and the contents transferred through a 2 mm sieve (to remove the milling bodies) into 8 mL glass vials and stored in a vacuum desiccator over $P_2O_5$.

To remove the sodium chloride from the milled raloxifene hydrochloride, the solid-dispersion was washed as follows. The solid dispersion was mixed with 0.1 g of the surfactant CTAB, and placed in a 25 mL Schott bottle. 20 mL of ice cooled solution of 0.1 M HCl and 1 mM cetyl trimethyl ammonium bromide (CTAB) were added. The bottle was closed and immediately mounted in the Spex ball mill and shaken for 3 minutes. After the shaking procedure a pale yellow dispersion formed, and stored in an ice bath prior to centrifugation. The sample was then subjected to the following (3×): centrifugation (the centrifugation speed was increased for each washing step from 6000 g to 8000 g and finally to 12000 g for a period of 3 minutes each), removal of supernatant, addition of 0.01 M HCl and 1 mM CTAB, and redispersion by vortex mixing.

The dispersion was then transferred onto a watch glass and dried over a stream of air. After drying for about 3 hours the suspension dried down to form a dry layer on the glass surface, this was stored over night in a vacuum desiccator over $P_2O_5$. This yielded 0.48 g of dried powder which was stored in a glass vial in a vacuum desiccator.

The dissolution properties of the particulate raloxifene hydrochloride were tested with a USP apparatus in simulated gastric conditions, and compared with commercial raloxifene hydrochloride. About 60 mg of particulate raloxifene hydrochloride and commercial raloxifene hydrochloride, respectively, were introduced into gelatin capsules. The dissolution properties were followed as a function of solution concentration versus time.

The dissolution conditions were as follows: 1L of 0.1 M HCl containing 2 g of NaCl were degassed and brought to 37° C. in a USP conform dissolution vessel to paddle and stirred at about 80 rpm. The raloxifene hydrochloride was either tested as powder or in gelatin capsule with a metal sinker. For each time point, 2 mL of sample were removed from the solution, to remove larger aggregates it was centrifuged for 1 min at 10000 g and 1.5 ml was taken from the top of the solution and the concentration was measured using a Waters HPLC running a method validated with respect to specificity, linearity, precision and repeatability.

Figures 8A, 8B:
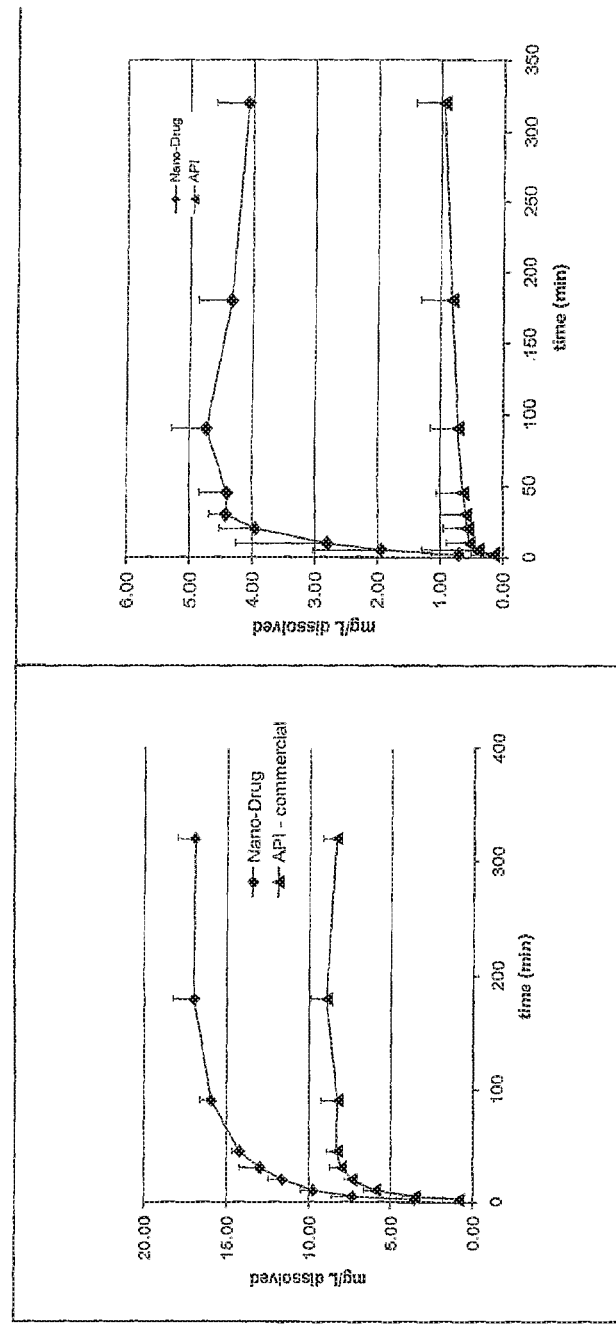
FIG. 8 is a comparison of the dissolution profiles of particulate raloxifene hydrochloride of an embodiment of the invention and commercial raloxifene hydrochloride in simulated gastric fluid and in simulated intestinal fluid.

The dissolution profile in FIG. 8 shows significantly enhanced solubility properties of the particulate raloxifene hydrochloride as opposed to the commercial raloxifene hydrochloride, this can be seen for example in a nearly five fold increase in solution concentration after 50 minutes in simulated intestinal fluid. To understand these data it needs to be emphasized that the conditions were kept close to the marketed dosage of raloxifene and the concentration of 60 mg of drug per liter are well above the solubility.

Figure 9A:
FIGS. 9a through 9d are scanning electron micrographs comparing particulate raloxifene hydrochloride of an embodiment of the invention and commercial raloxifene hydrochloride.
Figure 9B:
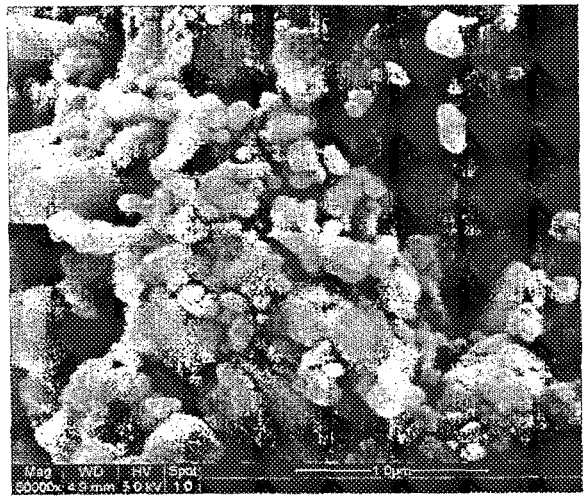
Figure 9C:
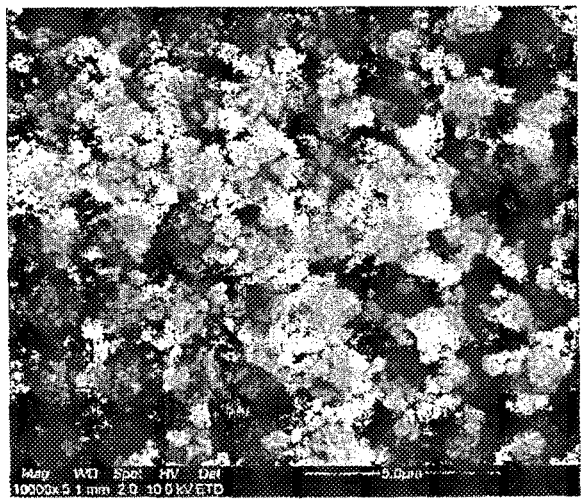
Figure 9D:
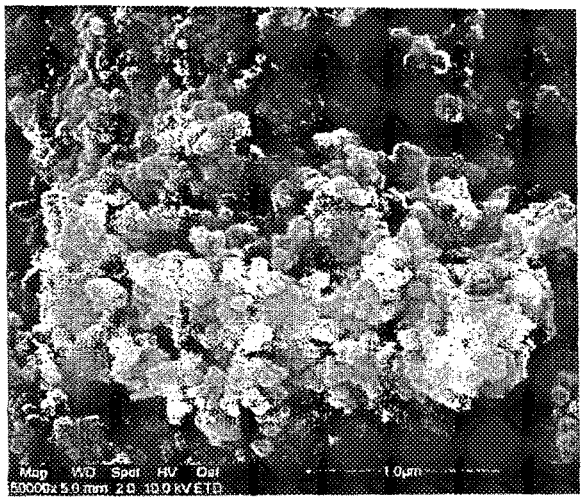

As can be seen from the scanning electron micrographs in FIG. 9a, the commercial raloxifene HCl particles seem to have a broad size distribution with glassy particles of up to several micrometers. After salt milling of raloxifene HCl with NaCl, small structures in the size of about 100-200 nm are a predominant feature (FIG. 9b). After the washing procedure and drying, small structures can be attributed to raloxifene HCl particles (as the salt matrix was removed by washing), the particle-like structures show a size of about 100-200 nm (FIGS. 9c and d).

Figure 10:
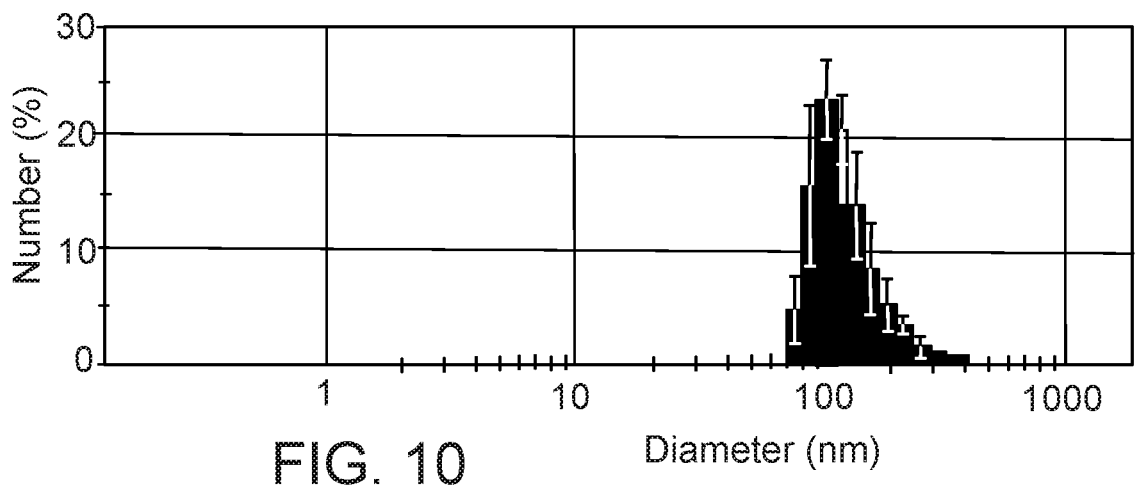
FIG. 10 illustrates a size distribution of particulate raloxifene hydrochloride of an embodiment of the invention determined by dynamic light scatter (DLS)

The size determined by SEM is in good agreement with the size distribution of the dispersion before drying by dynamic light scatter (DLS) (FIG. 10). Here the particles size was determined with a Malvern HPPS dynamic light scattering apparatus with a size distribution after number of 128±53 nm (number weighted) in intensity a second peak of 300 nm was detected. Prior to the measurement any larger aggregates or agglomerates were removed by 1 min centrifugation at 6000 g, and only the supernatant was analyzed. This indicates that the particles obtained in the milling process did not significantly grow during the washing procedure.

Further evidence for the decreased particles size after milling and washing are the BET surface area which increased from 0.1 m$^2$/g for the commercial raloxifene HCl to about 7 to 20 m$^2$/g for the particulate raloxifene hydrochloride, which can be explained by the increased surface to mass ratio as the particles' diameter decreases. Surface areas for various examples are tabulated below.

| sample No. | BET surface area |
| --- | --- |
| 169AW | 15.6517 ± 0.0332 m$^2$/g |
| 169BW | 17.0576 ± 0.0368 m$^2$/g |
| 171AW | 16.6507 ± 0.0297 m$^2$/g |
| 171BW | 15.0311 ± 0.0244 m$^2$/g |
| 172AW | 18.7621 ± 0.0373 m$^2$/g |
| 172BW | 21.1382 ± 0.0323 m$^2$/g |
| 174AW | 13.9266 ± 0.0320 m$^2$/g |
| 174BW | 17.9952 ± 0.0317 m$^2$/g |
| 175AW | 16.7377 ± 0.0199 m$^2$/g |
| 175BW | 25.1960 ± 0.0502 m$^2$/g |
| 176AW | 20.6579 ± 0.0400 m$^2$/g |
| 176BW | 11.9100 ± 0.0221 m$^2$/g |
| 3011AW | 10.1126 ± 0.0295 m$^2$/g |
| 3013BW | 7.0471 ± 0.0202 m$^2$/g |
| 3016AW | 9.1337 ± 0.0394 m$^2$/g |
| 3011BW | 10.505 ± 0.0290 m$^2$/g |

-continued

| sample No. | BET surface area |
|---|---|
| 1177AW | 9.1774 ± 0.0435 m²/g |
| 3016BW | (samples combined) |
| 3017BW | |
| 3013AW | |
| 177B15 | |

Figure 11:
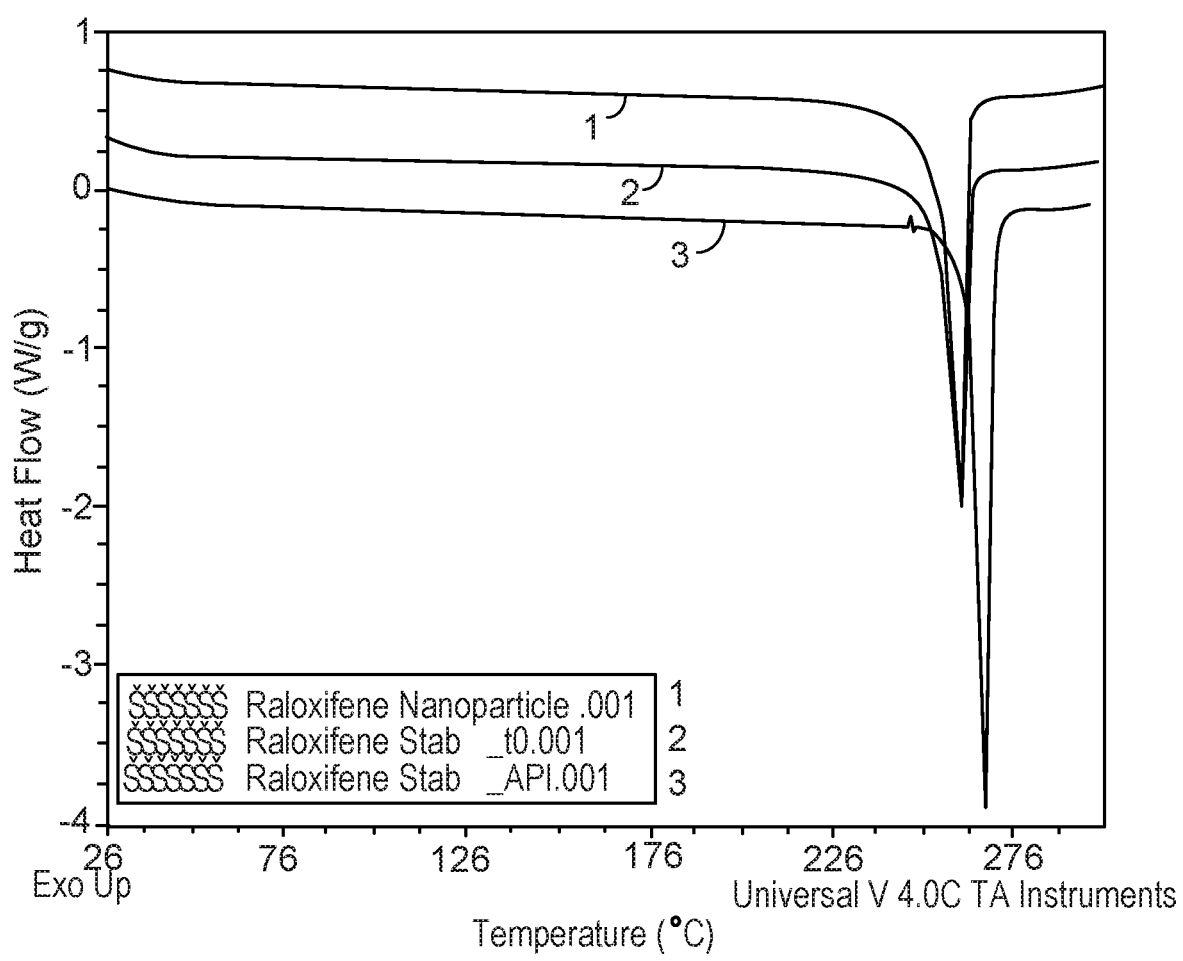
FIG. 11 compares melting points of particulate raloxifene hydrochloride of an embodiment of the invention and commercial raloxifene hydrochloride.

The melting point shows a ten degree Celsius reduced onset for nanoparticulate raloxifene HCl, as compared to the commercial product, being further evidence for a reduced particle size (FIG. 11).

Figure 12:
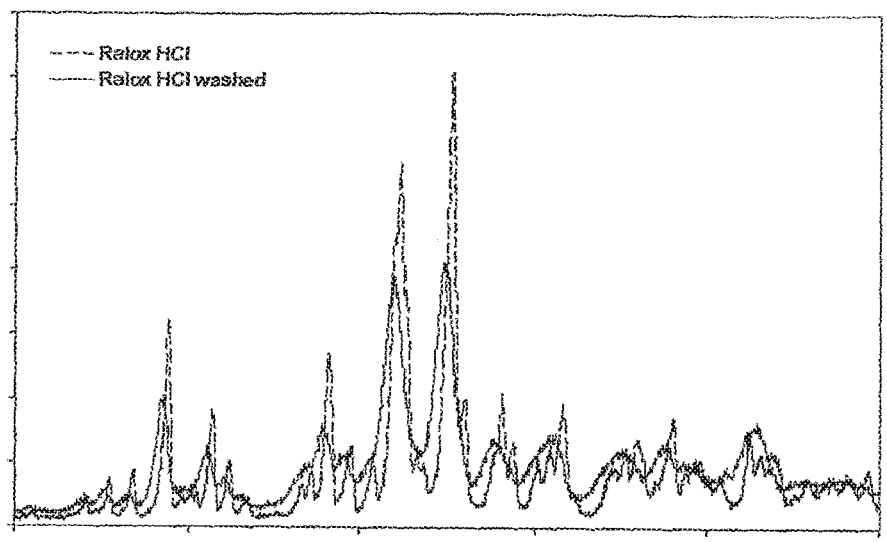
FIG. 12 compares XRD-spectra for particulate raloxifene hydrochloride of an embodiment of the invention and commercial raloxifene hydrochloride.

The XRD-spectra (FIG. 12) shows that the nanoparticulate raloxifene HCl appears to be in the same crystalline phase as the commercial raloxifene HCl, and suggest that the particles remain crystalline. The relative broadening of the peaks of the nanoparticles raloxifene as compared to the commercial raloxifene is a further indicator of the reduced particles size.

Figure 13:
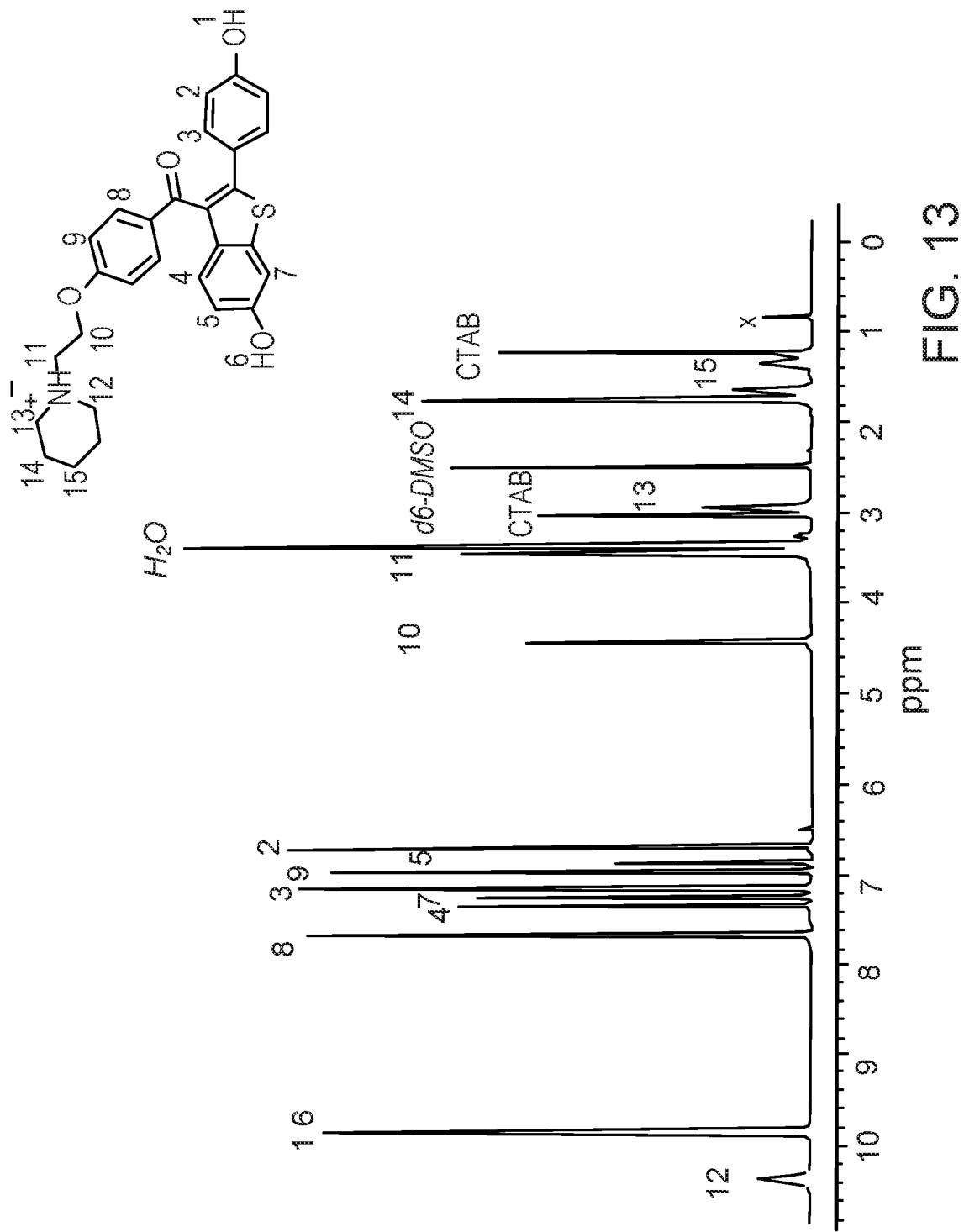
FIG. 13 is a solution $^1$H-NMR spectrum for particulate raloxifene hydrochloride of an embodiment of the invention.

The solution $^1$H-NMR-spectra, shown in FIG. 13, confirms that the compound is identical to the commercial raloxifene HCl, it was also determined that about 2 w % of the surfactant CTAB are present after washing and drying. The solution $^1$H NMR spectra were measured of about 10 mg of particulate raloxifene HCl and commercial raloxifene HCl (data not shown) dissolved in d6-DMSO.

The FT-IR-spectra (FIG. 14) shows further the chemical identity of raloxifene HCl and the nanoparticulate raloxifene HCl.

The salt content after washing was negligible, and as determined by ICP measurements, only about 0.65 w % of NaCl remained, while the commercial sample showed with about 0.08 w % NaCl not significantly lower salt concentrations. This observation was also supported by the disappearance of the NaCl pattern in the XRD-spectra of the sample after washing as compared to the sample directly after salt milling (data not shown).

Figure 14:
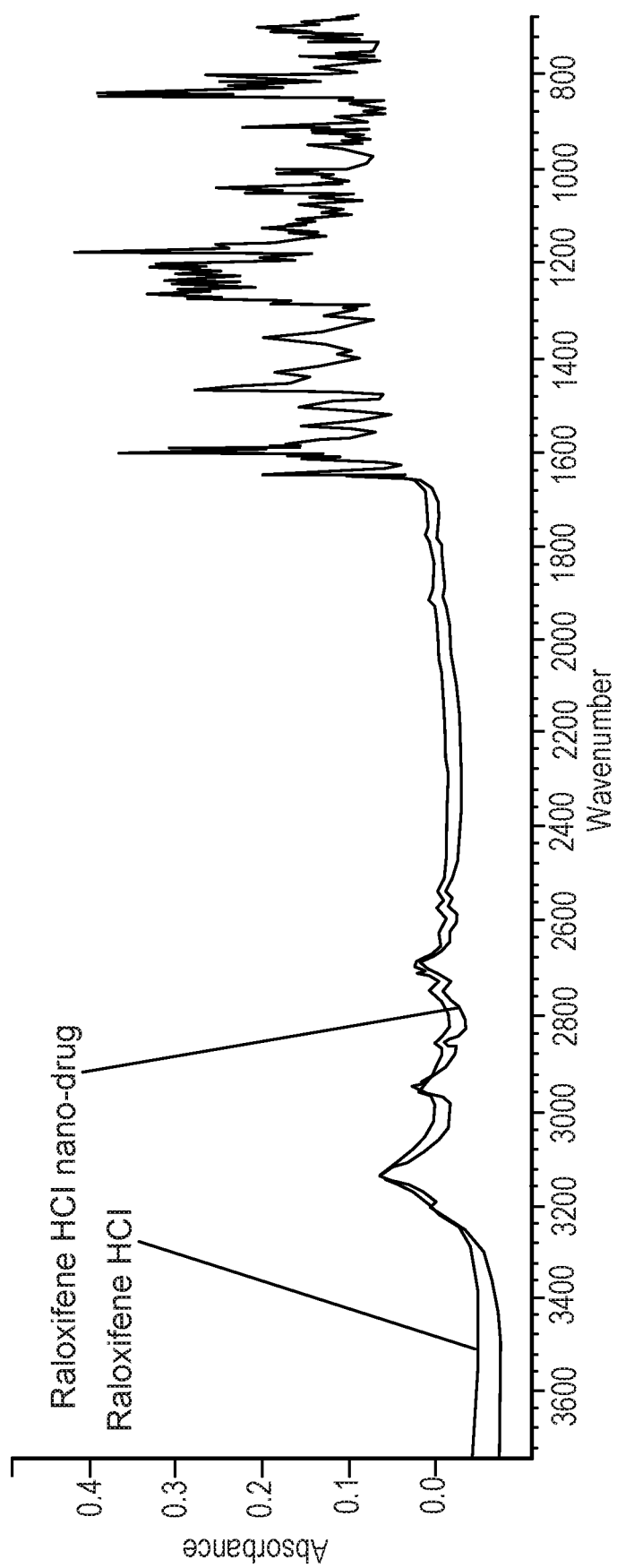
FIG. 14 compares the FT-IR spectra of particulate raloxifene hydrochloride of an embodiment of the invention with commercial raloxifene hydrochloride.

The chemical identify of the raloxifene HCl was further confirmed by the similarity of the IR-spectra, which is nearly identical. This also confirms that the amount of CTAB after washing is quite small (FIG. 14). Nevertheless the reversal of the Zeta-potential seems to indicate that the surfactant does play an important role as well.

D2. Raloxifene HCl (Amorphous)

Conventional active pharmaceutical compound raloxifene hydrochloride (0.3867 g) was introduced with NaCl (3.672 g) into a steel vessel (75 cm$^3$) with milling bodies comprising 10×10 mm steel balls. The total volume of the raloxifene hydrochloride/salt mixture was 2 cm$^3$ with 15 vol % of drug. Both the raloxifene hydrochloride and the sodium chloride grinding compound were used without any additional drying step prior to the milling. The steel milling chamber was closed under vacuum to remove moisture from the air, and to reduce degradation/oxidization.

The milling chamber was mounted on a Spex ball mill and was shaken for 15 min and cooled by a stream of compressed air. This resulted in the formation of a solid-dispersion consisting of raloxifene hydrochloride dispersed within a matrix of fine NaCl.

The milling chamber was then carefully opened to release the vacuum, and closed to allow any airborne particles to settle. The milling chamber was then opened in a fume hood to prevent inhalation of the fine particles, and the contents transferred through a 2 mm sieve (to remove the milling bodies) into 8 mL glass vials and stored in a vacuum desiccator over P2O5.

To remove the sodium chloride from the milled raloxifene hydrochloride, the solid-dispersion was washed as follows. About 4.1 g of the solid dispersion was placed in a 25 mL Schott bottle, and added 20 mL of ice cooled solution of 0.1 M HCl and 1 mM sodium dodecyl sulfate (SDS) was added. The bottle was closed and immediately mounted in the Spex ball mill and shaken for 1 min. After the shaking procedure a pale yellow dispersion was formed, and stored in an ice bath prior to centrifugation. The sample was then subjected to a centrifugation step at 6000 g for a period of 3 minutes, and the supernatant was removed. The sample was dispersed with 4 mL of 0.1 M HCl and 1 mM SDS solution.

The dispersion was then transferred onto a watch glass and dried over a stream of air. After drying for about 3 hours the suspension dried down to form a dry layer on the glass surface, this was stored over night in a vacuum desiccator over $P_2O_5$.

Figure 15:
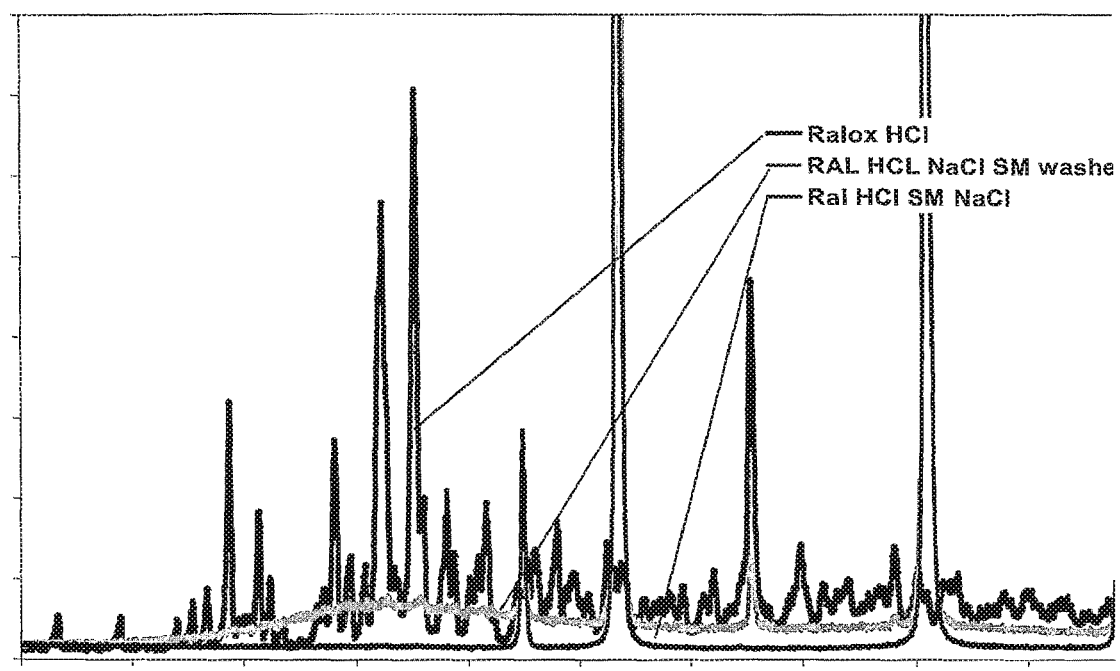
FIG. 15 compares XRD spectra of raloxifene hydrochloride at various stages of processing according to a method of the present invention.

The XRD shows that after milling and washing the crystal structure of raloxifene HCl is lost, and the broad increase in intensity from 10 to 35 (2 Theta) is indicative for an amorphous phase (FIG. 15). The XRD spectrum shows the different processing stage, before milling, after milling, and after washing. The commercial Raloxifene HCl shows distinct peaks that are due to its crystalline state. Prevalent peaks after salt milling are mostly due to sodium chloride and the usage of an aluminium sample holder, the peaks of raloxifene HCl can not be identified, as they are too dilute in the matrix. After the one washing step some peaks of the sodium chloride remain, but only a broad band of raloxifene HCl can be seen, which can be attributed to amorphous phase.

There are only a few peaks related to raloxifene HCl crystals pertained, indicating that some crystal order is formed. The XRD spectra also shows some that there is still some sodium chloride remaining in the sample, as can be seen from the peaks at about 27(2 Theta).

Figure 16:
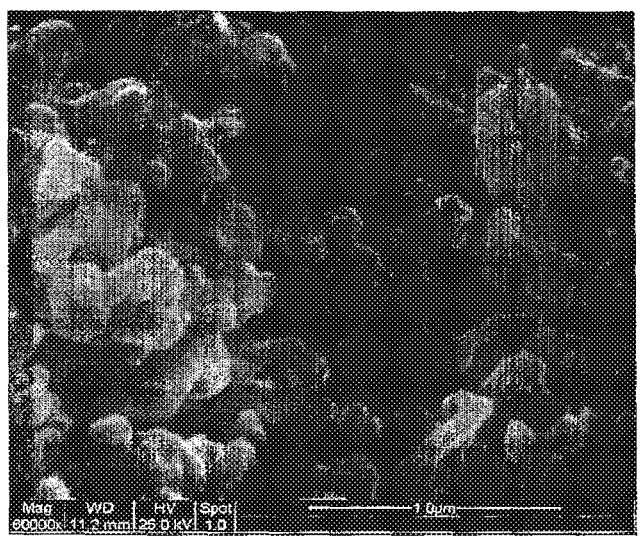
FIG. 16 is a scanning electron micrograph of particulate raloxifene hydrochloride according to an embodiment of the invention.

The SEM shows that some small particles were formed with a size of about 100-200 nm. Some of the particles seem to be slightly elongated (FIG. 16).

The BET surface area was measured to be 10.6 m$^2$/g, which confirms that a material with high surface was formed and supports results from the SEM image.

Figure 17:
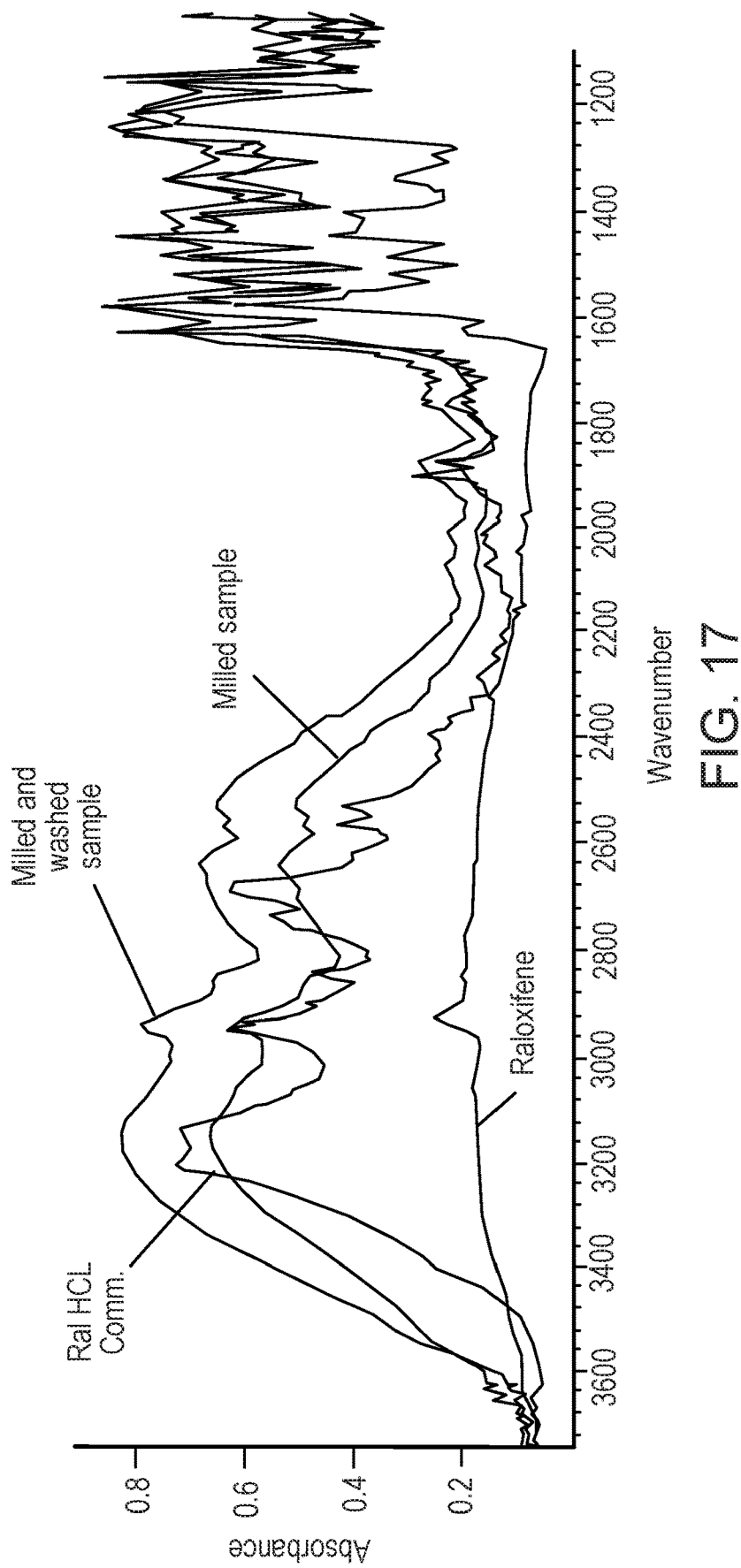
FIG. 17 compares FT-IR spectra of raloxifene hydrochloride at various stages of processing according to an embodiment of the method of the present invention.

The IR-spectra, in particular the peak at 2960 cm$^{-1}$, indicates that raloxifene HCl salt is present in the in both the milled and milled and washed samples (FIG. 17). Some peaks are less pronounced then in the pure raloxifene HCl spectra, but this might be due to the remaining salt.

D3. Raloxifene Free Base 0.3640 g Raloxifene free base and 3.6725 g NaCl (20 vol % drug) was milled with 10 pieces of 10 mm steel balls for 15 min at room temperature.

Figure 18A:
FIG. 18 is a scanning electron micrograph of raloxifene (free base) as obtained (a and b) and after processing by milling with sodium chloride (c and d).
Figure 18B:
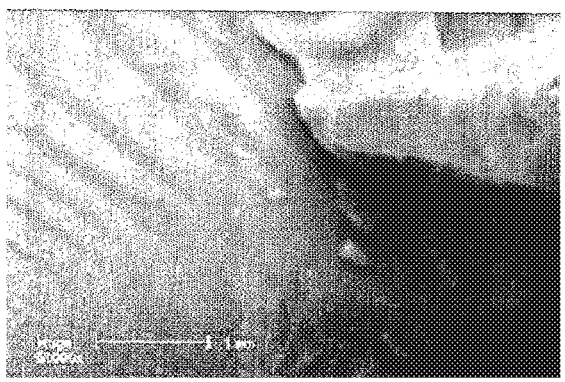
Figure 18C:
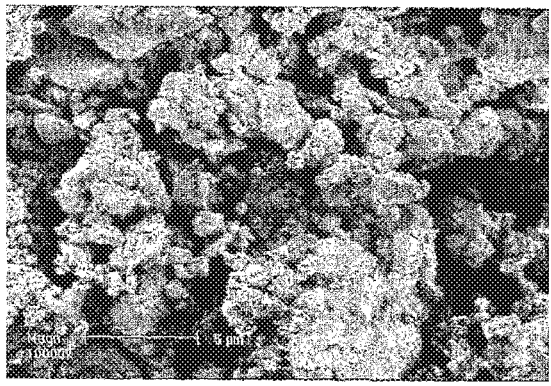
Figure 18D:
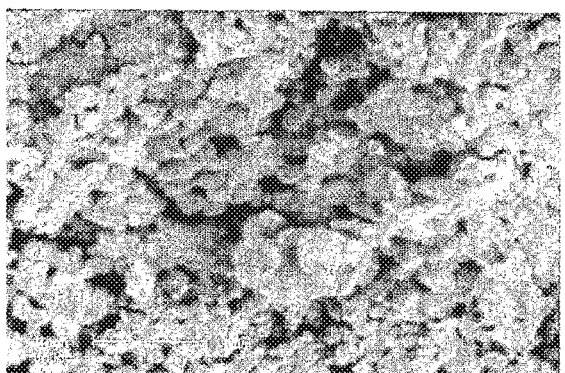

The SEM of the starting shows large pieces of glassy looking raloxifene base, and has no fine structure, but is very smooth (FIGS. 18a and b). The SEM after salt milling shows in contrast a fine structure with small particles of about 100 nm in diameter that form larger agglomerates (FIGS. 18c and d). The particles are looking uniform in shape and no difference between salt or drug can be observed.

After ball milling the salt was largely removed by dispersion in a buffer of pH 9, at which the solubility of raloxifene is very low, but NaCl would dissolve (0.01 M TRIS-Buffer, pH adjusted with HCl) (TRIS: (tris(hydroxymethyl)aminomethane hydrochloride). To colloidally stabilize the particles and to prevent aggregation the nonionic surfactant Plasdone® S-630 (0.5 g/mL) and the ionic surfactant sodium dodecyl sulphate SDS (0.2 mM) were added (FIG. 19). The dispersion was stirred in 50 mL of the before mentioned mixture with a magnetic stirrer bar for 15 min, followed by a few seconds of ultrasonication in a water bath.

The dispersion was then washed by centrifugation using 15 mL Falcon tubes and a centrifugation speed of 5,000 g. The supernatant was discarded and the sediment was dispersed with 30 mL of 0.01 M Tris-buffer (pH 9) and 1 mM SDS by shaking. A further centrifugation at 5,000 g followed and the pellet was dispersed with 3 mL of 0.01M Tris (pH 9) and 1 mM SDS.

The dispersion was dried over a nitrogen stream and the vacuum dried. The SEM image in FIG. 20 reveals a fine structure on the nanoscale, which shows structures of under 100 nm. The particles seem to have dried in a network like structure, probably bridged by the polymeric surfactant Plasdone.

The BET surface area indicated a very large surface area of $57.7178 \pm 0.4095$ $m^2/g$. Calculating with a density of 1.3 $g/cm^3$, and assuming monodispersed nanoparticles, the particles diameter with such a surface area would be about 80 nm. (For a density of 1.2 $g/cm^3$: 85 nm and for 1.4 $g/cm^3$, 70 nm).

Figure 21:
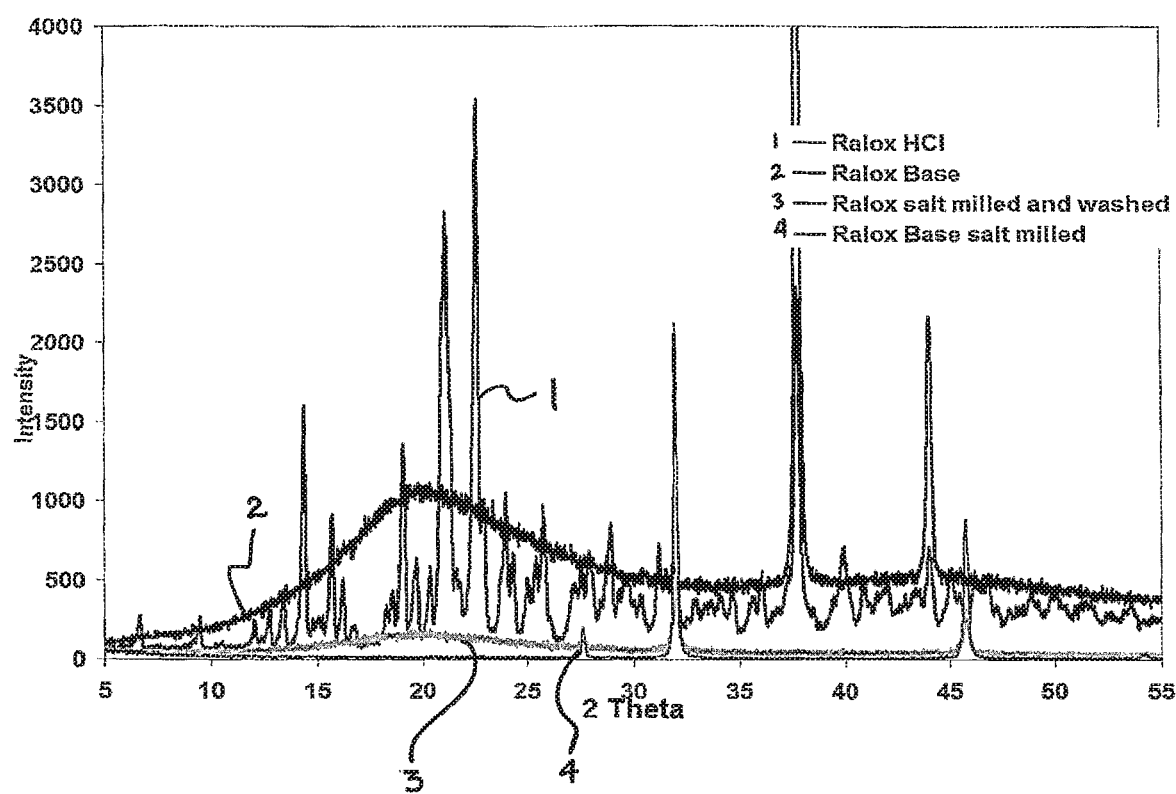
FIG. 21 compares XRD spectra of raloxifene (free base) at various stages of processing according to a method of the present invention.

The XRD shows that the raloxifene base is amorphous and the resulting product after washing is likewise amorphous, it also shows the distinctly different peaks to the raloxifene HCl salt (FIG. 21). The powder XRD shows that raloxifene (ralox) free base is retained after milling and washing. The spectra of the salt milling sample is dominated by the strong peak of NaCl; after washing the lower intensity of the NaCl peaks shows that the amount of NaCl is greatly reduced and reveals the amorphous phase of raloxifene free base. The raloxifene free base seems to contain still a small amount of NaCl, as compared to the sample directly after salt milling before the salt matrix was removed.

Figure 22:
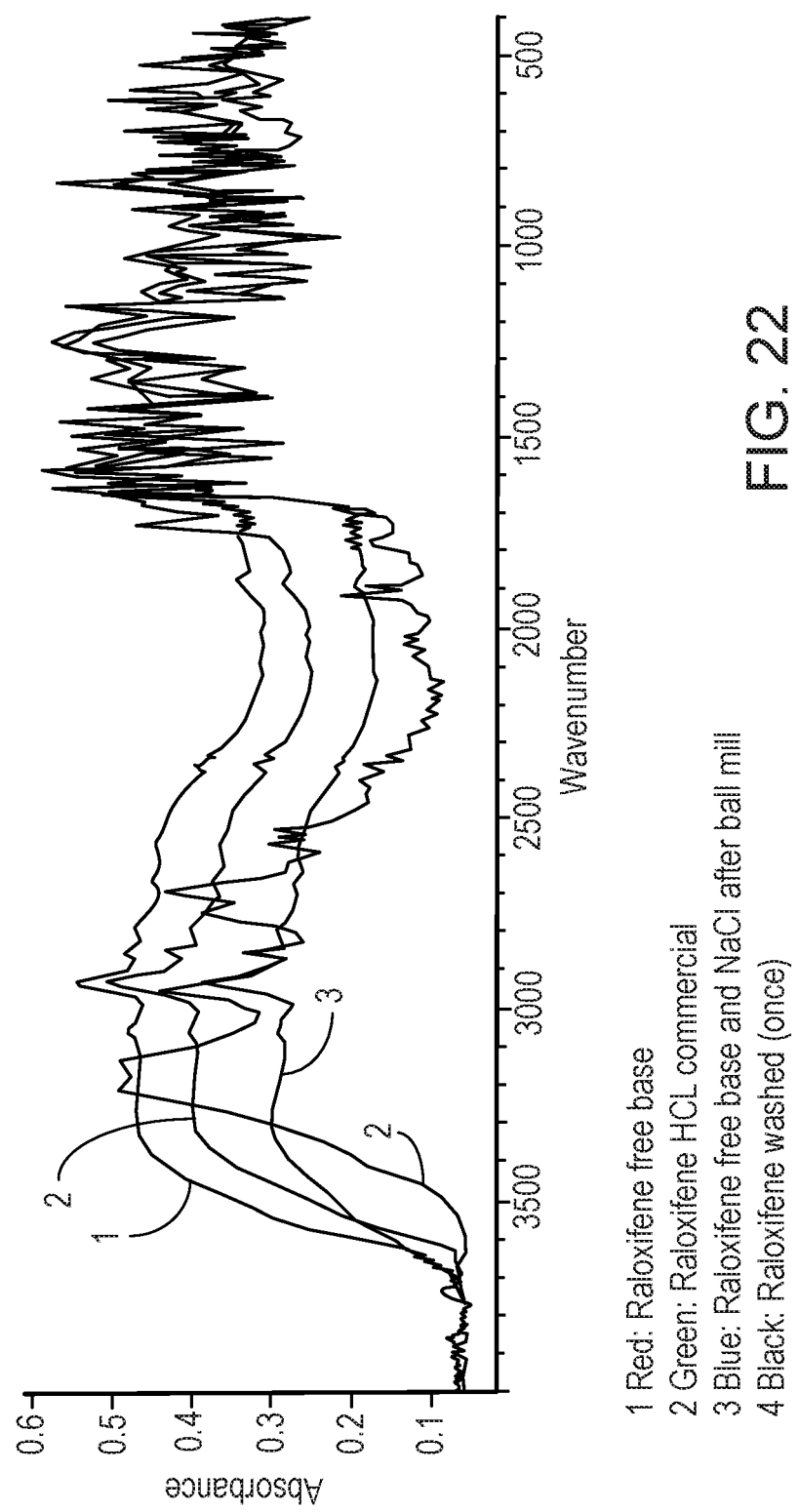
FIG. 22 compares FT-IR spectra of raloxifene hydrochloride at various stages of processing according to an embodiment of the method of the present invention.
Figure 23A:
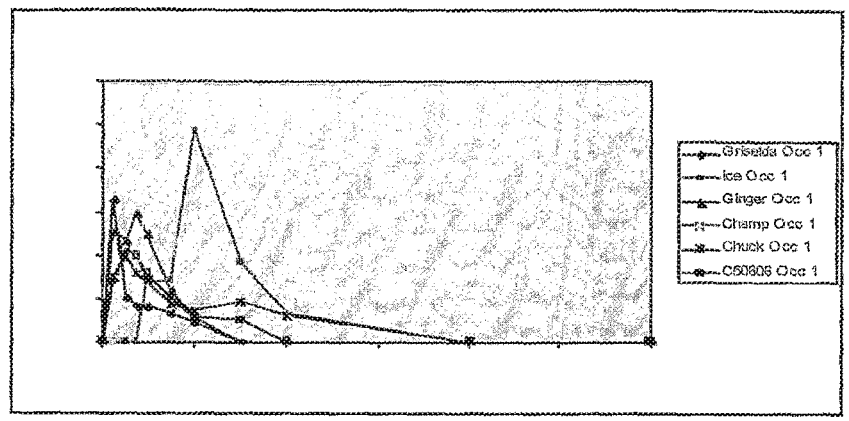
FIG. 23 provides concentration v time data for animal experiments comparing particulate raloxifene hydrochloride of an embodiment of the invention and commercial raloxifene hydrochloride.
Figure 23B:
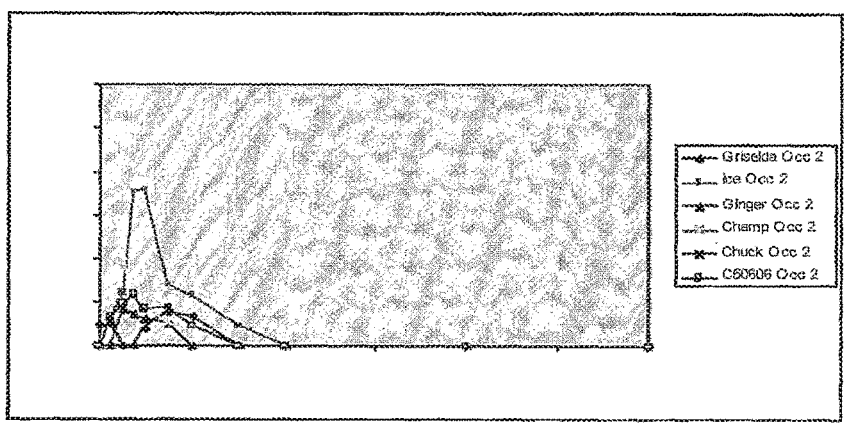
Figure 23C:
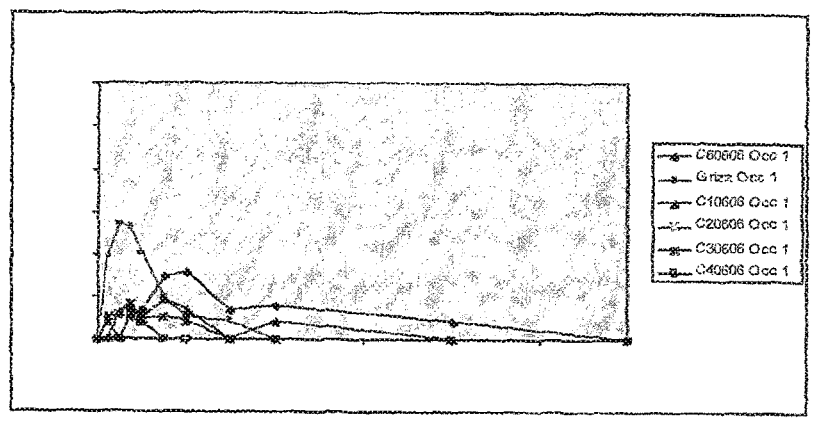
Figure 23D:
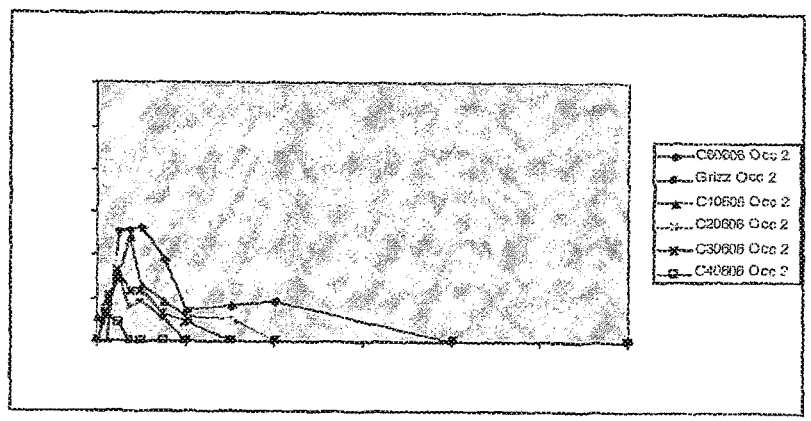

By diffuse reflection IR it was shown that the free base is retained after ball milling and after dissolution of the matrix (FIG. 22), as the peak at about 2900 $cm^{-1}$ indicates. After dissolution of the matrix the additional peak at about 1750 $cm^{-1}$ is most probably due to the non-ionic surfactant Plasdone S-630, which probably covers the surface of the nanoparticles.

It can be concluded that sub 100 nm particles of amorphous raloxifene free base, coated with the non-ionic surfactant Plasdone can be formed.

D4. Animal Studies

This study involved the investigation of the pharmacokinetics of raloxifene hydrochloride following oral administration of two dosage formulations to 12 male and female beagle dogs. The two dosage forms investigated were 1) raloxifene hydrochloride particles, developed according to the method of the present invention, and 2) standard API. Both forms were administered as capsules prepared by the Pharmaceutics laboratory of TetraQ.

As tested prior to administration to the dogs, the particulate raloxifene hydrochloride had the following properties: >75% of the particles were in the range of 220-350 nm in size, with >90% in the range of 160-342 nm. Differential scanning calorimetry, or DSC, showed an approximate 10° C. reduction in the onset of melting as compared to the comparison API. Dissolution of the particulate raloxifene under standard conditions in simulated gastric fluid and simulated intestinal fluid (60 mg in 1 L fluid) showed a significant increase in dissolution as compared to the comparison API. At 90 minutes post addition, approximately 15 mg/L of particulate raloxifene was detected versus 8 mg/L of comparison API for SGF; and 4.5 mg/L versus 0.75 mg/L for SIF.

Note that a less significant increase was observed when samples had not been subjected to brief grinding using a mortar and pestle. Grinding had no effect on the dissolution profile of the comparison API, however increased both dissolution rate and solubility for the raloxifene hydrochloride. This is consistent with the presence of loose agglomerates in the particulate raloxifene, but not the comparison API.

The study was designed as a crossover trial conducted in 6 male and 6 female healthy Beagle dogs. Raloxifene was administered as an oral dose with three male plus three female dogs each receiving one of the two preparations on each of two dosing occasions. Eleven plasma samples were collected from each animal in the 24 hour period following each dose and these were all available for determination of raloxifene concentration.

Plasma samples were transported to the TetraQ-ADME laboratories on dry ice and all were in an intact (frozen) condition upon arrival. The concentration of raloxifene in the plasma samples was determined by an LC-MS/MS assay developed and validated by TetraQ-ADME.

Pharmacokinetic analysis was performed using purpose-written macros for Excel Software. Standard model-independent pharmacokinetic methods were used.

Nominal sampling times were used in the calculations. The plasma raloxifene concentrations were used to determine the following parameters:

(i) $C_{max}$ Maximum plasma concentration, read directly from the raw data.
(ii) $T_{max}$ Time at which $C_{max}$ was achieved, also read directly from the raw data.
(iii) $k_e$ Terminal elimination rate constant, which was determined as the slope of the regression line of best fit to the approximately log-linear terminal elimination phase (using the least squares linear regression function in the Excel 2003 software). The data from the final three or four measurable concentrations were used in the regression analysis for all data sets.
(iv) $t_{1/2}$ Terminal elimination half-life=ln $2/k_e$
(v) $AUC_{0-t}$ Area under the plasma concentration-time curve from time zero to the time of the last measurable raloxifene concentration above the lower limit of quantitation of the assay, determined by trapezoidal rule integration. Concentration values less than the lower limit of quantification (LLOQ) which occurred prior to the first measurable concentration were set to zero.
(vi) $AUC_{t-\infty}$ Area under the plasma-concentration-time curve from the time of the last measured plasma concentration to infinity, as determined by the formula $C_t/k_e$, where $C_t$ is the concentration value calculated on the line of best fit at the time when the last measured plasma concentration occurred, and $k_e$ is the terminal elimination rate constant as defined above.
(vii) $AUC_{0-\infty}$ Sum of $AUC_{0-t}$ and $AUC_{t-\infty}$.

Figures 24A, 24B:
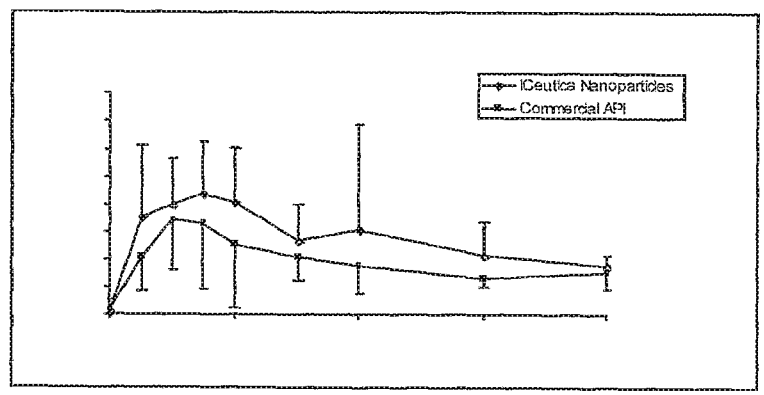
FIG. 24 provides the data of FIG. 16 in graphical and tabular form.

The individual subject data have been plotted using linear concentration scales and are presented in FIG. 23. The iCeutica raloxifene HCl nanoparticles are generally labelled as Test Substance 1 and the commercial available raloxifene HCl is labelled as Test Substance 2. The mean±SD values at each nominal sampling time for each dosing group are shown in tabular and graphical form in FIG. 24.

Figure 26B:
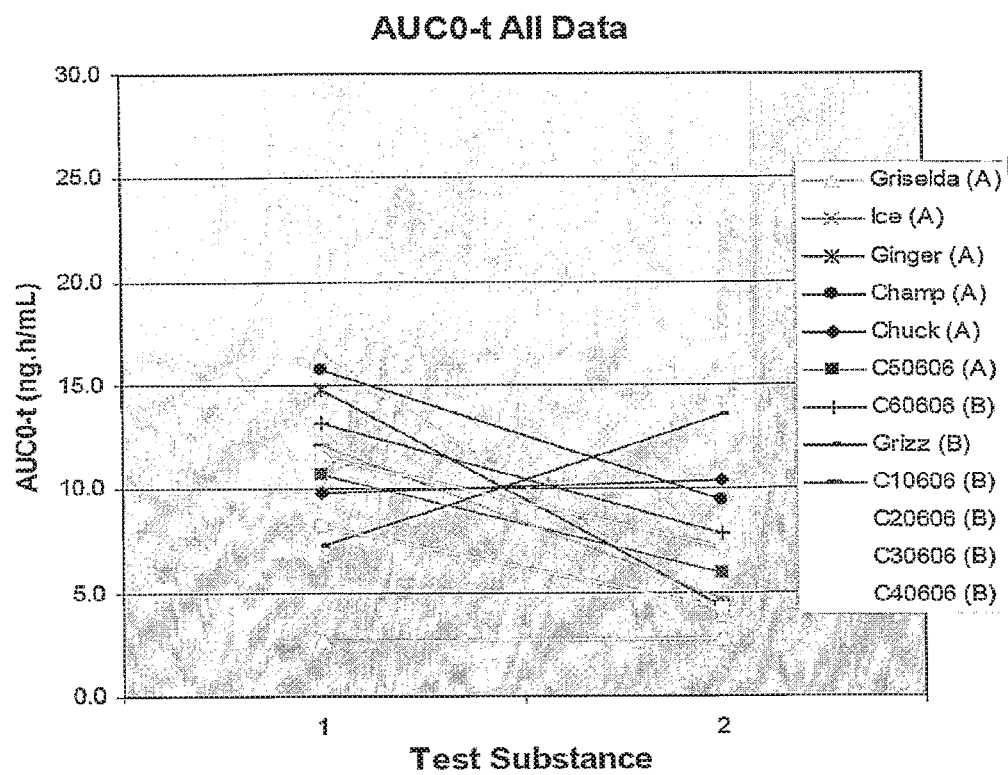
FIG. 26 provides an additional comparison of $C_{max}$ and $AUC_{0-t}$ results.
Figure 26C:
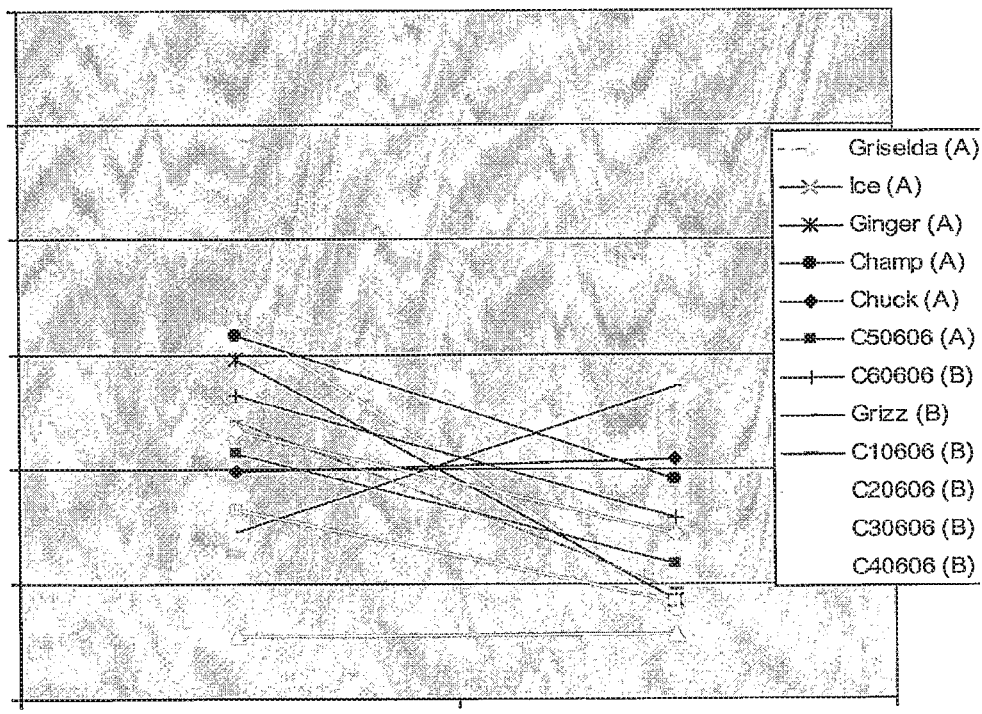

Mean±SD data for each dosing group are displayed in FIG. 25. An additional comparison is made for $C_{max}$ and $AUC_{0-t}$ results for the two dosing groups in FIG. 26.

Administration of the particulate raloxifene HCl resulted in an approximate 59% increase in maximum plasma concentration ($C_{max}$) and 56% increase in area under the concentration vs. time curve ($AUC_{0-t}$) compared with those following administration of the commercial API (12.26±5.47 and 7.69±4.54 ng/mL, and 33.39±20.54 and 21.36±16.79 ng.h/mL, respectively). In addition, the median time to maximum concentration ($T_{max}$) was shorter (1.00 vs. 1.50 hours, respectively) following the administration of the particulate raloxifene HCl compared with that following administration of the commercial API.

Analysis of $AUC_{0-t}$ and $C_{max}$ data for individual animals showed all to follow a pattern of higher results following administration of the particulate raloxifene HCl compared to the commercial API, except those for one female animal, for which lower results were obtained for $AUC_{0-t}$ and $C_{max}$ following administration of the particulate raloxifene HCl. The results for this dog were clearly inconsistent with those for the other animals; however no explanation can be offered for this apparent inconsistency in results.

The variation between results obtained was reasonably high following dosing of both formulations. No formal statistical comparison of the data has been performed. However, the higher $C_{max}$ and $AUC_{0-t}$ results, as well as shorter $T_{max}$ results, suggests that the formulations of the present invention have the potential to influence the plasma pharmacokinetics of raloxifene in a manner which will result in higher plasma concentrations being achieved both initially and throughout the treatment period.

Figure 27:
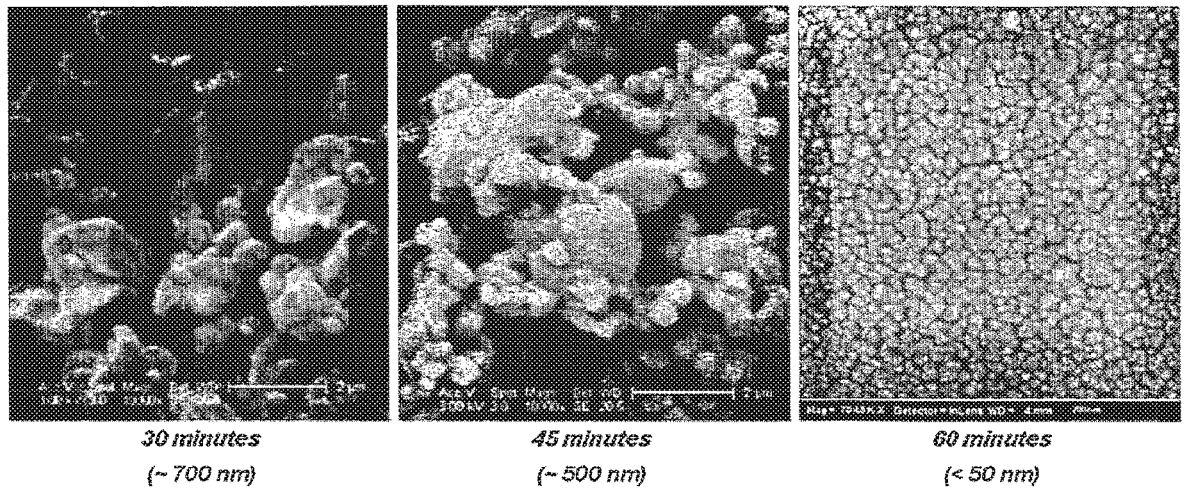
FIG. 27 comprises high resolution SEM images showing washed particulate fenofibrate produced by milling in an attrition mill for 30, 45 and 60 minutes.

E. Processing of Fenofibrate with Sodium Chloride Grinding Compound in a Cooled Attrition Mill Biologically active compound in the form of 5 g of fenofibrate,

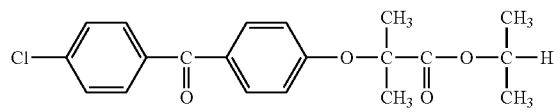

was placed in a 110 mL attrition mill (Union Process, Modified Model 01-HD) with 37 g sodium chloride corresponding to a 1:7 volume ratio (15%:85%) in a 20 mL volume with approximately 1 kg of 0.25 inch stainless steel milling balls. The milling vessel was maintainted at 0° C. through use of an external circulating chillier and milling was conducted under an argon gas flow. Milling was conducted at 500 rpm for 30, 45 and 60 minutes and the particles were washed in in deionized water to remove sodium chloride. FIG. 27 shows SEM pictures illustrating resultant particles of approximately 700 nm, 500 nm and less than 50 nm.

F. Raloxifene HCl Milled Using a Lactose Grinding Compound

Conventional active pharmaceutical compound raloxifene hydrochloride (0.5805 g) was introduced with lactose (4.284 g) into a steel vessel (75 cm³) with milling bodies comprising 10×10 mm steel balls. The total volume of the raloxifene hydrochloride/lactose mixture was 3 cm³ with 15 vol % of drug. Both the raloxifene hydrochloride and the lactose grinding compound were kept dry prior to milling by storage under vacuum and over $P_2O_5$. The steel milling chamber was closed under vacuum to remove moisture and air, to reduce degradation/oxidization.

The milling chamber was mounted on a Spex ball mill and was shaken for 15 min and cooled by a stream of compressed air. This resulted in the formation of a solid-dispersion consisting of raloxifene hydrochloride dispersed within a matrix of lactose.

The milling chamber was then carefully opened to release the vacuum, and any airborne particles allowed to settle. The milling chamber was opened in a fume hood to prevent inhalation of the fine particles, and the contents transferred through a 2 mm sieve (to remove the milling bodies) into 8 mL glass vials and stored in a vacuum desiccator over $P_2O_5$.

Figure 28A:
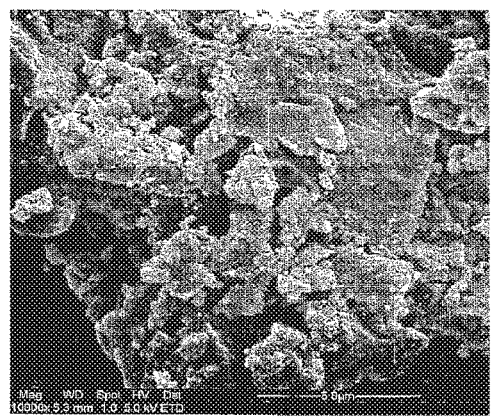
FIG. 28 comprises a high resolution SEM micrograph of raloxifene HCl in a lactose grinding compound.
Figure 28B:
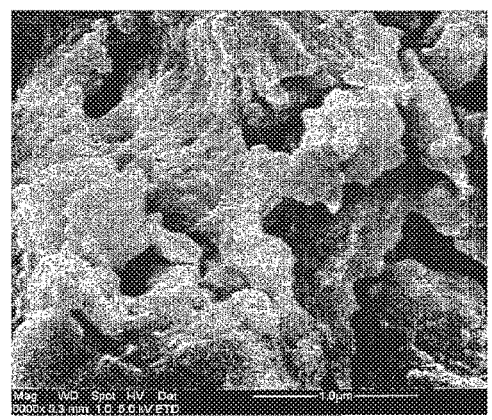
Figure 29:
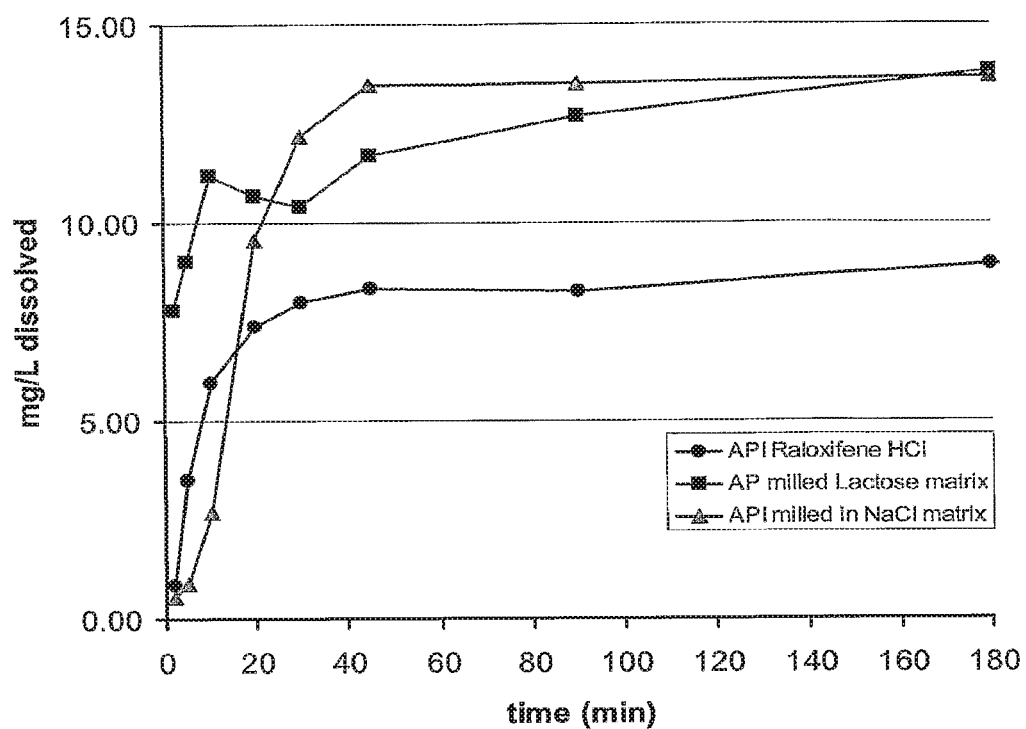
FIG. 29 compares in vitro dissolution of raloxifene HCl API with raloxifene milled with both sodium chloride and lactose as grinding compound and without removal of the grinding compound.

As can be seen from the SEM images (FIG. 28), the mixture of drug and lactose grinding compound contain particles below 100 nm which are believed to represent the raloxifene drug. FIG. 28a shows that some small particles well below 5 micron meters are formed after milling. At higher magnification a substructure, that shows particles with nano particle elements of about 100 nm can be seen The dissolution of the particles in lactose and NaCl grinding compounds were compared to the commercial API (FIG. 29). Both lactose and NaCl milled raloxifene showed enhanced dissolution properties relative to the API, which illustrates the ability to enhance the dissolution properties of drugs using a variety of grinding compounds and also demonstrates that the grinding compound need not be separated from the API prior to formulation to retain those enhanced properties.

G. Olanzapine Free Base Milled Using a Lactose Grinding Compound

Conventional active pharmaceutical compound olanzapine free base (0.5846 g) was introduced with lactose (4.284 g) into a steel vessel (75 cm³) with milling bodies comprising 10×10 mm steel balls. The total volume of the olanzapine /lactose mixture was 3 cm³ with 15 vol % of drug. Both the olanzapine freebase and the lactose grinding compound were kept dry prior to milling by storage under vacuum and over $P_2O_5$. The steel milling chamber was closed under vacuum to remove moisture and air, to reduce degradation/oxidization.

The milling chamber was mounted on a Spex ball mill and was shaken for 15 min and cooled by a stream of compressed air. This resulted in the formation of a solid-dispersion consisting of olanzapine free base dispersed within the lactose grinding compound.

The milling chamber was then carefully opened to release the vacuum, and closed to allow any airborne particles to settle. The milling chamber was then opened in a fume hood to prevent inhalation of the fine particles, and the contents transferred through a 2 mm sieve (to remove the milling bodies) into 8 mL glass vials and stored in a vacuum desiccator over $P_2O_5$.

Figure 30A:
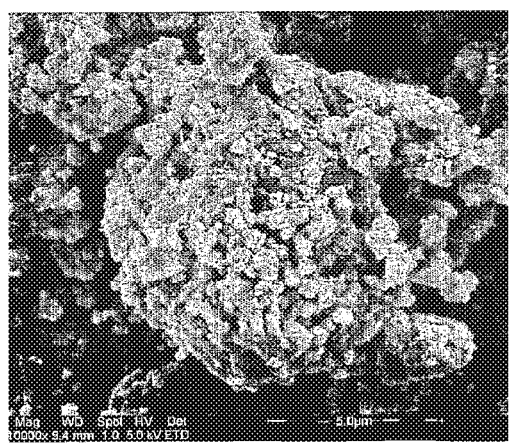
FIG. 30 comprises SEM micrographs showing that olanzapine free base can be ground with lactose to a fine powder with some larger agglomerates (FIG. 30a) and very fine particles of about 50-100 nm (FIG. 30b).
Figure 30B:
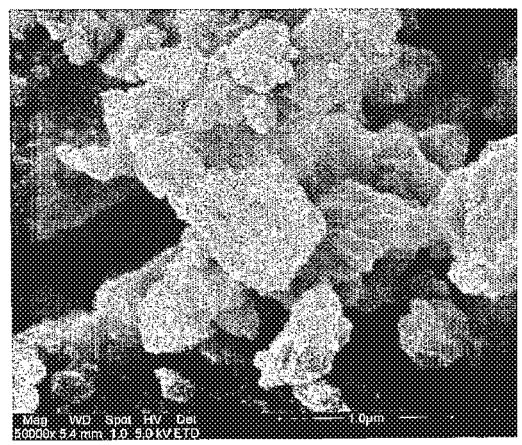

As can be seen from FIG. 30, fine particles can be obtained after milling in a lactose grinding compound.

It is expected that a broad range of GRAS compounds can be used as a grinding compound for the purposes of the present invention. However, some grinding compounds may offer specific advantages. For example, olanzapine-lactose grinding compound mixtures produced under similar conditions to olanzapine-sodium chloride grinding compound mixtures appear to exhibit superior flowability, which is advantageous in automated formulation systems.

It will be apparent to persons skilled in the materials and pharmaceutical arts that numerous enhancements and modifications can be made to the above described processes without departing from the basic inventive concepts. For example, in some applications the precursor biologically active agent compound may be pretreated and supplied to the process in the pretreated form. All such modifications and enhancements are considered to be within the scope of the present invention, the nature of which is to be determined from the foregoing description and the appended claims. Furthermore, the preceding examples are provided for illustrative purposes only, and are not intended to limit the scope of the processes or compositions of the invention.

We claim:

1. A dry milling method for producing a composition comprising nanoparticles of a biologically active compound, comprising the step of: dry milling particles of a biologically active compound, sodium lauryl sulfate, and a grinding compound selected from the group consisting of: sodium hydrogen sulfate, sodium hydrogen carbonate, sodium hydroxide, succinic acid, fumaric acid, maleic acid, tartaric acid, citric acid, ammonium chloride, methylamine hydrochloride, ammonium bromide, crystalline hydroxides, hydrogen carbonates, hydrogen carbonates of pharmaceutical acceptable alkali metals, sodium sulphate, sodium chloride, sodium metabisulphite, sodium thiosulphate, ammonium chloride, Glauber's salt, ammonium carbonate, sodium bisulphate, magnesium sulphate, potash alum, potassium chloride, sodium carbonate, sodium bicarbonate, potassium carbonate, potassium bicarbonate, and lactose in a mill comprising a plurality of milling bodies, for a time period sufficient to produce a composition comprising nanoparticles of the biologically active compound having an average size between 1,000 and 75 nm dispersed in at least partially milled grinding compound, wherein the particle size of the grinding compound and the particle size of the biologically active compound is reduced by the dry milling.

2. The method of claim 1, wherein the nanoparticles have an average size selected from the group consisting of: between 700 and 75 nm, between 500 and 75 nm, between 200 and 75 nm, and between 100 and 75 nm.

3. The method of claim 1, wherein the time period is a range selected from the group consisting of between 5 minutes and 2 hours, between 5 minutes and one hour, between 5 minutes and 45 minutes, between 5 minutes and 30 minutes, and between 10 minutes and 25 minutes.

4. The method of claim 3, wherein the milling bodies are selected from the group consisting of ceramics, glasses, polymers, ferromagnetics, and metals.

5. The method of claim 4, wherein the milling bodies are steel balls having a diameter selected from the group consisting of between 1 and 20 mm, between 2 and 15 mm, and between 3 and 10 mm.

6. The method of claim 1, wherein the biologically active compound is selected from the group consisting of anti-obesity drugs, central nervous system stimulants, carotenoids, corticosteroids, elastase inhibitors, anti-fungals, oncology therapies, anti-emetics, analgesics, cardiovascular agents, anti-inflammatory agents, anthelmintics, anti-arrhythrnic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives, astringents, alpha-adrenergic receptor blocking agents, beta-adrenoceptor blocking agents, blood products and substitutes, cardiac inotropic agents, contrast media, cough suppressants, diagnostic agents, diagnostic imaging agents, diuretics, dopaminergics, haemostatics, immunological agents, lipid regulating agents, muscle relaxants, parasympathomimetics, parathyroid calcitonin and biphosphonates, prostaglandins, radio-pharmaceuticals, sex hormones, anti-allergic agents, stimulants and anoretics, sympathomimetics, thyroid agents, vasodilators, and xanthines.

7. The method of claim 6, wherein the biologically active compound is selected from the group consisting of haloperidol, DL isoproterenol hydrochloride, terfenadine, propranolol hydrochloride, desipramine hydrochloride, salmeterol, sildenafil citrate, tadalafil, vardenafil, fenamic acids, piroxicam, naproxen, diclofenac, rofecoxib, ibuprofen, ondansetron, sumatriptan, naratryptan, ergotamine tartrate plus caffeine, methylsegide, olanzapine, raloxifene, and fenofibrate.

8. The method of claim 1, further comprising the step of removing at least a portion of the at least partially milled grinding compound after the dry milling step.

9. The method of claim 1, wherein the biologically active compound is selected from the group consisting of a non-steroidal anti-inflammatory drug and a COX-2 inhibitor.

* * * * *